US012667628B2

(12) United States Patent
Holt

(10) Patent No.: US 12,667,628 B2
(45) Date of Patent: Jun. 30, 2026

(54) COMPOSITIONS AND METHODS FOR GENE REPLACEMENT

(71) Applicant: Children's Medical Center Corporation, Boston, MA (US)

(72) Inventor: Jeffrey R. Holt, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 1218 days.

(21) Appl. No.: 17/624,145

(22) PCT Filed: Jul. 2, 2020

(86) PCT No.: PCT/US2020/040608
§ 371 (c)(1),
(2) Date: Dec. 30, 2021

(87) PCT Pub. No.: WO2021/003337
PCT Pub. Date: Jan. 7, 2021

(65) Prior Publication Data
US 2022/0395583 A1      Dec. 15, 2022

Related U.S. Application Data

(60) Provisional application No. 62/870,488, filed on Jul. 3, 2019.

(51) Int. Cl.
| | |
|---|---|
| *C07K 14/705* | (2006.01) |
| *A01K 67/0276* | (2024.01) |
| *A61K 48/00* | (2006.01) |
| *C12N 9/22* | (2006.01) |
| *C12N 15/10* | (2006.01) |
| *C12N 15/86* | (2006.01) |

(52) U.S. Cl.
CPC ........ *A61K 48/005* (2013.01); *A61K 48/0075* (2013.01); *C07K 14/705* (2013.01); *C12N 9/22* (2013.01); *C12N 15/102* (2013.01); *C12N 15/86* (2013.01); *A01K 2217/075* (2013.01); *A01K 2227/105* (2013.01); *A01K 2267/0306* (2013.01); *C12N 2310/20* (2017.05); *C12N 2750/14143* (2013.01); *C12N 2800/40* (2013.01)

(58) Field of Classification Search
None
See application file for complete search history.

(56) References Cited

U.S. PATENT DOCUMENTS

| | | | |
|---|---|---|---|
| 8,394,604 | B2 | 3/2013 | Liu et al. |
| 9,758,781 | B2 | 9/2017 | Smith et al. |
| 2004/0077842 | A1 | 4/2004 | Himawan |
| 2017/0073674 | A1 | 3/2017 | Maeder et al. |
| 2017/0321214 | A1 | 11/2017 | Zhang et al. |
| 2018/0282714 | A1 | 10/2018 | Joung et al. |
| 2018/0327779 | A1 | 11/2018 | Colella et al. |
| 2023/0090778 | A1 | 3/2023 | Holt et al. |

FOREIGN PATENT DOCUMENTS

| | | | | |
|---|---|---|---|---|
| WO | 2015054653 | A2 | 4/2015 | |
| WO | WO-2015134812 | A1 * | 9/2015 | ........... A61K 38/465 |
| WO | 2017053879 | A1 | 3/2017 | |
| WO | 2018145111 | A1 | 8/2018 | |
| WO | 2018162748 | A1 | 9/2018 | |
| WO | 2019173367 | A1 | 9/2019 | |
| WO | 2020014625 | A1 | 1/2020 | |
| WO | 2020079034 | A2 | 4/2020 | |

OTHER PUBLICATIONS

Cellecta. "Two-Vector CRISPR System Is Better Approach for Knockout Screens." Cellecta , 2018, cellecta.com/blogs/news/two-vector-crispr-system-is-better-approach-for-knockout-screens. (Year: 2018).*

Synthego. "Synthego | Full Stack Genome Engineering." Synthego. com, 2019, www.synthego.com/guide/how-to-use-crispr/sgrna. (Year: 2019).*

Zhao Y, Wang D, Zong L, Zhao F, Guan L, et al. (2014) A Novel DFNA36 Mutation in TMC1 Orthologous to the Beethoven (Bth) Mouse Associated with Autosomal Dominant Hearing Loss in a Chinese Family. PLOS One 9(5): e97064. https://doi.org/10.1371/journal.pone.0097064 (Year: 2014).*

Li P, Kleinstiver BP, Leon MY, Prew MS, Navarro-Gomez D, Greenwald SH, Pierce EA, Joung JK, Liu Q. Allele-Specific CRISPR-Cas9 Genome Editing of the Single-Base P23H Mutation for Rhodopsin-Associated Dominant Retinitis Pigmentosa. CRISPR J. Feb. 2018;1(1):55-64. doi: 10.1089/crispr.2017.0009. (Year: 2018).*

Giannelli S.G et al., Cas9/sgRNA selective targeting of the P23H Rhodopsin mutant allele for treating retinitis pigmentosa by intravitreal AAV9. PHP.B-based delivery, Human Molecular Genetics, vol. 27, Issue 5, Mar. 1, 2018, pp. 761-779, https://doi.org/10.1093/hmg/ddx438 (Year: 2018).*

Ahmed et al., "Emerging Gene Therapies for Genetic Hearing Loss," Journal of the Association for Research in Otolaryngology, 2017, vol. 18, pp. 649-670.

(Continued)

*Primary Examiner* — Anna Skibinsky
*Assistant Examiner* — Catherine L McCormick
(74) *Attorney, Agent, or Firm* — Greenberg Traurig, LLP; Melissa Hunter-Ensor; Evelyn M. Kwon

(57)      ABSTRACT

The present invention features a dual vector system for disrupting and replacing a target gene comprising a mutation (e.g., dominant, recessive mutation). Embodiments of the invention may also provide compositions comprising the dual vector system, and methods of using the dual vector system, including but not limited to methods of modifying the genome of a cell, methods of genomic editing, and methods of treating cells or a subject suffering from a genetic disease comprising a mutation.

18 Claims, 12 Drawing Sheets

Specification includes a Sequence Listing.

(56)　　　　　References Cited

OTHER PUBLICATIONS

Levy et al., "Cytosine and adenine base editing of the brain, liver, retina, heart and skeletal muscle of mice via adeno-associated viruses," Nature Biomedical Engineering, Jan. 2020, vol. 4, pp. 97-110.
Mcclements et al., "An AAV Dual Vector Strategy Ameliorates the Stargardt Phenotype in Adult Abca4-/- Mice," Human Gene Therapy, 2019, vol. 30, No. 5, pp. 590-600.
Shah et al., "Extein Residues Play an Intimate Role in the Rate-Limiting Step of Protein Trans-Splicing," Journal of the American Chemical Society, 2013, vol. 135, pp. 5839-5847.
Shubina-Oleinik et al., "Dual-vector gene therapy restores cochlear amplification and auditory sensitivity in a mouse model of DFNB16 hearing loss," Science Advances, Dec. 15, 2021, vol. 7, Article No. eabi7629, pp. 1-9.
Tornabene et al., "Intein-mediated protein trans-splicing expands adeno-associated virus transfer capacity in the retina," Science Translational Medicine, May 15, 2019, vol. 11, Article No. eaav4523, pp. 1-13.
Gyorgy et al., "Allele-Specific Deafness Gene Disruption through Discrimination of a Single Base Change by *S. aureus* Cas9KKH Prevents Progressive Hearing Loss after AAV Mediated Gene Delivery." Molecular Therapy, May 2018, vol. 26 No. 5S1, 170-171.
Kleinstiver et al., "Broadening the targeting range of *Staphylococcus aureus* CRISPR-Cas9 by modifying PAM recognition," Nature Biotechnology, Dec. 2015, vol. 33, No. 12, pp. 1293-1298 and p. 1299 containing Online Methods (7 total pages).
Yang et al., "A dual AA V system enables the Cas9-mediated correction of a metabolic liver disease in newborn mice," Nat. Biotechnol., 2016, vol. 34, pp. 334-338.

Office Action dated Nov. 28, 2024 in corresponding Japanese Patent Application No. 2021-577896 (5 pages).
English translation of Office Action dated Nov. 28, 2024 in corresponding Japanese Patent Application No. 2021-577896 (5 pages).
Gao et al., "Treatment of autosomal dominant hearing loss by in vivo delivery of genome editing agents," Nature, Jan. 11, 2018, vol. 553, No. 7687, pp. 217-221.
György et al., "Allele-specific gene editing prevents deafness in a model of dominant progressive hearing loss," Nature Medicine, Jul. 2019, vol. 25, No. 7, pp. 1123-1130.
György et al., "Gene Transfer with AAV9-PHP.B Rescues Hearing in a Mouse Model of Usher Syndrome 3A and Transduces Hair Cells in a Non-human Primate," Molecular Therapy: Methods & Clinical Development, Jun. 2019, vol. 13, pp. 1-13.
International Search Report and Written Opinion mailed Nov. 23, 2020 in corresponding International Patent Application No. PCT/US2020/040608 (9 pages).
Ma et al., "Integration and exchange of split dCas9 domains for transcriptional controls in mammalian cells," Nature Communications, 2016, vol. 7, Article No. 13056, pp. 1-7.
Mills et al., "Protein Splicing: How Inteins Escape from Precursor Proteins," The Journal of Biological Chemistry, May 23, 2014, vol. 289, No. 21, pp. 14498-14505.
Perler, Francine B., "InBase: the Intein Database," Nucleic Acids Research, 2002, vol. 30, No. 1, pp. 383-384.
Robertson et al., "Expanding the RNA-Guided Endonuclease Toolkit for Mouse Genome Editing," The CRISPR Journal, 2018, vol. 1, No. 6, pp. 431-439.
Stevens et al., "Design of a Split Intein with Exceptional Protein Splicing Activity," Journal of the American Chemical Society, 2016, vol. 138, pp. 2162-2165.
Extended European Search Report dated Jun. 30, 2023 in corresponding European Patent Application No. 20834446.5 (8 pages).

* cited by examiner

VECTOR 1: SaCas9-KKH

VECTOR 2: MmTmc1PAMmut + gRNA Tmc1-WT (18 + 1 nt)

FIG. 5B

```
                                              *
gRNA 11:     GGG -ᵗAG GAC CCC TTC AAG ACA GGGˢ (SEQ ID NO: 14)
gRNA 12:     GGA -ᵗG GAC CCC TTC AAG ACA GGG Tˢ (SEQ ID NO: 15)
gRNA 13:         GGA - ᵗC CCC TTC AAG ACA GGG TGG Gˢ(SEQ ID NO: 16)
gRNA 14:       GAG - ᵗGAC CCC TTC AAG ACA GGG TGˢ (SEQ ID NO: 17)
gRNA 15:          GAC - ᵗCCC TTC AAG ACA GGG TGG GAˢ(SEQ ID NO: 18)
gRNA 21: ⁵TG GTA ATG TCC CTC CTG GGGᵗ-AAGᵗ  (SEQ ID NO: 19)
```

```
Bth: ATG GTA ATG TCC CTC CTG GGG AAG TTC TGT CCC ACC CTG  (SEQ ID NO: 20)
     Met Val Met Ser Leu Leu Gly Lys Phe Cys Pro Thr Leu  (SEQ ID NO: 21)

WT:  ATG GTA ATG TCC CTC CTG GGG ATG TTC TGT CCC ACC CTG  (SEQ ID NO: 22)
                             Met mouse Tmc1
```

```
                                           *            #
gRNA 16:     GGG -ᵗAG GAT CCC TTC AAG ACA GGT Cˢ (SEQ ID NO: 23)
gRNA 17:     GGA -ᵗG GAT CCC TTC AAG ACA GGT TGˢ (SEQ ID NO: 24)
gRNA 18:        GGA - ᵗT CCC TTC AAG ACA GGT TGT Aˢ (SEQ ID NO: 25)
gRNA 19:      GAG -ᵗGAT CCC TTC AAG ACA GGT TGˢ (SEQ ID NO: 26)
         #   gRNA 20:       GAT - ᵗCCC TTC AAG ACA GGT TGT AAˢ (SEQ ID NO: 27)
gRNA 22: ⁵ᵗTG GTT ATG TCC CTC CTA GGGᵗ-AAG  (SEQ ID NO: 28)
```

```
Bth: ATG GTT ATG TCC CTC CTA GGG AAG TTC TGT CCA ACA TTG  (SEQ ID NO: 29)
     Met Val Met Ser Leu Leu Gly Lys Phe Cys Pro Thr Leu  (SEQ ID NO:30)

WT:  ATG GTT ATG TCC CTC CTA GGG ATG TTC TGT CCA ACA TTG  (SEQ ID NO: 31)
                             Met human TMC1
```

MEF +/+          (SEQ ID NO: 32)
Bth/+            (SEQ ID NO: 33)
Bth/+ gRNA 15    (SEQ ID NO: 34)

* gRNA 11
* gRNA 12
* gRNA 13
* gRNA 14
* gRNA 15
* gRNA 21 (PAM)

COMPOSITIONS AND METHODS FOR GENE REPLACEMENT

CROSS-REFERENCE TO RELATED APPLICATIONS

This application is the U.S. National Stage Application, pursuant to 35 U.S.C. § 371 of PCT International Application No. PCT/US2020/040608, filed Jul. 2, 2020 designating the United States and published in English, which claims priority to and the benefit of U.S. Provisional Application No. 62/870,488, filed Jul. 3, 2019, the disclosure of each of which is incorporated herein by reference in their entirety.

STATEMENT OF RIGHTS TO INVENTIONS MADE UNDER FEDERALLY SPONSORED RESEARCH

This invention was made with government support under Grant Nos. DC013521 and DC005439 awarded by the National Institutes of Health. The government has certain rights in the invention.

SEQUENCE LISTING STATEMENT

The instant application contains a Sequence Listing which has been submitted electronically in ASCII format and is hereby incorporated by reference in its entirety. Said ASCII copy, created on Jul. 31, 2020, is named 167705_011401_PCT_SL.txt and is 76,681 bytes in size.

BACKGROUND OF THE INVENTION

Gene editing is a promising method for the treatment of diseases and conditions associated with genetic alterations. However, methods for treating disease and disorders associated with dominant and recessive mutations remains challenging. Thus, there is a need for improved methods of gene editing.

SUMMARY OF THE INVENTION

As described below, the present invention features a dual vector system for disrupting and replacing a target gene comprising a mutation (e.g., dominant, recessive mutation).

In one aspect, the invention provides a dual vector system comprising a first vector comprising a polynucleotide encoding a Cas9-KKH polypeptide and a second vector comprising a polynucleotide encoding a guide RNA (gRNA) that binds a target gene comprising a mutation and a polynucleotide encoding a wild-type version of the target gene. One or both vectors may comprise at least one promoter selected from but not limited to: an Espin promoter, a protocadherin 15 (PCDH15) promoter, a protein tyrosine phosphatase receptor type Q (PTPRQ) promoter, a myosin VI (Myo6) promoter, a Potassium Voltage-Gated Channel Subfamily Q Member 4 (KCNQ4) promoter, a myosin VIIA (Myo7a) promoter, a synapsin promoter, a glial fibrillary acidic protein (GFAP) promoter, a cytomegalovirus (CMV) promoter, a CMV enhancer, chicken beta-Actin promoter and rabbit beta-Globin splice acceptor site (CAG) promoter, a chicken β-actin (CBA) promoter, a CBH promoter, a U6 type III RNA polymerase promoter, and a tetraspan membrane protein of hair cell stereocilia (TMHS) or lipoma HMGIC fusion partner-like 5 (LHFPL5) promoter. In some aspects, the promoter may be any one or more selected from: CMV and U6. One aspect provides the dual vector system, where the target gene comprises a mutation associated with a disease or condition. The target gene may be, for example, TMC1, and the mutation may be associated with hearing loss (e.g., progressive), such as those associated with a DFNA36 mutation. One vector of the dual vector system may comprise a Cas9-KKH polypeptide of SaCas9-KKH or SpCas9-KKH, where the Cas9-KKH is derived from *Staphylococcus aureus* or *Streptococcus pyogenes*, respectively. Another vector of the dual system may comprise a guide RNA selected from: gRNA 12, gRNA 15, and gRNA 16.

Another aspect of the invention may be directed to a dual vector system comprising: a) a first AAV9-PHP.B vector comprising a nucleotide sequence encoding Cas9-KKH; and b) a second AAV9-PHP.B vector comprising a nucleotide sequence encoding a guide RNA that binds a TMC1 gene comprising a DFNA36 mutation and a polynucleotide encoding a wild-type TMC1 gene. The guide RNA (gRNA) may be any one selected from: gRNA 12, gRNA 15, and gRNA 16.

A further aspect provides a composition comprising the dual vector system described herein. In some aspects, the composition may comprise a physiologically-acceptable carrier (including, e.g., diluent and/or excipient). Other aspects may be directed to a cell containing the dual vector system described here.

Yet another aspect of the invention provides a method of modifying the genome of a cell by contacting the cell with the dual vector system described here.

In one aspect of the invention, a method of genome editing may be provided, where the method comprising contacting a cell with the dual vector system described here.

Another aspect may be directed to a method of treating a subject suffering from a genetic disease by administering to the subject in need thereof, the dual vector system described here. The genetic disease may be an autosomal dominant disease, such as DFNA36 hearing loss, where the target gene is TMC1. The administering step may comprise contacting inner ear cells with the dual vector system, or composition or cells comprising the dual vector system described here. In some aspects, the administering may occur by injection. The method of treating a subject in need thereof with the dual vector system described here may result in the amelioration, reduction, or repair of the genetic disease suffered by the subject in need thereof.

Other features and advantages of the invention will be apparent from the detailed description and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "AAV9-PHP.B vector" is meant a viral vector comprising an AAV9-PHP.B polynucleotide or fragment. In one embodiment, the AAV9-PHP.B vector transfects at least 70% of inner hair cells and 70% of outer hair cells following administration to the inner ear of a subject or contact with a cell derived from an inner ear in vitro. In other embodiments, at least 85%, 90%, 95% or virtually 100% of inner hair cells and/or 85%, 90%, 95% or virtually 100% of outer hair cells are transfected. The transfection efficiency may be assessed using a gene encoding green fluorescent protein (GFP) in a mouse model. The sequence of an exemplary AAV9-PHP.B vector is provided below.

AAV9-PHP.B (SEQ ID NO: 1)

CCAATGATACGCGTCGGTGCGGGCCTCTTCGCTATTACGCCAGCTGGCGAAAGGGGGATGTGCTGCAAGGCGATT

AAGTTGGGTAACGCCAGGGTTTTCCCAGTCACGACGTTGTAAAACGACGGCCAGTGAGCGCGCGTAATACGACTC

ACTATAGGGCGAATTGGGTACATCGACGGTATCGGGGGAGCTCGCAGGGTCTCCATTTTGAAGCGGGAGGTTTGA

ACGCGCAGCCGCCATGCCGGGGTTTTACGAGATTGTGATTAAGGTCCCCAGCGACCTTGACGAGCATCTGCCCGG

CATTTCTGACAGCTTTGTGAACTGGGTGGCCGAGAAGGAATGGGAGTTGCCGCCAGATTCTGACATGGATCTGAA

TCTGATTGAGCAGGCACCCCTGACCGTGGCCGAGAAGCTGCAGCGCGACTTTCTGACGGAATGGCGCCGTGTGAG

TAAGGCCCCGGAGGCTCTTTTCTTTGTGCAATTTGAGAAGGGAGAGAGCTACTTCCACATGCACGTGCTCGTGGA

AACCACCGGGGTGAAATCCATGGTTTTGGGACGTTTCCTGAGTCAGATTCGCGAAAAACTGATTCAGAGAATTTA

CCGCGGGATCGAGCCGACTTTGCCAAACTGGTTCGCGGTCACAAAGACCAGAAATGGCGCCGGAGGCGGGAACAA

GGTGGTGGATGAGTGCTACATCCCCAATTACTTGCTCCCCAAAACCCAGCCTGAGCTCCAGTGGGCGTGGACTAA

TATGGAACAGTATTTAAGCGCCTGTTTGAATCTCACGGAGCGTAAACGGTTGGTGGCGCAGCATCTGACGCACGT

GTCGCAGACGCAGGAGCAGAACAAAGAGAATCAGAATCCCAATTCTGATGCGCCGGTGATCAGATCAAAAACTTC

AGCCAGGTACATGGAGCTGGTCGGGTGGCTCGTGGACAAGGGGATTACCTCGGAGAAGCAGTGGATCCAGGAGGA

CCAGGCCTCATACATCTCCTTCAATGCGGCCTCCAACTCGCGGTCCCAAATCAAGGCTGCCTTGGACAATGCGGG

AAAGATTATGAGCCTGACTAAAACCGCCCCCGACTACCTGGTGGGCCAGCAGCCCGTGGAGGACATTTCCAGCAA

TCGGATTTATAAAATTTTGGAACTAAACGGGTACGATCCCCAATATGCGGCTTCCGTCTTTCTGGGATGGGCCAC

GAAAAAGTTCGGCAAGAGGAACACCATCTGGCTGTTTGGGCCTGCAACTACCGGGAAGACCAACATCGCGGAGGC

CATAGCCCACACTGTGCCCTTCTACGGGTGCGTAAACTGGACCAATGAGAACTTTCCCTTCAACGACTGTGTGGA

CAAGATGGTGATCTGGTGGGAGGAGGGGAAGATGACCGCCAAGGTCGTGGAGTCGGCCAAAGCCATTCTCGGAGG

AAGCAAGGTGCGCGTGGACCAGAAATGCAAGTCCTCGGCCCAGATAGACCCGACTCCCGTGATCGTCACCTCCAA

CACCAATATGTGCGCCGTGATTGACGGGAACTCAACGACCTTCGAACACCAGCAGCCGTTGCAAGACCGGATGTT

CAAATTTGAACTCACCCGCCGTCTGGATCATGACTTTGGGAAGGTCACCAAGCAGGAAGTCAAAGACTTTTTCCG

GTGGGCAAAGGATCACGTGGTTGAGGTGGAGCATGAATTCTACGTCAAAAAGGGTGGAGCCAAGAAAAGACCCGC

CCCCAGTGACGCAGATATAAGTGAGCCCAAACGGGTGCGCGAGTCAGTTGCGCAGCCATCGACGTCAGACGCGGA

AGCTTCGATCAACTACGCGGACAGGTACCAAAACAAATGTTCTCGTCACGTGGGCATGAATCTGATGCTGTTTCC

CTGCAGACAATGCGAGAGACTGAATCAGAATTCAAATATCTGCTTCACTCACGGTGTCAAAGACTGTTTAGAGTG

CTTTCCCGTGTCAGAATCTCAACCCGTTTCTGTCGTCAAAAAGGCGTATCAGAAACTGTGCTACATTCATCACAT

CATGGGAAAGGTGCCAGACGCTTGCACTGCTTGCGACCTGGTCAATGTGGACTTGGATGACTGTGTTTCTGAACA

ATAAATGACTTAAACCAGGTATGAGTCGGCTGGATAAATCTAAAGTCATAAACGGCGCTCTGGAATTACTCAATG

AAGTCGGTATCGAAGGCCTGACGACAAGGAAACTCGCTCAAAAGCTGGGAGTTGAGCAGCCTACCCTGTACTGGC

ACGTGAAGAACAAGCGGGCCCTGCTCGATGCCCTGGCCATCGAGATGCTGGACAGGCATCATACCCACTTCTGCC

CCCTGGAAGGCGAGTCATGGCAAGACTTTCTGCGGAACAACGCCAAGTCATTCCGCTGTGCTCTCCTCTCACATC

GCGACGGGGCTAAAGTGCATCTCGGCACCCGCCCAACAGAGAAACAGTACGAAACCCTGGAAAATCAGCTCGCGT

TCCTGTGTCAGCAAGGCTTCTCCCTGGAGAACGCACTGTACGCTCTGTCCGCCGTGGGCCACTTTACACTGGGCT

GCGTATTGGAGGAACAGGAGCATCAAGTAGCAAAAGAGGGAAAGAGAGACACCTACCACCGATTCTATGCCCCCAC

TTCTGAGACAAGCAATTGAGCTGTTCGACCGGCAGGGAGCCGAACCTGCCTTCCTTTTCGGCCTGGAACTAATCA

TATGTGGCCTGGAGAAACAGCTAAAGTGCGAAAGCGGCGGGGCCGGCCGACGCCCTTGACGATTTTGACTTAGACA

-continued

TGCTCCCAGCCGATGCCCTTGACGACTTTGACCTTGATATGCTGCCTGCTGACGCTCTTGACGATTTTGACCTTG

ACATGCTCCCCGGGTAAATGCATGAATTCGATCTAGAGGGCCCTATTCTATAGTGTCACCTAAATGCTAGAGCTC

GCTGATCAGCCTCGACTGTGCCTTCTAGTTGCCAGCCATCTGTTGTTTGCCCCTCCCCCGTGCCTTCCTTGACCC

TGGAAGGTGCCACTCCCACTGTCCTTTCCTAATAAAATGAGGAAATTGCATCGCATTGTCTGAGTAGGTGTCATT

CTATTCTGGGGGGTGGGGTGGGGCAGGACAGCAAGGGGGAGGATTGGGAAGACAATAGCAGGCATGCTGGGGATG

CGGTGGGCTCTATGGCTTCTGAGGCGGAAAGAACCAGCTGGGGCTCGAATCAAGCTATCAAGTGCCACCTGACGT

CTCCCTATCAGTGATAGAGAAGTCGACACGTCTCGAGCTCCCTATCAGTGATAGAGAAGGTACGTCTAGAACGTC

TCCCTATCAGTGATAGAGAAGTCGACACGTCTCGAGCTCCCTATCAGTGATAGAGAAGGTACGTCTAGAACGTCT

CCCTATCAGTGATAGAGAAGTCGACACGTCTCGAGCTCCCTATCAGTGATAGAGAAGGTACGTCTAGAACGTCTC

CCTATCAGTGATAGAGAAGTCGACACGTCTCGAGCTCCCTATCAGTGATAGAGAAGGTACCCCCTATATAAGCAG

AGAGATCTGTTCAAATTTGAACTGACTAAGCGGCTCCCGCCAGATTTTGGCAAGATTACTAAGCAGGAAGTCAAG

GACTTTTTTGCTTGGGCAAAGGTCAATCAGGTGCCGGTGACTCACGAGTTTAAAGTTCCCAGGGAATTGGCGGGA

ACTAAAGGGGCGGAGAAATCTCTAAAACGCCCACTGGGTGACGTCACCAATACTAGCTATAAAAGTCTGGAGAAG

CGGGCCAGGCTCTCATTTGTTCCCGAGACGCCTCGCAGTTCAGACGTGACTGTTGATCCCGCTCCTCTGCGACCG

CTAGCTTCGATCAACTACGCAGACAGGTACCAAAACAAGTGTTCTCGTCACGTGGGCATTAATCTGATTCTGTTT

CCCTGCAGACAATGCGAGAGAATGAATCAGAACTCAAATATCTGCTTCACTCACGGACAGAAAGACTGTTTAGAG

TGCTTTCCCGTGTCAGAATCTCAACCCGTTTCTGTCGTCAAAAAGGCGTATCAGAAACTGTGCTACATTCATCAT

ATCATGGGAAAGGTGCCAGACGCTTGCACTGCCTGCGATCTGGTCAATGTGGATTTGGATGACTGCATCTTTGAA

CAATAAATGACTTAAGCCAGGTATGGCTGCCGATGGTTATCTTCCAGATTGGCTCGAGGACAACCTTAGTGAAGG

AATTCGCGAGTGGTGGGCTTTGAAACCTGGAGCCCCTCAACCCAAGGCAAATCAACAACATCAAGACAACGCTAG

AGGTCTTGTGCTTCCGGGTTACAAATACCTTGGACCCGGCAACGGACTCGACAAGGGGGAGCCGGTCAACGCAGC

AGACGCGGCGGCCCTCGAGCACGACAAAGCCTACGACCAGCAGCTCAAGGCCGGAGACAACCCGTACCTCAAGTA

CAACCACGCCGACGCCGAGTTCCAGGAGCGGCTCAAAGAAGATACGTCTTTTGGGGGCAACCTCGGGCGAGCAGT

CTTCCAGGCCAAAAAGAGGCTTCTTGAACCTCTTGGTCTGGTTGAGGAAGCGGCTAAGACGGCTCCTGGAAAGAA

GAGGCCTGTAGAGCAGTCTCCTCAGGAACCGGACTCCTCCGCGGGTATTGGCAAATCGGGTGCACAGCCCGCTAA

AAAGAGACTCAATTTCGGTCAGACTGGCGACACAGAGTCAGTCCCAGACCCTCAACCAATCGGAGAACCTCCCGC

AGCCCCCTCAGGTGTGGGATCTCTTACAATGGCTTCAGGTGGTGGCGCACCAGTGGCAGACAATAACGAAGGTGC

CGATGGAGTGGGTAGTTCCTCGGGAAATTGGCATTGCGATTCCCAATGGCTGGGGGACAGAGTCATCACCACCAG

CACCCGAACCTGGGCCCTGCCCACCTACAACAATCACCTCTACAAGCAAATCTCCAACAGCACATCTGGAGGATC

TTCAAATGACAACGCCTACTTCGGCTACAGCACCCCCTGGGGGTATTTTGACTTCAACAGATTCCACTGCCACTT

CTCACCACGTGACTGGCAGCGACTCATCAACAACAACTGGGGATTCCGGCCTAAGCGACTCAACTTCAAGCTCTT

TAACATTCAGGTCAAAGAGGTTACGGACAACAATGGAGTCAAGACCATCGCCAATAACCTTACCAGCACGGTCCA

GGTCTTCACGGACTCAGACTATCAGCTCCCGTACGTGCTCGGGTCGGCTCACGAGGGCTGCCTCCCGCCGTTCCC

AGCGGACGTTTTCATGATTCCTCAGTACGGGTATCTGACGCTTAATGATGGAAGCCAGGCCGTGGGTCGTTCGTC

CTTTTACTGCCTGGAATATTTCCCGTCGCAAATGCTAAGAACGGGTAACAACTTCCAGTTCAGCTACGAGTTTGA

GAACGTACCTTTCCATAGCAGCTACGCTCACAGCCAAAGCCTGGACCGACTAATGAATCCACTCATCGACCAATA

CTTGTACTATCTCTCTAGAACTATTAACGGTTCTGGACAGAATCAACAAACGCTAAAATTCAGTGTGGCCGGACC

CAGCAACATGGCTGTCCAGGGAAGAAACTACATACCTGGACCCAGCTACCGACAACAACGTGTCTCAACCACTGT

GACTCAAAACAACAACAGCGAATTTGCTTGGCCTGGAGCTTCTTCTTGGGCTCTCAATGGACGTAATAGCTTGAT

GAATCCTGGACCTGCTATGGCCTCTCACAAAGAAGGAGAGGACCGTTTCTTTCCTTTGTCTGGATCTTTAATTTT

-continued

```
TGGCAAACAAGGTACTGGCAGAGACAACGTGGATGCGGACAAAGTCATGATAACCAACGAAGAAGAAATTAAAAC

TACTAACCCGGTAGCAACGGAGTCCTATGGACAAGTGGCCACAAACCACCAGAGTGCCCAAACTTTGGCGGTGCC

TTTTAAGGCACAGGCGCAGACCGGTTGGGTTCAAAACCAAGGAATACTTCCGGGTATGGTTTGGCAGGACAGAGA

TGTGTACCTGCAAGGACCCATTTGGGCCAAAATTCCTCACACGGACGGCAACTTTCACCCTTCTCCGCTGATGGG

AGGGTTTGGAATGAAGCACCCGCCTCCTCAGATCCTCATCAAAAACACACCTGTACCTGCGGATCCTCCAACGGC

CTTCAACAAGGACAAGCTGAACTCTTTCATCACCCAGTATTCTACTGGTCAAGTCAGCGTGGAGATCGAGTGGGA

GCTGCAGAAGGAAAACAGCAAGCGCTGGAACCCGGAGATCCAGTACACTTCCAACTATTACAAGTCTAATAATGT

TGAATTTGCTGTTAATACTGAAGGTGTATATAGTGAACCCCGCCCCATTGGCACCAGATACCTGACTCGTAATCT

GTAAGTCGACTTGCTTGTTAATCAATAAACCGTTTAATTCGTTTCAGTTGAACTTTGGTCTCTGCGAAGGGCAAT

TCGTTTAAACCTGCAGGACTAGAGGTCCTGTATTAGAGGTCACGTGAGTGTTTTGCGACATTTTGCGACACCATG

TGGTCACGCTGGGTATTTAAGCCCGAGTGAGCACGCAGGGTCTCCATTTTGAAGCGGGAGGTTTGAACGCGCAGC

CGCCAAGCCGAATTCTGCAGATATCACATGTCCTAGGAACTATCGATCCATCACACTGGCGGCCGCTCGACTAGA

GCGGCCGCCACCGCGGTGGAGCTCCAGCTTTTGCGGACCGAATCGGAAAGAACATGTGAGCAAAAGGCCAGCAAA

AGGCCAGGAACCGTAAAAAGGCCGCGTTGCTGGCGTTTTTCCATAGGCTCCGCCCCCCTGACGAGCATCACAAAA

ATCGACGCTCAAGTCAGAGGTGGCGAAACCCGACAGGACTATAAAGATACCAGGCGTTTCCCCCTGGAAGCTCCC

TCGTGCGCTCTCCTGTTCCGACCCTGCCGCTTACCGGATACCTGTCCGCCTTTCTCCCTTCGGGAAGCGTGGCGC

TTTCTCATAGCTCACGCTGTAGGTATCTCAGTTCGGTGTAGGTCGTTCGCTCCAAGCTGGGCTGTGTGCACGAAC

CCCCCGTTCAGCCCGACCGCTGCGCCTTATCCGGTAACTATCGTCTTGAGTCCAACCCGGTAAGACACGACTTAT

CGCCACTGGCAGCAGCCACTGGTAACAGGATTAGCAGAGCGAGGTATGTAGGCGGTGCTACAGAGTTCTTGAAGT

GGTGGCCTAACTACGGCTACACTAGAAGAACAGTATTTGGTATCTGCGCTCTGCTGAAGCCAGTTACCTTCGGAA

AAAGAGTTGGTAGCTCTTGATCCGGCAAACAAACCACCGCTGGTAGCGGTGGTTTTTTTGTTTGCAAGCAGCAGA

TTACGCGCAGAAAAAAAGGATCTCAAGAAGATCCTTTGATCTTTTCTACGGGGTCTGACGCTCAGTGGAACGAAA

ACTCACGTTAAGGGATTTTGGTCATGAGATTATCAAAAAGGATCTTCACCTAGATCCTTTTAAATTAAAAATGAA

GTTTTAAATCAATCTAAAGTATATATGAGTAAACTTGGTCTGACAGTTACCAATGCTTAATCAGTGAGGCACCTA

TCTCAGCGATCTGTCTATTTCGTTCATCCATAGTTGCCTGACTCCCCGTCGTGTAGATAACTACGATACGGGAGG

GCTTACCATCTGGCCCCAGTGCTGCAATGATACCGCGAGACCCACGCTCACCGGCTCCAGATTTATCAGCAATAA

ACCAGCCAGCCGGAAGGGCCGAGCGCAGAAGTGGTCCTGCAACTTTATCCGCCTCCATCCAGTCTATTAATTGTT

GCCGGGAAGCTAGAGTAAGTAGTTCGCCAGTTAATAGTTTGCGCAACGTTGTTGCCATTGCTACAGGCATCGTGG

TGTCACGCTCGTCGTTTGGTATGGCTTCATTCAGCTCCGGTTCCCAACGATCAAGGCGAGTTACATGATCCCCCA

TGTTGTGCAAAAAAGCGGTTAGCTCCTTCGGTCCTCCGATCGTTGTCAGAAGTAAGTTGGCCGCAGTGTTATCAC

TCATGGTTATGGCAGCACTGCATAATTCTCTTACTGTCATGCCATCCGTAAGATGCTTTTCTGTGACTGGTGAGT

ACTCAACCAAGTCATTCTGAGAATAGTGTATGCGGCGACCGAGTTGCTCTTGCCCGGCGTCAATACGGGATAATA

CCGCGCCACATAGCAGAACTTTAAAAGTGCTCATCATTGGAAAACGTTCTTCGGGGCGAAAACTCTCAAGGATCT

TACCGCTGTTGAGATCCAGTTCGATGTAACCCACTCGTGCACCCAACTGATCTTCAGCATCTTTTACTTTCACCA

GCGTTTCTGGGTGAGCAAAAACAGGAAGGCAAAATGCCGCAAAAAAGGGAATAAGGGCGACACGGAAATGTTGAA

TACTCATACTCTTCCTTTTTCAATATTATTGAAGCATTTATCAGGGTTATTGTCTCATGAGCGGATACATATTTG

AATGTATTTAGAAAAATAAACAAATAGGGGTTCCGCGCACATTTCCCCGAAAAGTGCCACCTGACGTC.
```

By "administer" is meant providing one or more compositions (e.g., viral vectors) described herein to a subject in need thereof. Non-limiting routes of administration may include systemic administration (e.g., intravenous intraperitoneal, intramuscular, subdermal, or intracranial infusion), topical, injection, infusion, electroporation, or ex vivo, where cells (e.g., tissues, bone marrow aspirates, lymphocytes, stem cells) from a subject in need thereof are removed and returned to the subject after incorporation of the viral vectors. By way of example and without limitation, the composition (e.g., viral vectors) of the disclosure may be administered by injection, for example, into the cochlea. Other routes that deliver the composition to cells affected by a mutation can be employed. Administration can be, for example, by bolus injection or by gradual perfusion over time.

By "agent" is meant any small molecule chemical compound, antibody, nucleic acid molecule, or polypeptide, or fragments thereof.

By "alteration" is meant a change (increase or decrease) in the expression levels or activity of a gene or polypeptide as detected by standard art known methods such as those described herein. As used herein, an alteration includes a 10% or greater change (e.g., a 25% change, a 40% change, a 50% or greater change) in expression levels.

By "ameliorate" is meant decrease, suppress, attenuate, diminish, arrest, or stabilize the development or progression of a disease. Exemplary diseases associated with a dominant or a recessive mutation.

By "Anc80 polypeptide" is meant a capsid polypeptide having at least about 85% or greater (e.g., 90%, 95%, 97%, 98%, 99%) amino acid identity to the following polypeptide sequence:

```
                                          (SEQ ID NO: 2)
MAADGYLPDWLEDNLSEGIREWWDLKPGAPKPKANQQKQDDGRGLVLPG

YKYLGPFNGLDKGEPVNAADAAALEHDKAYDQQLKAGDNPYLRYNHADA

EFQERLQEDTSFGGNLGRAVFQAKKRVLEPLGLVEEGAKTAPGKKRPVE

QSPQEPDSSSGIGKKGQQPARKRLNFGQTGDSESVPDPQPLGEPPAAPS
```

-continued

```
GVGSNTMAAGGGAPMADNNEGADGVGNASGNWHCDSTWLGDRVITTSTR

TALPTYNNHLYKQISSQSGGSTNDNTYFGYSTPWGYFDFNRFHCHFSPR

DWQRLINNNWGFRPKKLNFKLFNIQVKEVTTNDGTTTIANNLTSTVQVF

TDSEYQLPYVLGSAHQGCLPPFPADVFMIPQYGYLTLNNGSQAVGRSSF

YCLEYFPSQMLRTGNNFQFSYTFEDVPFHSSYAHSQSLDRLMNPLIDQY

LYYLSRTQTTSGTAGNRTLQFSQAGPSSMANQAKNWLPGPCYRQQRVSK

TTNQNNNSNFAWTGATKYHLNGRDSLVNPGPAMATHKDDEDKFFPMSGV

LIFGKQGAGNSNVDLDNVMITNEEEIKTTNPVATEEYGTVATNLQSANT

APATGTVNSQGALPGMVWQDRDVYLQGPIWAKIPHTDGHFHPSPLMGGF

GLKHPPPQILIKNTPVPANPPTTFSPAKFASFITQYSTGQVSVEIEELQ

KENSKRWNPEIQYTSNYNKSTNVDFAVDTNGVYSEPRPIGTRYLTRNL.
```

By "Anc80 polynucleotide" is meant a nucleic acid molecule encoding an Anc80 polypeptide.

By "Cas9 (CRISPR associated protein 9) polypeptide" is meant a polypeptide or fragment thereof having at least about 85% (e.g., 90%, 95%, 97%, 98%, 99%) amino acid identity to NCBI Accession No. NP_269215 and having RNA binding activity, DNA binding activity, and/or DNA cleavage activity (e.g., endonuclease or nickase activity). The Cas9 enzyme may be selected from *S. aureus, S. pneumoniae, S. pyogenes,* or *S. thermophilus* Cas9. In some embodiments, the enzyme may be a Cas9 homolog or include mutated Cas9 from any of the aforementioned organisms. An exemplary Cas9 polypeptide sequence is provided below.

```
Cas9:
                                               (SEQ ID NO: 3)
    1  MDKKYSIGLD  IGTNSVGWAV  ITDEYKVPSK  KFKVLGNTDR  HSIKKNLIGA  LLFDSGETAE

61  ATRLKRTARR  RYTRRKNRIC  YLQEIFSNEM  AKVDDSFFHR  LEESFLVEED  KKHERHPIFG

121  NIVDEVAYHE  KYPTIYHLRK  KLVDSTDKAD  LRLIYLALAH  MIKFRGHFLI  EGDLNPDNSD

181  VDKLFIQLVQ  TYNQLFEENP  INASGVDAKA  ILSARLSKSR  RLENLIAQLP  GEKKNGLFGN

241  LIALSLGLTP  NFKSNFDLAE  DAKLQLSKDT  YDDDLDNLLA  QIGDQYADLF  LAAKNLSDAI

301  LLSDILRVNT  EITKAPLSAS  MIKRYDEHHQ  DLTLLKALVR  QQLPEKYKEI  FFDQSKNGYA

361  GYIDGGASQE  EFYKFIKPIL  EKMDGTEELL  VKLNREDLLR  KQRTFDNGSI  PHQIHLGELH

421  AILRRQEDFY  PFLKDNREKI  EKILTFRIPY  YVGPLARGNS  RFAWMTRKSE  ETITPWNFEE

481  VVDKGASAQS  FIERMTNFDK  NLPNEKVLPK  HSLLYEYFTV  YNELTKVKYV  TEGMRKPAFL

541  SGEQKKAIVD  LLFKTNRKVT  VKQLKEDYFK  KIECFDSVEI  SGVEDRFNAS  LGTYHDLLKI

601  IKDKDFLDNE  ENEDILEDIV  LTLTLFEDRE  MIEERLKTYA  HLFDDKVMKQ  LKRRRYTGWG

661  RLSRKLINGI  RDKQSGKTIL  DFLKSDGFAN  RNFMQLIHDD  SLTFKEDIQK  AQVSGQGDSL

721  HEHIANLAGS  PAIKKGILQT  VKVVDELVKV  MGRHKPENIV  IEMARENQTT  QKGQKNSRER

781  MKRIEEGIKE  LGSQILKEHP  VENTQLQNEK  LYLYYLQNGR  DMYVDQELDI  NRLSDYDVDH

841  IVPQSFLKDD  SIDNKVLTRS  DKNRGKSDNV  PSEEVVKKMK  NYWRQLLNAK  LITQRKFDNL

901  TKAERGGLSE  LDKAGFIKRQ  LVETRQITKH  VAQILDSRMN  TKYDENDKLI  REVKVITLKS

961  KLVSDFRKDF  QFYKVREINN  YHHAHDAYLN  AVVGTALIKK  YPKLESEFVY  GDYKVYDVRK

1021  MIAKSEQEIG  KATAKYFFYS  NIMNFFKTEI  TLANGEIRKR  PLIETNGETG  EIVWDKGRDF

1081  ATVRKVLSMP  QVNIVKKTEV  QTGGFSKESI  LPKRNSDKLI  ARKKDWDPKK  YGGFDSPTVA
```

-continued

```
1141  YSVLVVAKVE  KGKSKKLKSV  KELLGITIME  RSSFEKNPID  FLEAKGYKEV  KKDLIIKLPK

1201  YSLFELENGR  KRMLASAGEL  QKGNELALPS  KYVNFLYLAS  HYEKLKGSPE  DNEQKQLFVE

1261  QHKHYLDEII  EQISEFSKRV  ILADANLDKV  LSAYNKHRDK  PIREQAENII  HLFTLTNLGA

1321  PAAFKYFDTT  IDRKRYTSTK.
```

By "Cas 9 nucleic acid molecule" is meant a polynucle-
otide encoding a Cas9 polypeptide or fragment thereof. An
exemplary *S. pyogenes* Cas9 nucleic acid molecule sequence
is provided at NCBI Accession No. NC_002737 and is
shown below.

```
                                                          (SEQ ID NO: 4)
   1  ATGGATAAGA  AATACTCAAT  AGGCTTAGAT  ATCGGCACAA  ATAGCGTCGG  ATGGGCGGTG

61  ATCACTGATG  AATATAAGGT  TCCGTCTAAA  AAGTTCAAGG  TTCTGGGAAA  TACAGACCGC

121  CACAGTATCA  AAAAAAATCT  TATAGGGGCT  CTTTTATTTG  ACAGTGGAGA  GACAGCGGAA

181  GCGACTCGTC  TCAAACGGAC  AGCTCGTAGA  AGGTATACAC  GTCGGAAGAA  TCGTATTTGT

241  TATCTACAGG  AGATTTTTTC  AAATGAGATG  GCGAAAGTAG  ATGATAGTTT  CTTTCATCGA

301  CTTGAAGAGT  CTTTTTTGGT  GGAAGAAGAC  AAGAAGCATG  AACGTCATCC  TATTTTTGGA

361  AATATAGTAG  ATGAAGTTGC  TTATCATGAG  AAATATCCAA  CTATCTATCA  TCTGCGAAAA

421  AAATTGGTAG  ATTCTACTGA  TAAAGCGGAT  TTGCGCTTAA  TCTATTTGGC  CTTAGCGCAT

481  ATGATTAAGT  TTCGTGGTCA  TTTTTTGATT  GAGGGAGATT  TAAATCCTGA  TAATAGTGAT

541  GTGGACAAAC  TATTTATCCA  GTTGGTACAA  ACCTACAATC  AATTATTTGA  AGAAAACCCT

601  ATTAAGGCAA  GTGGAGTAGA  TGCTAAAGCG  ATTCTTTCTG  CACGATTGAG  TAAATCAAGA

661  CGATTAGAAA  ATCTCATTGC  TCAGCTCCCC  GGTGAGAAGA  AAAATGGCTT  ATTTGGGAAT

721  CTCATTGCTT  TGTCATTGGG  TTTGACCCCT  AATTTTAAAT  CAAATTTTGA  TTTGGCAGAA

781  GATGGTAAAT  TACAGCTTTC  AAAAGATACT  TACGATGATG  ATTTAGATAA  TTTATTGGCG

841  CAAATTGGAG  ATCAATATGC  TGATTTGTTT  TTGGCAGCTA  AGAATTTATC  AGATGCTATT

901  TTACTTTCAG  ATATCCTAAG  AGTAAATACT  GAAATAACTA  AGGCTCCCCT  ATCAGCTTCA

961  ATGATTAAAC  GCTACGATGA  ACATCATCAA  GACTTGACTC  TTTTAAAAGC  TTTAGTTCGA

1021  CAACAACTTC  CAGAAAAGTA  TAAAGAAATC  TTTTTTGATC  AATCAAAAAA  CGGATATGCA

1081  GGTTATATTG  ATGGGGGAGC  TAGCCAAGAA  GAATTTTATA  AATTTATCAA  ACCAATTTTA

1141  GAAAAAATGG  ATGGTACTGA  GGAATTATTG  GTGAAACTAA  ATCGTGAAGA  TTTGCTGCGC

1201  AAGCAACGGA  CCTTTGACAA  CGGCTCTATT  CCCCATCAAA  TTCACTTGGG  TGAGCTGCAT

1261  GCTATTTTGA  GAAGACAAGA  AGACTTTTAT  CCATTTTTAA  AAGACAATCG  TGAGAAGATT

1321  GAAAAAATCT  TGACTTTTCG  AATTCCTTAT  TATGTTGGTC  CATTGGCGCG  TGGCAATAGT

1381  CGTTTTGCAT  GGATGACTCG  GAAGTCTGAA  GAAACAATTA  CCCCATGGAA  TTTTGAAGAA

1441  GTTGTCGATA  AAGGTGCTTC  AGCTCAATCA  TTTATTGAAC  GCATGACAAA  CTTTGATAAA

1501  AATCTTCCAA  ATGAAAAAGT  ACTACCAAAA  CATAGTTTGC  TTTATGAGTA  TTTTACGGTT

1561  TATAACGAAT  TGACAAAGGT  CAAATATGTT  ACTGAAGGAA  TGCGAAAACC  AGCATTTCTT

1621  TCAGGTGAAC  AGAAGAAAGC  CATTGTTGAT  TTACTCTTCA  AAACAAATCG  AAAAGTAACC

1681  GTTAAGCAAT  TAAAAGAAGA  TTATTTCAAA  AAAATAGAAT  GTTTTGATAG  TGTTGAAATT

1741  TCAGGAGTTG  AAGATAGATT  TAATGCTTCA  TTAGGTACCT  ACCATGATTT  GCTAAAAATT

1801  ATTAAAGATA  AAGATTTTTT  GGATAATGAA  GAAAATGAAG  ATATCTTAGA  GGATATTGTT
```

-continued

```
1861 TTAACATTGA CCTTATTTGA AGATAGGGAG ATGATTGAGG AAAGACTTAA AACATATGCT

1921 CACCTCTTTG ATGATAAGGT GATGAAACAG CTTAAACGTC GCCGTTATAC TGGTTGGGGA

1981 CGTTTGTCTC GAAAATTGAT TAATGGTATT AGGGATAAGC AATCTGGCAA AACAATATTA

2041 GATTTTTTGA AATCAGATGG TTTTGCCAAT CGCAATTTTA TGCAGCTGAT CCATGATGAT

2101 AGTTTGACAT TTAAAGAAGA CATTCAAAAA GCACAAGTGT CTGGACAAGG CGATAGTTTA

2161 CATGAACATA TTGCAAATTT AGCTGGTAGC CCTGCTATTA AAAAAGGTAT TTTACAGACT

2221 GTAAAAGTTG TTGATGAATT GGTCAAAGTA ATGGGGCGGC ATAAGCCAGA AAATATCGTT

2281 ATTGAAATGG CACGTGAAAA TCAGACAACT CAAAAGGGCC AGAAAAATTC GCGAGAGCGT

2341 ATGAAACGAA TCGAAGAAGG TATCAAAGAA TTAGGAAGTC AGATTCTTAA AGAGCATCCT

2401 GTTGAAAATA CTCAATTGCA AAATGAAAAG CTCTATCTCT ATTATCTCCA AAATGGAAGA

2461 GACATGTATG TGGACCAAGA ATTAGATATT AATCGTTTAA GTGATTATGA TGTCGATCAC

2521 ATTGTTCCAC AAAGTTTCCT TAAAGACGAT TCAATAGACA ATAAGGTCTT AACGCGTTCT

2581 GATAAAAATC GTGGTAAATC GGATAACGTT CCAAGTGAAG AAGTAGTCAA AAAGATGAAA

2641 AACTATTGGA GACAACTTCT AAACGCCAAG TTAATCACTC AACGTAAGTT TGATAATTTA

2701 ACGAAAGCTG AACGTGGAGG TTTGAGTGAA CTTGATAAAG CTGGTTTTAT CAAACGCCAA

2761 TTGGTTGAAA CTCGCCAAAT CACTAAGCAT GTGGCACAAA TTTTGGATAG TCGCATGAAT

2821 ACTAAATACG ATGAAAATGA TAAACTTATT CGAGAGGTTA AAGTGATTAC CTTAAAATCT

2881 AAATTAGTTT CTGACTTCCG AAAAGATTTC CAATTCTATA AGTACGTGA GATTAACAAT

2941 TAGCATCATG CCCATGATGC GTATCTAAAT GCCGTCGTTG GAACTGCTTT GATTAAGAAA

3001 TATCCAAAAC TTGAATCGGA GTTTGTCTAT GGTGATTATA AAGTTTATGA TGTTCGTAAA

3061 ATGATTGCTA AGTCTGAGCA AGAAATAGGC AAAGCAACCG CAAAATATTT CTTTTACTCT

3121 AATATCATGA ACTTCTTCAA AACAGAAATT ACACTTGCAA ATGGAGAGAT TCGCAAACGC

3181 CCTCTAATCG AAACTAATGG GGAAACTGGA GAAATTGTCT GGGATAAAGG GCGAGATTTT

3241 GCCACAGTGC GCAAAGTATT GTCCATGCCC CAAGTCAATA TTGTCAAGAA AACAGAAGTA

3301 CAGACAGGCG GATTCTCCAA GGAGTCAATT TTACCAAAAA GAAATTCGGA CAAGCTTATT

3361 GCTCGTAAAA AAGACTGGGA TCCAAAAAAA TATGGTGGTT TTGATAGTCC AACGGTAGCT

3421 TATTCAGTCC TAGTGGTTGC TAAGGTGGAA AAAGGGAAAT CGAAGAAGTT AAAATCCGTT

3481 AAAGAGTTAC TAGGGATCAC AATTATGGAA AGAAGTTCCT TTGAAAAAAA TCCGATTGAC

3541 TTTTTAGAAG CTAAAGGATA TAAGGAAGTT AAAAAAGACT TAATCATTAA ACTACCTAAA

3601 TATAGTCTTT TTGAGTTAGA AAACGGTCGT AAACGGATGC TGGCTAGTGC CGGAGAATTA

3661 CAAAAAGGAA ATGAGCTGGC TCTGCCAAGC AAATATGTGA ATTTTTTATA TTTAGCTAGT

3721 CATTATGAAA AGTTGAAGGG TAGTCCAGAA GATAACGAAC AAAAACAATT GTTTGTGGAG

3781 CAGCATAAGC ATTATTTAGA TGAGATTATT GAGCAAATCA GTGAATTTTC TAAGCGTGTT

3841 ATTTTAGCAG ATGCCAATTT AGATAAAGTT CTTAGTGCAT ATAACAAACA TAGAGACAAA

3901 CCAATACGTG AACAAGCAGA AAATATTATT CATTTATTTA CGTTGACGAA TCTTGGAGCT

3961 CCCGCTGCTT TTAAATATTT TGATACAACA ATTGATCGTA AACGATATAC GTCTACAAAA

4021 GAAGTTTTAG ATGCCACTCT TATCCATCAA TCCATCACTG GTCTTTATGA AACACGCATT

4081 GATTTGAGTC AGCTAGGAGG TGACTGA
```

SaCas9:

(SEQ ID NO: 5)

```
MAPKKKRKVGIHGVPAAKRNYILGLDIGITSVGYGIIDYETRDVIDAGV

RLFKEANVENNEGRRSKRGARRLKRRRRHRIQRVKKLLFDYNLLTDHSE

LSGINPYEARVKGLSQKLSEEEFSAALLHLAKRRGVHNVNEVEEDTGNE

LSTKEQISRNSKALEEKYVAELQLERLKKDGEVRGSINRFKTSDYVKEA

KQLLKVQKAYHQLDQSFIDTYIDLLETRRTYYEGPGEGSPFGWKDIKEW

YEMLMGHCTYFPEELRSVKYAYNADLYNALNDLNNLVITRDENEKLEYY

EKFQIIENVFKQKKKPTLKQIAKEILVNEEDIKGYRVTSTGKPEFTNLK

VYHDIKDITARKEIIENAELLDQIAKILTIYQSSEDIQEELTNLNSELT

QEEIEQISNLKGYTGTHNLSLKAINLILDELWHTNDNQIAIFNRLKLVP

KKVDLSQQKEIPTTLVDDFILSPVVKRSFIQSIKVINAIIKKYGLPNDI

IIELAREKNSKDAQKMINEMQKRNRQTNERIEEIIRTTGKENAKYLIEK

IKLHDMQEGKCLYSLEAIPLEDLLNNPFNYEVDHIIPRSVSFDNSFNNK

VLVKQEENSKKGNRTPFQYLSSSDSKISYETFKKHILNLAKGKGRISKT

KKEYLLEERDINRFSVQKDFINRNLVDTRYATRGLMNLLRSYFRVNNLD

VKVKSINGGFTSFLRRKWKFKKERNKGYKHHAEDALIIANADFIFKEWK

KLDKAKKVMENQMFEEKQAESMPEIETEQEYKEIFITPHQIKHIKDFKD

YKYSHRVDKKPNRELINDTLYSTRKDDKGNTLIVNNLNGLYDKDNDKLK

KLINKSPEKLLMYHHDPQTYQKLKLIMEQYGDEKNPLYKYYEETGNYLT

KYSKKDNGPVIKKIKYYGNKLNAHLDITDDYPNSRNKVVKLSLKPYRFD

VYLDNGVYKFVTVKNLDVIKKENYYEVNSKCYEEAKKLKKISNQAEFIA

SFYNNDLIKINGELYRVIGVNNDLLNRIEVNMIDITYREYLENMNDKRP

PRIIKTIASKTQSIKKYSTDILGNLYEVKSKKHPQIIKKGKRPAATKKA

GQAKKKKGS
```

SaCas9-KKH:

A PAM variant of *Staphylococcus aureus* Cas9 (SaCas9-KKH) selectively and efficiently disrupts the mutant allele, but not the wild-type Tmc1/TMC1 allele, in Beethoven mice and in a DFNA36 human cell line. AAV-mediated SaCas9-KKH delivery prevented deafness in Beethoven mice up to one year post transduction. The SaCas9-KKH amino acid sequence is provided below. Bold and underlined text in the amino acid sequence denotes variation from SaCas9.

(SEQ ID NO: 6)

```
MAPKKKRKVGIHGVPAAKRNYILGLDIGITSVGYGIIDYETRDVIDAGV

RLFKEANVENNEGRRSKRGARRLKRRRRHRIQRVKKLLFDYNLLTDHSE

LSGINPYEARVKGLSQKLSEEEFSAALLHLAKRRGVHNVNEVEEDTGNE

LSTKEQISRNSKALEEKYVAELQLERLKKDGEVRGSINRFKTSDYVKEA

KQLLKVQKAYHQLDQSFIDTYIDLLETRRTYYEGPGEGSPFGWKDIKEW

YEMLMGHCTYFPEELRSVKYAYNADLYNALNDLNNLVITRDENEKLEYY

EKFQIIENVFKQKKKPTLKQIAKEILVNEEDIKGYRVTSTGKPEFTNLK

VYHDIKDITARKEIIENAELLDQIAKILTIYQSSEDIQEELTNLNSELT

QEEIEQISNLKGYTGTHNLSLKAINLILDELWHTNDNQIAIFNRLKLVP
```

```
KKVDLSQQKEIPTTLVDDFILSPVVKRSFIQSIKVINAIIKKYGLPNDI

IIELAREKNSKDAQKMINEMQKRNRQTNERIEEIIRTTGKENAKYLIEK

IKLHDMQEGKCLYSLEAIPLEDLLNNPFNYEVDHIIPRSVSFDNSFNNK

VLVKQEENSKKGNRTPFQYLSSSDSKISYETFKKHILNLAKGKGRISKT

KKEYLLEERDINRFSVQKDFINRNLVDTRYATRGLMNLLRSYFRVNNLD

VKVKSINGGFTSFLRRKWKFKKERNKGYKHHAEDALIIANADFIFKEWK

KLDKAKKVMENQMFEEKQAESMPEIETEQEYKEIFITPHQIKHIKDFKD

YKYSHRVDKKPNRKLINDTLYSTRKDDKGNTLIVNNLNGLYDKDNDKLK

KLINKSPEKLLMYHHDPQTYQKLKLIMEQYGDEKNPLYKYYEETGNYLT

KYSKKDNGPVIKKIKYYGNKLNAHLDITDDYPNSRNKVVKLSLKPYRFD

VYLDNGVYKFVTVKNLDVIKKENYYEVNSKCYEEAKKLKKISNQAEFIA

SFYKNDLIKINGELYRVIGVNNDLLNRIEVNMIDITYREYLENMNDKRP

PHIIKTIASKTQSIKKYSTDILGNLYEVKSKKHPQIIKKGKRPAATKKA

GQAKKKKGS
```

Kleinstiver et al. (Nat Biotechnol. 2015 December; 33(12):1293-1298. doi: 10.1038/nbt.3404. Epub 2015 Nov. 2) describes SaCas9-KKH.

"Detect" refers to identifying the presence, absence or amount of the analyte to be detected.

By "disease" is meant any condition or disorder that damages or interferes with the normal function of a cell, tissue, or organ. Examples of diseases include any pathology, such as a hearing disorder, associated with genetic variation (e.g., a mutation).

By "effective amount" is meant the amount of an agent required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, at least 10% (e.g., 20%, 30%, 40%, 50%, 60%, 70%, 80%, or 90%) of the entire length of the reference nucleic acid molecule or polypeptide. A fragment may contain 10 or greater (e.g., 20, 30, 40, 50, 60, 70, 80, 90, or 100, 200, 300, 400, 500, 600, 700, 800, 900, or 1000) nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "identity" is meant the amino acid or nucleic acid sequence identity between a sequence of interest and a reference sequence. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BEST-FIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-100 indicating a closely related sequence.

The term "indel" refers to the insertion or deletion of at least one nucleotide at a locus in a nucleic acid molecule. An indel present in the coding region of a gene may result in a frameshift mutation resulting in a premature stop codon or other signal for the expressed protein to be degraded.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high-performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. In some embodiments, the preparation is at least 75% or greater (e.g., at least 90%, at least 99%), by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

By "mechanosensation" is meant a response to a mechanical stimulus. Touch, hearing, and balance of examples of the conversion of a mechanical stimulus into a neuronal signal.

Mechanosensory input is converted into a response to a mechanical stimulus through a process termed "mechano-transduction."

As used herein, "obtaining" as in "obtaining an agent" includes synthesizing, purchasing, or otherwise acquiring the agent.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

By "promoter" is meant a polynucleotide sufficient to direct transcription of a downstream polynucleotide.

By "Espin promoter" is meant a regulatory polynucleotide sequence derived from NCBI Reference Sequence: NG_015866.1 that is sufficient to direct expression of a downstream polynucleotide in an outer or inner hair cell, vestibular hair cell, a spiral ganglion, or a vestibular ganglion. In one embodiment, the Espin promoter comprises or consists of at least about 350 base pairs (e.g., 500, 1000, 2000, 3000, 4000, 5000), or more base pairs upstream of an Espin coding sequence.

By "protocadherin related 15 (PCDH15) promoter" is meant a regulatory polynucleotide sequence derived from NCBI Reference Sequence: NG_009191 that is sufficient to direct expression of a downstream polynucleotide in an outer or inner hair cell, vestibular hair cell, a spiral ganglion, or a vestibular ganglion. In one embodiment, the PCDH15 promoter comprises at least about 350 base pairs (e.g., 500, 1000, 2000, 3000, 4000, 5000), or more base pairs upstream of an PCDH15 coding sequence. In some embodiments, the PCDH15 promoter comprises or consists of a nucleic acid sequence having at least about 85% (e.g., 90%, 95%, 97%, 98%, 99%) sequence identity to the following nucleotide sequence:

(SEQ ID NO: 7)
```
TCTTCACCTGTCATTTTCAACCAGCCTCAGCCTATCTGCTCTGTCACAA

TCACTACTAAAATATGTTCCTAAATTGCTTGTTTCTAGATCCTTCCTTC

TCATATGCTCAGGTGAACACATGGGTGAAATTTAATATGGAATTGAAAT

ATGTACTATGCAAGATAGATTCCTTAAGAAATGTTTCTCTGATTTATAT

GACATAATTGTATTTTACTAGTTTACCTGTCCATCTGTAAAACTTTGTT

TTGGAGATTTCATATATTACAATGTTTAAGAAATATGCTATAATGTTTT

GTATAGTATATTTCTTCGTGATAACCTTATATACTACCAGTCACACGTG

TTTGTAAAAATCTAAAGAGTACTTTTGGCTCCTACAGAATGTGTGAAGT

TGTGAAATTGTTTTTTTGTTTTGTTTTGTTTTGTTTTTATGCCCCAAAG

ATGTGGAGGGCTTCATATAAGAGGGTAGATTTAATGAGAGAGAGAGGGA

GAGACAGAGAGAATGATAAAAGAAGCTTAAGAGATTATTTTATCTTGTC

AACGACATTGTTATTGAATGTAAGCTGCTAAACTTCTTAGATAAAGTAA

AACAGTAAAAACAAACACACAAAACAGAACAGAGAATCATCAGACAGGC

TGACGAACACAGTACAATAAAGCAGCCAGTACCGATGATCAGTGGACAT
```

-continued

```
CAATTTGTCTTTTGGGCTGTAGCACCTGCTACTAATTGGTGCAAAGCGC

TCACCAGTCAGTGCGTGGTTTAGCGCACTCAGCTGTCTCCTGTATGTGC

TGCGAGAAGCAAGATAGCTAATTGCTGTTGCTTCAGTGCCAGTGAAATC

AACGTGCTGAGCTAATAGCGACAGATAGAGGGCAGACAGATTCCTGCTA

GCAGCTTAGTGTTAGTTGCTTGTGGTAACTAAGGCAGGTGGCATACATC

TCAGAACGTGGAGAATGATGGTATGCTTTCTGA
```

By "protein tyrosine phosphatase, receptor type Q (PT-PRQ) promoter" is meant a regulatory polynucleotide sequence derived from GeneID: 374462 that is sufficient to direct expression of a downstream polynucleotide in an outer or inner hair cell, vestibular hair cell, a spiral ganglion, or a vestibular ganglion. In one embodiment, the PTPRQ promoter comprises at least about 350 (e.g., 500, 1000, 2000, 3000, 4000, 5000), or more base pairs upstream of an PTPRQ coding sequence. In some embodiments, the PTPRQ promoter comprises or consists of a nucleic acid sequence having at least about 85% (e.g., 90%, 95%, 97%, 98%, 99%) sequence identity to the following nucleotide sequence:

```
                                        (SEQ ID NO: 8)
TGGTAGCCTCCCTAGAGACACAGAGCTGGGCCGGATGAGTCCAGGCACT

GACGTGATCCATTATCTTTCACCTTAAAGAGTAAAAGGGAAACTAAAGT

TAATTACCTCCACGAAACAAAAAGGTGCCTTCTTGTGCTTCAATTACAT

GGATATATTCTACTAGTCTAAAAGTATCTTCTCACTTCTTTCTGTCACT

GTGAGGACTTGAGTCAGAAGAAAGTTTAAATACAGTCATTGAGCTGGAA

AGAGTGGAAAGAGAAGCAAAGAGGGGGAAGCTGTAGGAAGGACGAAGTC

ACCCCCAAGATACATGGTTACTGCTTACACCAAGCAAGCTGCCTTGGGA

ACGCTTCCCCCGAGCAGCCAGAATGCTCAGCAGTGGAAGACACCTCTAT

TCCTGTAGGCGAGTCCTGGGAAGCTGGTCAATCTGCAAATGCCAATTCC

CAGCAGTGAGCTCGGTCCACGTGTAAATCAAGATTTGGGGAAAGAGTAG

GGTGGGTGGCATGGTTGACAATGTCATCAGCTCCCTCCTCTGACTCCTG

TGGTCGTGCCCCCATCTACTCTCACTCAGCTACACCCCACCTTCGGATT

TGTGATGGACGCTGGGTCCCTAGTAACCACAGCAAGTGTCTCCCCCGCA

CTTCCCCCTTCCCCACCCCCACCCCCACCCCCAACCACCACCCCAGCGA

TGGAGCCTACTCTGCTCCAAGCCGCCGCTAAGACCCGGAGAAGCGGAAT

TTCACTTTGAAATTCCCTTGCCTCGTGAGGGCCGGCGCTGGGCATGCTC

AGTAGCCGCGGCGCTGCTGCTGGGCTGCTGGGCTGGCGCGGAGTCCACC

CTGCCGTCTCCGCCTTGGCTTCTGGGCGTCCAGAAGGCCAGGCATTTGC

CGCCTCTGAGCGCTTCTGTTCCCCTTACCCGCAACCTCCTACTGCTCTT

CCTCTCTCCCTCTCTTAGGGAGGTTGAAGCTGGTGCTGGTTTCTGTCGG

CGCCACAGACTGACTGCTCTGCAAACCCCAGCCGAGGACCTGAATCCCG

GAGACTAGAAG
```

By "lipoma HMGIC fusion partner-like 5 (LHFPL5) promoter" also termed "TMHS promoter" is meant a regulatory polynucleotide sequence derived from NCBI Reference Sequence: GeneID: 222662 that is sufficient to direct expression of a downstream polynucleotide in an outer or inner hair cell, vestibular hair cell, a spiral ganglion, or a vestibular ganglion. In one embodiment, the TMHS promoter comprises at least about 350 base pairs (e.g., 500, 1000, 2000, 3000, 4000, 5000), or more base pairs upstream of an PCDH15 coding sequence. In some embodiments, the TMHS promoter comprises or consists of a nucleic acid sequence having at least about 85% (90%, 95%, 97%, 98%, 99%) sequence identity to the following nucleotide sequence:

```
                                        (SEQ ID NO: 9)
GCCCAGTGGAATTTTCCTAGTTCTTTACACTAGCCATGTATTTACCTAT

AAAATCAGGAGAAATATGTATATATATAATATATTAAAACATATATATA

TTTAAATGGGAAATATGTAACAAACAAATAGAAACAAGGGGAGAAAGG

CATTGTATTTGACAAAACACATATGTTCAGGTCTGAGAAGGCTCATAAA

GAATGTTGTCTGCTATACTTTGTAGTTGCTTCTGTTATCACACAATCAG

TCTGCATATACAGGCGTTTTATATATATATTTATATAGACTACATATAT

ACGTATATTATATATGTAAATATTTCACTGTCTTTGAGGACGGGGGCCC

TGTCTTTTTTATCTGTGGTTTTGCTTAGATGTCCTCCAACATAATCTTA

ACACATAGTATGCTTTTAGAAATCGTTGACTGAATGCTAAGGACGAAAA

ACCGGTGACCAGAAGGCAACCAGGAAAGGCTTTGCTGACCTCCGGAGTG

GTGGAGTTGGAGGTTCTGGGAAGGCGACTAGGGAGCCAGGCAGGGGCGG

GGTGGGATGGGATGTGGACAGCGCTTTTGCGGGGGGAAAGCGTTTTTGC

TGCTGGAATTGAGCAGTAGGAATGTGTCAGTCACATCCCCACCTTCCCA

ATTCTTGTCATCTCGGTTCAGGAAGGTGAACGGTGTTCCGATTCCCCGC

GGCGGGGGCCTGTAGTGGGAGCTCTGCCCCTTCCCCGCCTCTGCTGCAG

GCCCCGCCCCTCGCCCGGAACCCCGGGGCGCTGGCCGCGGTGCTGAAAC

GGCGCCCTCCGCGGACGGAGGAGGGGGCGGGGCTCTCGGGAGCCGTGAG

CCGGGAAGAGGGAGACGGGCAGGGCGGCGCCAGCAGGCCCTGGTGGGCT

TGGGAGGAGGCAGGAGACTGGAGACAGCCTCGGCTAGAGCGGACACAGG

CACCTGGCAAGCTTTCCTTGACCAAATCAAGGT.
```

By "synapsin promoter" also termed "Syn promoter" is meant a regulatory polynucleotide sequence comprising or consisting of a nucleic acid sequence sufficient to direct expression of a downstream polynucleotide in an outer or inner hair cell, a vestibular hair cell, a spiral ganglion, or a vestibular ganglion and having at least about 85% (90%, 95%, 97%, 98%, 99%) sequence identity to the following nucleotide sequence:

```
                                        (SEQ ID NO: 10)
TCTAGACTGCAGAGGGCCCTGCGTATGAGTGCAAGTGGGTTTTAGGACC

AGGATGAGGCGGGGTGGGGGTGCCTACCTGACGACCGACCCCGACCCAC

TGGACAAGCACCCAACCCCCATTCCCCAAATTGCGCATCCCCTATCAGA

GAGGGGGAGGGGAAACAGGATGCGGCGAGGCGCGTGCGCACTGCCAGCT

TCAGCACCGCGGACAGTGCCTTCGCCCCCGCCTGGCGGCGCGCGCCACC

GCCGCCTCAGCACTGAAGGCGCGCTGACGTCACTCGCCGGTCCCCCGCA

AACTCCCCTTCCCGGCCACCTTGGTCGCGTCCGCGCCGCCGCCGGCCCA
```

-continued

GCCGGACCGCACCACGCGAGGCGCGAGATAGGGGGGCACGGGCGCGACC

ATCTGCGCTGCGGCGCCGGCGACTCAGCGCTGCCTCAGTCTGCGGTGGG

CAGCGGAGGAGTCGTGTCGTGCCTGAGAGCGCAGTC.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, at least about 20 amino acids, at least about 25 amino acids, and in some embodiments, at least about 35 amino acids, about 50 amino acids, or about 100 amino acids. For nucleic acids, the length of the reference nucleic acid sequence will generally be at least about 50 nucleotides, at least about 60 nucleotides, at least about 75 nucleotides, and at least about 100 nucleotides or about 300 nucleotides or any integer thereabout or therebetween.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, less than about 500 mM NaCl and 50 mM trisodium citrate, or less than about 250 mM NaCl and 25 mM trisodium citrate. Low stringency hybridization can be obtained in the absence of organic solvent, e.g., formamide, while high stringency hybridization can be obtained in the presence of at least about 35% formamide, or at least about 50% formamide. Stringent temperature conditions will ordinarily include temperatures of at least about 30° C., at least about 37° C., or at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In an embodiment, hybridization will occur at 30° C. in 750 mM NaCl, 75 mM trisodium citrate, and 1% SDS. In another embodiment, hybridization will occur at 37° C. in 500 mM NaCl, 50 mM trisodium citrate, 1% SDS, 35% formamide, and 100 μg/ml denatured salmon sperm DNA (ssDNA). In yet a further embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will, in some instances, be less than about 30 mM NaCl and 3 mM trisodium citrate, or less than about 15 mM NaCl and 1.5 mM trisodium citrate. Stringent temperature conditions for the wash steps will ordinarily include a temperature of at least about 25° C. (e.g., at least about 42° C., at least about 68° C.). In one embodiment, wash steps will occur at 25° C. in 30 mM NaCl, 3 mM trisodium citrate, and 0.1% SDS. In another embodiment, wash steps will occur at 42 C in 15 mM NaCl, 1.5 mM trisodium citrate, and 0.1% SDS. In yet a further embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). In some embodiments, such a sequence is at least 60% (e.g., 80%, 85%, 90%, 95%, 99%) identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-100 indicating a closely related sequence.

By "subject" is meant any organism to which a composition and/or compound in accordance with the disclosure may be administered, e.g., for experimental, diagnostic, prophylactic, and/or therapeutic purposes. Generally, subjects may include any animal (e.g., a mammal, including, but not limited to, a human or non-human mammal, such as a rodent, primate, bovine, equine, canine, ovine, or feline. A "subject in need thereof" is typically a subject for whom it is desirable to treat a disease as described herein. For example, a subject in need thereof may seek or be in need of treatment, require treatment, be receiving treatment, may be receiving treatment in the future, or a human or non-human animal that is under care by a trained professional for a particular disease.

By "TMC1 polypeptide" is meant a Transmembrane Channel-Like 1 polypeptide having at least about 85% or greater (e.g., 90%, 95%, 97%, 98%, 99%) amino acid sequence identity to NCBI Reference Sequence: NP_619636.2 or a fragment thereof having mechanotransduction channel activity. An exemplary amino acid sequence of TMC1 is provided below:

```
                                                           (SEQ ID NO: 11)
    1   MSPKKVQIKV EEKEDETEES SSEEEEEVED KLPRRESLRP KRKRTRDVIN EDDPEPEPED

61   EETRKAREKE RRRRLKRGAE EEEIDEEELE RLKAELDEKR QIIATVKCKP WKMEKKIEVL

121   KEAKKFVSEN EGALGKGKGK RWFAFKMMMA KKWAKFLRDF ENFKAACVPW ENKIKAIESQ

181   FGSSVASYFL FLRWMYGVNM VLFILTFSLI MLPEYLWGLP YGSLPRKTVP RAEEASAANF

241   GVLYDFNGLA QYSVLFYGYY DNKRTIGWMN FRLPLSYFLV GIMCIGYSFL VVLKAMTKNI

301   GDDGGGDDNT FNFSWKVFTS WDYLIGNPET ADNKFNSITM NFKEAITEEK AAQVEENVHL

361   IRFLRFLANF FVFLTLGGSG YLIFWAVKRS QEFAQQDPDT LGWWEKNEMN MVMSLLGMFC

421   PTLFDLFAEL EDYHPLIALK WLLGRIFALL LGNLYVFILA LMDEINNKIE EEKLVKANIT

481   LWEANMIKAY NASFSENSTG PPFFVHPADV PRGPCWETMV GQEFVRLTVS DVLTTYVTIL

541   IGDFLRACFV RFCNYCWCWD LEYGYPSYTE FDISGNVLAL IFNQGMIWMG SFFAPSLPGI

601   NILRLHTSMY FQCWAVMCCN VPEARVFKAS RSNNFYLGML LLILFLSTMP VLYMIVSLPP

661   SFDCGPFSGK NRMFEVIGET LEHDFPSWMA KILRQLSNPG LVIAVILVMV LAIYYLNATA

721   KGQKAANLDL KKKMKMOALE NKMRNKKMAA ARAAAAAGRQ.
```

By "TMC1 polynucleotide" is meant a polynucleotide encoding a TMC1 polypeptide. The sequence of an exemplary TMC1 polynucleotide is provided at NCBI Reference Sequence: NM_138691.2, which is reproduced below:

```
                                                           (SEQ ID NO: 12)
    1   CAGAAACTAT GAGGGCAGAA CCCAGCAATC TGTGCTTTCT TTCACAAGCC CTCCAGGAGT

61   TGCTGAAATT TAGGAATCAT TGCCCCAAAA AGTGGCCCTC ATAATGATGC CAGATGGGAT

121   CTTACTCTGT TGCCCAGGCT GGAGTGCAGT GGTGCGATCT CGGCTCTCTG CAACCTCCGC

181   CTCCCAGGTT CAAGTGATTC TCCTGCCTCG GCCTCCTGAG TAGCTGGGAT TTCAGGCCAT

241   GAAAGATCAC TGTTTTAGTC TGCGTGGTGC AGTGGAACAG ATAGACCTCG GTTTGAATCT

301   CAGCTCTACT GTTTACTAGA CATGAAATGG GGAAATCTAA AATGAGATGC CAGAAGCCTC

361   AAAAATGGAA AACCCCCTGT GCTTCACATC TGAAAATCTC TGCTGGGGGC AGCAACTTTG

421   AGCCTGTGGG GAAGGAACTG TCCACGTGGA GTGGTCTGGT GAATGCTTAA GGAGCTGCAG

481   AAGGGAAGTC CCTCTCCAAA CTAGCCAGCC ACTGAGACCT TCTGACAGGA CACCCCCAGG

541   ATGTCACCCA AAAAGTACA AATCAAAGTG GAGGAAAAAG AAGACGAGAC TGAGGAAAGC

601   TCAAGTGAAG AGGAAGAGGA GGTGGAAGAT AAGCTACCTC GAAGAGAGAG CTTGAGACCA

661   AAGAGGAAAC GGACCAGAGA TGTTATCAAT GAGGATGACC CAGAACCTGA ACCAGAGGAT

721   GAAGAAACAA GGAAGGCAAG AGAAAAAGAG AGGAGGAGGA GGCTAAAGAG AGGAGCAGAA

781   GAAGAAGAAA TTGATGAAGA GGAATTGGAA AGATTGAAGG CAGAGTTAGA TGAGAAAAGA

841   CAAATAATTG CTACTGTCAA ATGCAAACCA TGGAAGATGG AGAAGAAAAT TGAAGTTCTC

901   AAGGAGGCAA AAAAATTTGT GAGTGAAAAT GAAGGGGCTC TTGGGAAAGG AAAAGGAAAA

961   CGGTGGTTTG CATTTAAGAT GATGATGGCC AAGAAATGGG CAAAATTCCT CCGTGATTTT

1021   GAGAACTTCA AAGCTGCGTG TGTCCCATGG GAAAATAAAA TCAAGGCTAT TGAAAGTCAG
```

```
                                 -continued
1081   TTTGGCTCCT CAGTGGCCTC ATACTTCCTC TTCTTGAGAT GGATGTATGG AGTCAATATG

1141   GTTCTCTTTA TCCTGACATT TAGCCTCATC ATGTTGCCAG AGTACCTCTG GGGTTTGCCA

1201   TATGGCAGTT TACCTAGGAA AACCGTTCCC AGAGCCGAAG AGGCATCGGC AGCAAACTTT

1261   GGTGTGTTGT ACGACTTCAA TGGTTTGGCA CAATATTCCG TTCTCTTTTA TGGCTATTAT

1321   GACAATAAAC GAACAATTGG ATGGATGAAT TTCAGGTTGC CGCTCTCCTA TTTTCTAGTG

1381   GGGATTATGT GCATTGGATA CAGCTTTCTG GTTGTCCTCA AAGCAATGAC CAAAAACATT

1441   GGTGATGATG GAGGTGGAGA TGACAACACT TTCAATTTCA GCTGGAAGGT CTTTACCAGC

1501   TGGGACTACC TGATCGGCAA TCCTGAAACA GCAGACAACA AATTTAATTC TATCACAATG

1561   AACTTTAAGG AAGCTATCAC AGAAGAAAAA GCAGCCCAAG TAGAAGAAAA CGTCCACTTG

1621   ATCAGATTCC TGAGGTTTCT GGCTAACTTC TTCGTGTTTC TAACACTTGG AGGGAGTGGA

1681   TACCTCATCT TTTGGGCTGT GAAGCGATCC CAGGAATTTG CACAGCAAGA TCCTGACACC

1741   CTTGGGTGGT GGGAAAAAAA TGAAATGAAC ATGGTTATGT CCCTCCTAGG GATGTTCTGT

1801   CGAACATTGT TTGACTTATT TGCTGAATTA GAAGACTACC ATCCTCTCAT CGCTTTGAAA

1861   TGGCTACTGG GACGCATTTT TGCTCTTCTT TTAGGCAATT TATACGTATT TATTCTTGCA

1921   TTAATGGATG AGATTAACAA CAAGATTGAA GAGGAGAAGC TAGTAAAGGC CAATATTACC

1981   CTTTGGGAAG CCAATATGAT CAAGGCCTAC AATGCATCAT TCTCTGAAAA TAGCACTGGA

2041   CCACCCTTTT TTGTTCACCC TGCAGATGTA CCTCGAGGAC CTTGCTGGGA AACAATGGTG

2101   GGACAGGAGT TTGTGAGGCT GACAGTCTCT GATGTTCTGA CCACCTACGT CACAATCCTC

2161   ATTGGGGACT TTCTAAGGGC ATGTTTTGTG AGGTTTTGCA ATTATTGCTG GTGCTGGGAC

2221   TTGGAGTATG GATATCCTTC ATACACCGAA TTCGACATCA GTGGCAACGT CCTCGCTCTG

2281   ATCTTCAACC AAGGCATGAT CTGGATGGGC TCCTTCTTTG CTCCCAGCCT CCCAGGCATC

2341   AATATCCTTC GACTCCATAC ATCCATGTAC TTCCAGTGCT GGGCCGTTAT GTGCTGCAAT

2401   GTTCCTGAGG CCAGGGTCTT CAAAGCTTCC AGATCAAATA ACTTCTACCT GGGCATGCTA

2461   CTGCTCATCC TCTTCCTGTC CACAATGCCT GTCTTGTACA TGATCGTGTC CCTCCCACCA

2521   TCTTTTGATT GTGGTCCATT CAGTGGCAAA AATAGAATGT TTGAAGTCAT TGGAGAGACC

2581   CTGGAGCACG ATTTCCCAAG CTGGATGGCG AAGATCTTGA GACAGCTTTC AAACCCTGGG

2641   CTGGTCATTG CTGTCATTTT GGTGATGGTT TTGGCCATCT ATTATCTCAA TGCTACTGCC

2701   AAGGGCCAGA AGGCAGCGAA TCTGGATCTC AAAAAGAAGA TGAAAATGCA AGCTTTGGAG

2761   AACAAAATGC GAAACAAGAA AATGGCAGCT GCACGAGCAG CTGCAGCTGC TGGTCGCCAG

2821   TAATAAGTAT CCTGAGAGCC CAGAAAAGGT ACACTTTGCC TTGCTGTTTA AAAGTAATGC

2881   AATATGTGAA CGCCCAGAGA ACAAGCACTG TGGAACTGCT ATTTTCCTGT TCTACCCTTG

2941   ATGGATTTTC AAGGTCATGC TGGCCAATTA AGGCATCATC AGTCCTACCT GAGCAACAAG

3001   AATCTAAACT TTATTCCAAG TCAGAAACTG TTTCTGCAGA GCCACTCTCT CCCCTGCTCC

3061   ATTTCGTGAC TTTTTTTTTT TTTTTAACAA ATTGAGTTTA GAAGTGAGTG TAATCCAGCA

3121   ATACAGTTTA CTGGTTTAGT TGGTGGGTTA ATTAAAAAAA ATTTGCTCAT ATGAACTTTC

3181   ATTTTATATG TTTCTTTTGC C.
```

As used herein, the terms "treat," "treating," "treatment," and the like refer to reducing or ameliorating a disease (including a disorder or condition) and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 5B illustrates a design of gRNA sequences targeting the Bth mutation. Aligned sequences of the mouse Tmc1 and human TMC1 genes are shown in the lower boxes. The protospacer adjacent motif (PAM) sequence is depicted in underlined blue text, the nucleotide corresponding to the Bth mutation in red (* over T nucleotides of gRNA 11-20; A nucleotide of gRNA 21-22), and green # over the G nucleotides of gRNA 16 and gRNA 22 from the WT. FIG. 5B discloses SEQ ID NOS 14-31, respectively, in order of appearance.

FIG. 5C discloses SEQ ID NOS 32-34, respectively, in order of appearance.

Figure 6:
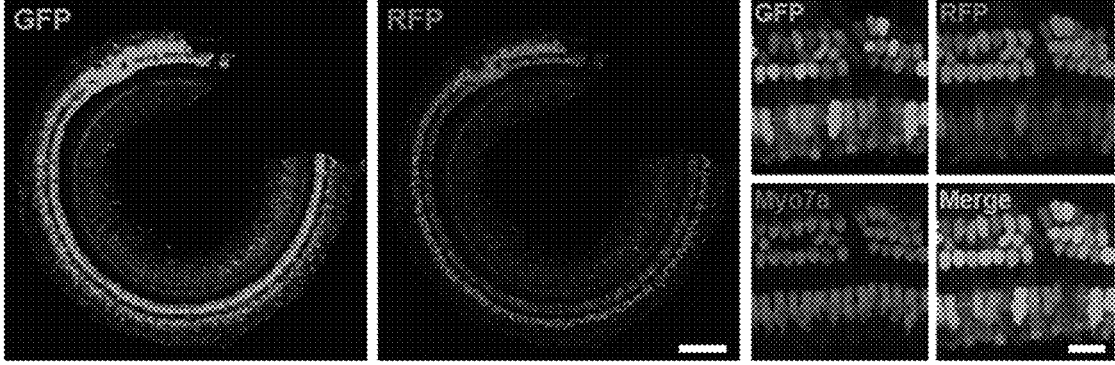
FIG. 6 presents representative 10× confocal images (left and middle images) from apical-mid cochlear sections showing GFP (green) and RFP (red) co-expression in inner and outer hair cells. Magnification (63×) of 100 m sections (right images) illustrate GFP and RFP expression in individual hair cells, merged, and stained against MyoVIIa (blue). Scale bars 100 m at 10× and 20 m at 63×.
Figure 7A:
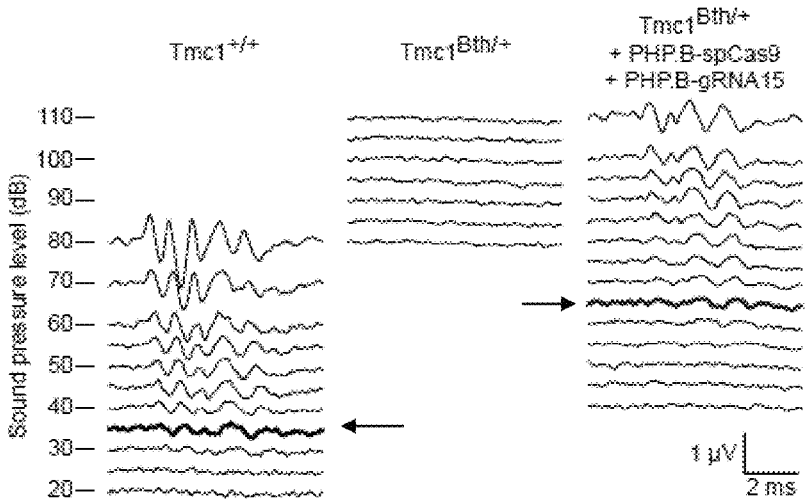
FIG. 7A provides representative ABR waveform families recorded from mice at 24 weeks for indicated conditions, using 11.3-kHz tone bursts at incrementally increasing sound pressure levels. Thresholds were determined by the presence of peak 1 and is indicated by colored traces pointed to by arrows. Scale bar applies to all families.
Figure 7B:
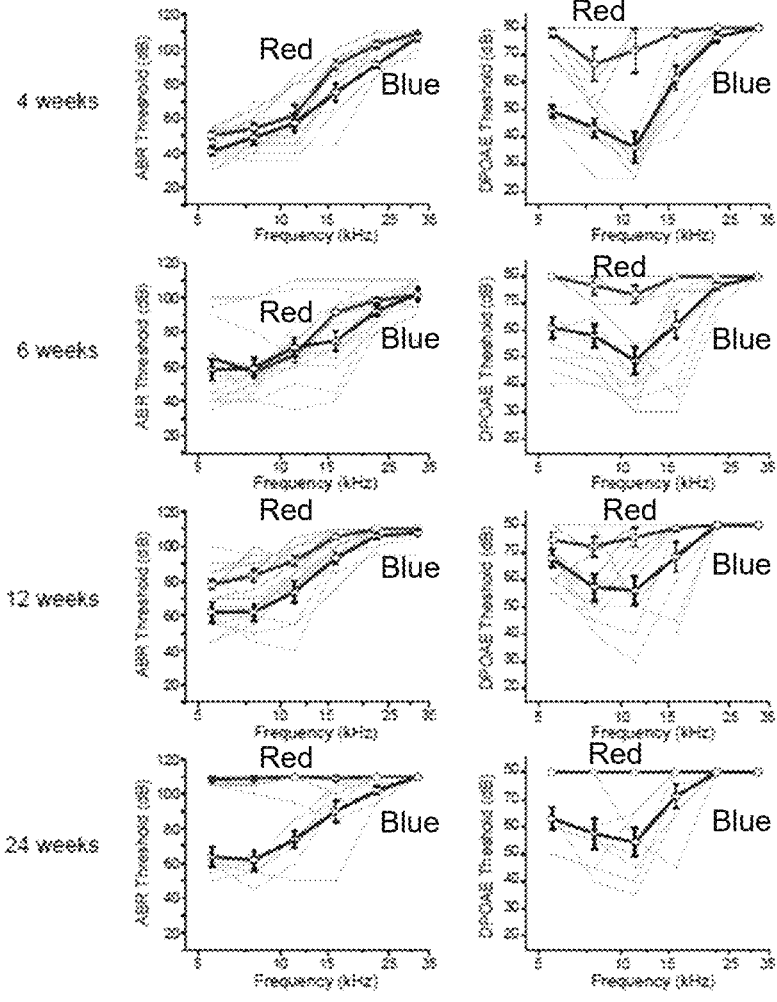
FIG. 7B shows mean ABR (left) and DPOAE (right) thresholds mice plotted as a function of stimulus frequency for TMC1$^{Bth/+}$ un-injected controls (bold line beneath "Red", n=6 at four weeks, n=3 at six weeks, n=9 at twelve weeks, n=9 at twenty four weeks old) and TMC1$^{Bth/+}$ mice dual injected with AAV9-PHP.B-spCas9 and AAV9-PHP.B-gRNA15 (bold line above "Blue", n=9 at four weeks, n=13 at six weeks, n=9 at twelve weeks, n=8 at twenty four weeks old). Lighter traces show individual responses. Error bars are SEM.
Figure 7C:
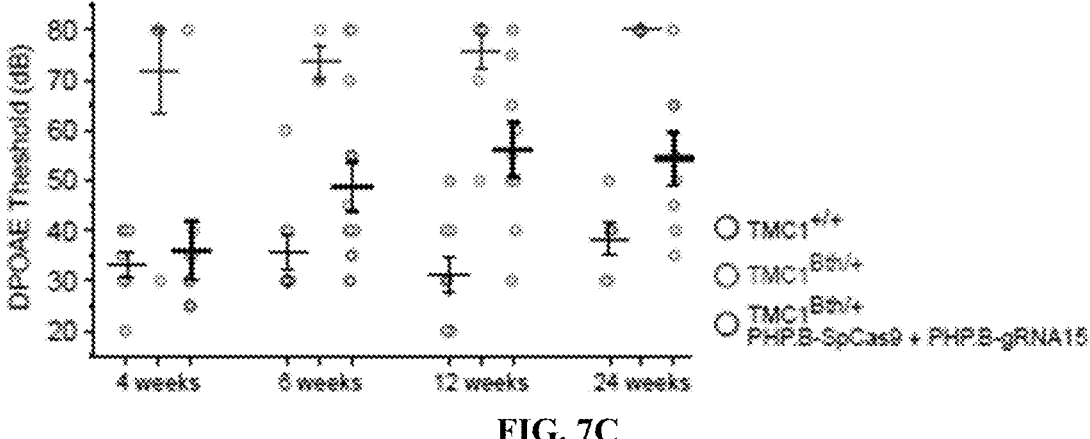

FIG. 7C illustrates DPOAE thresholds at 11.3 kHz measured in (FIG. 6B) plotted as a function of age from 4, 6, 12 and 24 weeks. For each timepoint of 4, 6, 12 and 24 weeks, WT or TMC1$^{+/+}$, n=8, 9, 9, 6 (Left); TMC1$^{Bth/+}$, n=6, 3, 9, 9 (Center); Dual injection with AAV-PHP.B-SpCas9 and AAV9-PHP.B-gRNA15, n=9, 13, 9, 8 (Right)). Error bars are SEM.

Figure 8A:
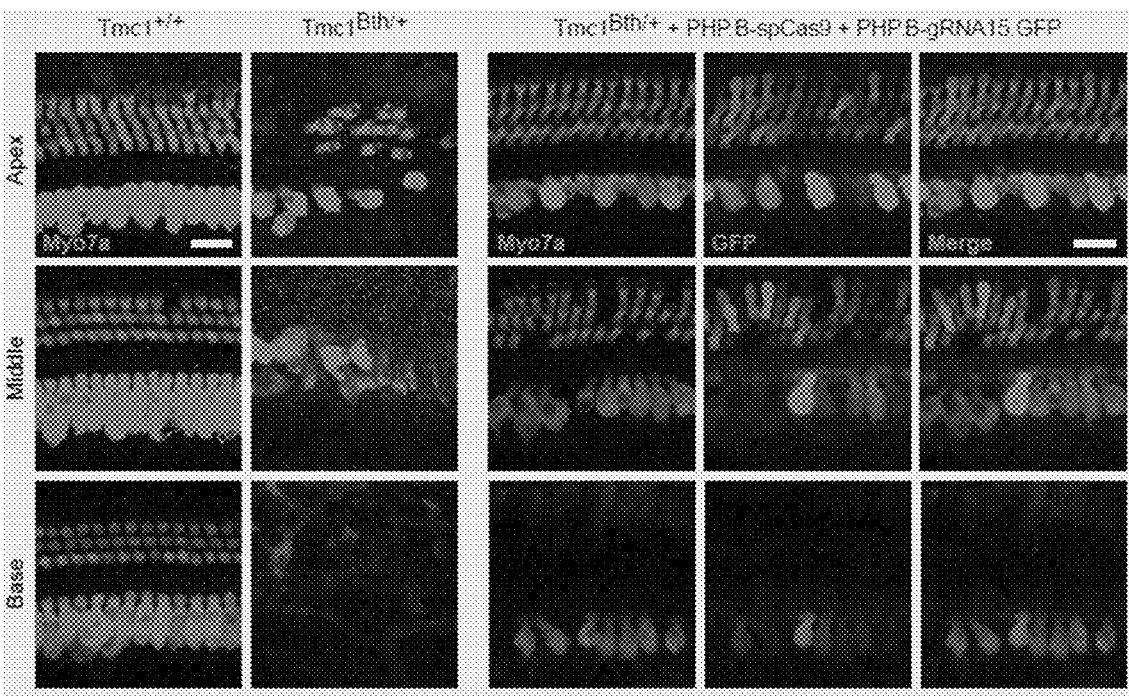

FIG. 8A shows representative 63× confocal images of 100 μm sections from the apex, middle, and basal cochlear turns of TMC1$^{+/+}$ wild-type C57BL/6 and un-injected TMC1$^{Bth/+}$ mice (left two columns) or TMC1$^{Bth/+}$ mice dual injected with PHP.B-spCas9 and PHP.B-gRNA15.GFP (green) immunostained against MyoVIIa (red) at 24 weeks of age (right three columns). Scale bar is 20 μm.

Figure 8B:
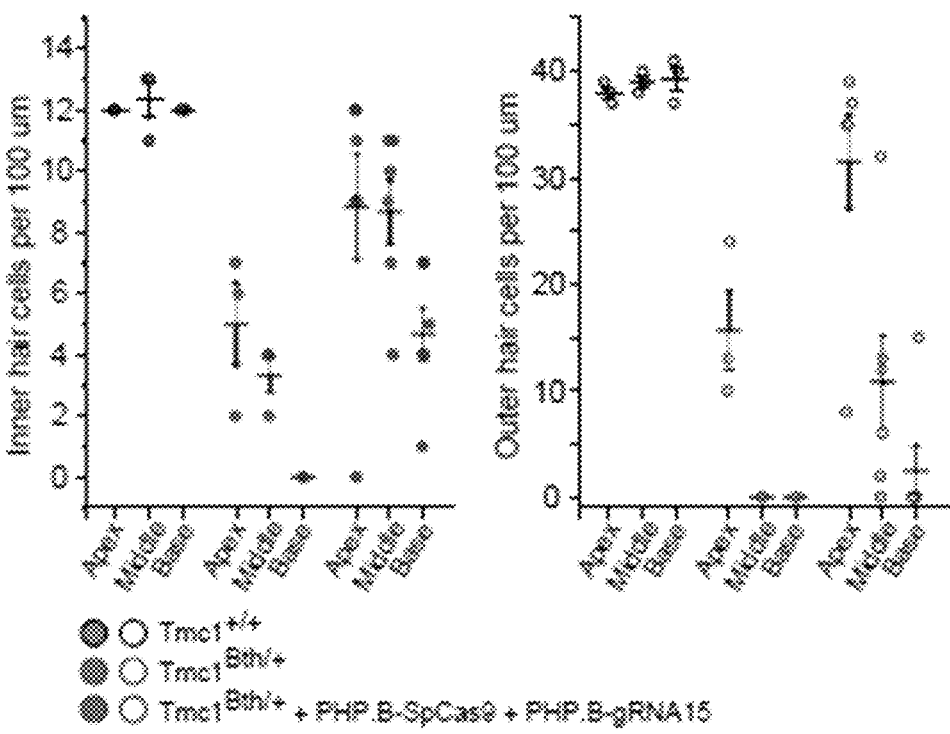

FIG. 8B provides mean cell counts of inner (left panel) and outer (right panel) hair cells for wild-type C57BL/6 (TMC1$^{+/+}$)(n=3) (Left grouping), TMC1Bth/+ un-injected controls (n=3) (Center grouping), and TMC1Bth/+ mice dual injected with PHP.B-spCas9 and PHP.B-gRNA15.GFP (n=6) (Right grouping) at 24 weeks of age measured from 100 μm sections of the apex, middle, and basal cochlear turns. Individual samples are shown as scatter plot.

Figure 8C:
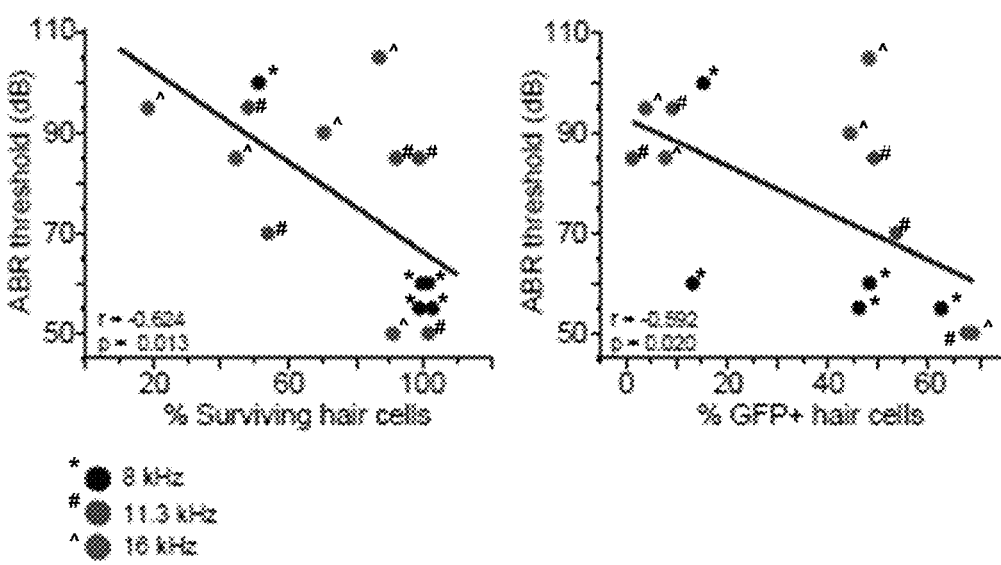

FIG. 8C presents the ABR threshold (dB) as compared to the percentage of surviving hair cells (left panel) and the percentage of Green Fluorescent Protein (GFP) stained hair cells (right panel) at varying kilohertz (kHz).

Figure 9A:
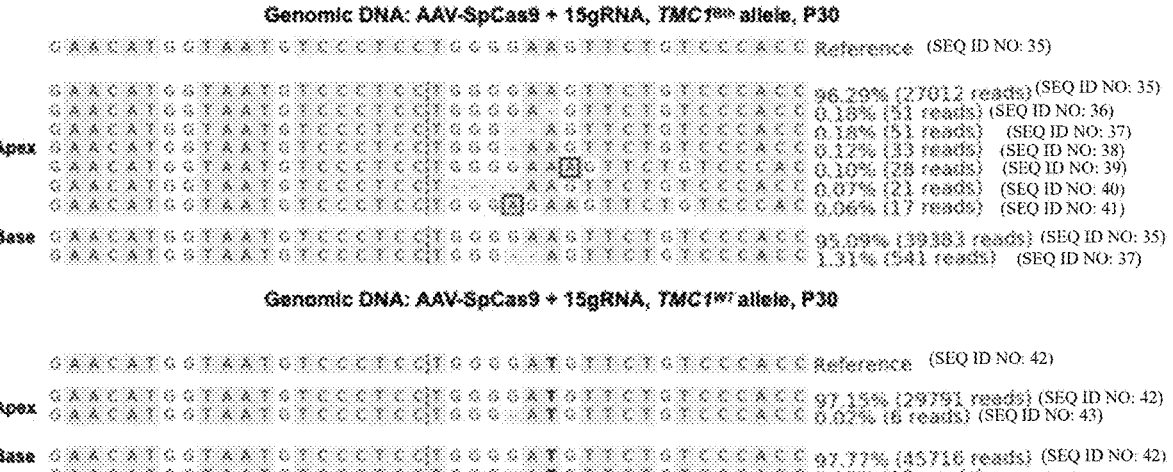

FIG. 9A shows the edited reads in an AAV9-PHP.B-SpCas9+AAV9-PHP.B-gRNA15 injected Tmc1$^{Bth/+}$ mouse from the apical and basal halves of the cochlea. Reads are shown separately for Bth and WT alleles. Figure discloses SEQ ID NOS 35, 35-41, 35, 37, 42, 42-43, and 42-43, respectively, in order of appearance.

Figure 9B:
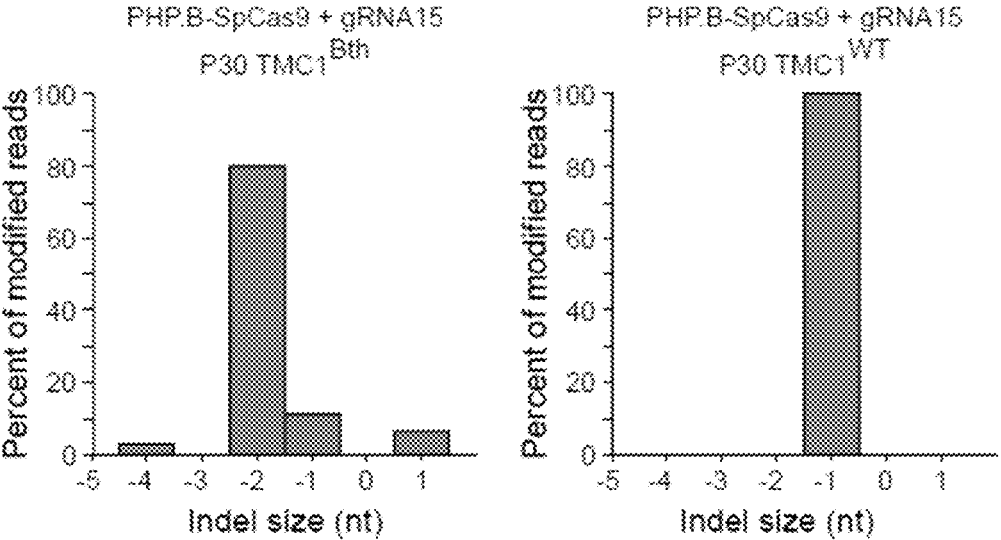

FIG. 9B presents a representative indel profile from an AAV9-PHP.B-SpCas9+AAV9-PHP.B-gRNA15 injected Tmc1$^{Bth/+}$ mouse on the Bth (Left panel) and WT (Right panel) allele. Minus numbers represent nucleotide deletions, positive numbers are insertions, no indels have a value of 0.

DETAILED DESCRIPTION OF THE INVENTION

As described below, the present invention features a dual vector system for disrupting and replacing a target gene comprising a mutation.

The invention is based, at least in part, on the discovery that administration of a dual vector system comprising a first vector ("disrupting vector") encoding a Cas9 protein (e.g., SaCas9-KKH, SpCas9-KKH) and a second vector ("replacing vector") encoding a wild-type gene that replaces a mutant target gene and a guide RNA (gRNA) that directs the Cas9 protein to the target gene. Importantly, Cas9-mediated gene editing does not occur in the absence of a gRNA. Because the first vector encodes the Cas9 protein, it is not sufficient to disrupt the endogenous target gene. Only when the first vector and the second vector (i.e., containing the gRNA and the wild-type replacement gene) are present together in a cell will gene editing occur. This eliminates the possibility of a Cas9 protein inactivating a gene when a replacement gene is not present.

Dual Vector System

Figure 1:
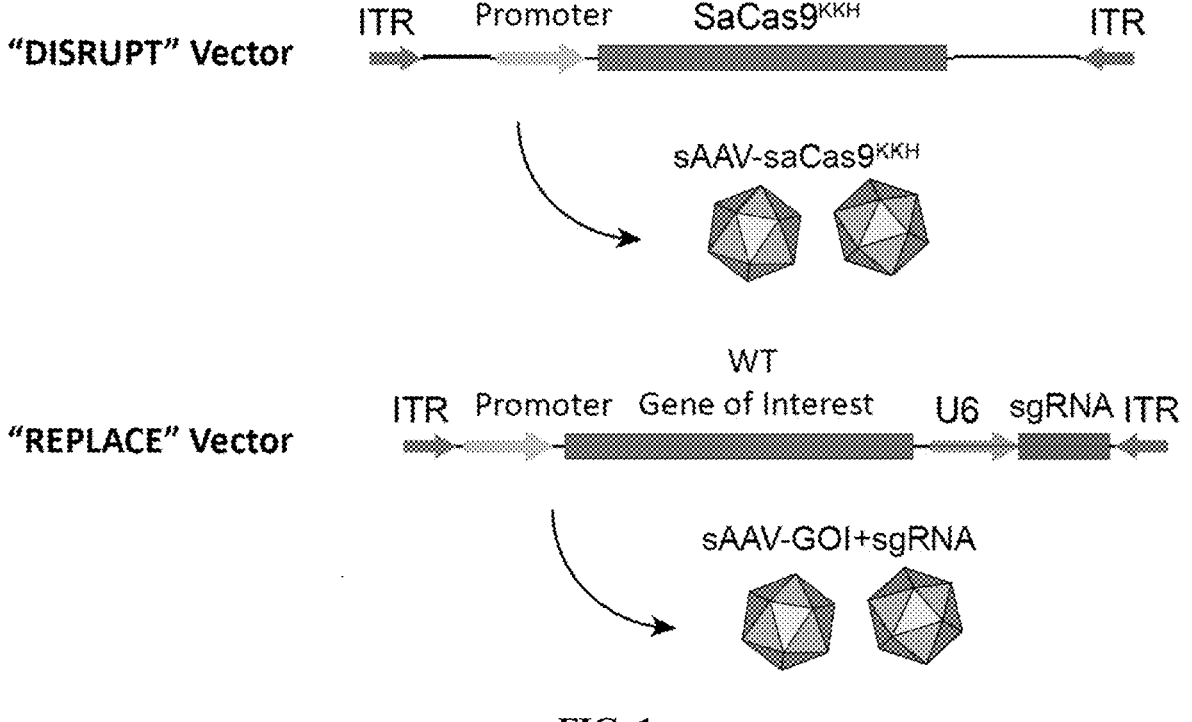
FIG. 1 is a schematic of a dual vector gene editing and replacement system. Shown are two vectors, a first vector encoding a the SaCas9-KKH nuclease and a second vector encoding a wild type (WT) gene of interest. This second vector also encodes U6 promoter that drives expression of a single guide RNA (sgRNA). Inverted tandem repeats (ITRs) are at the termini of both vectors.
Figure 2:
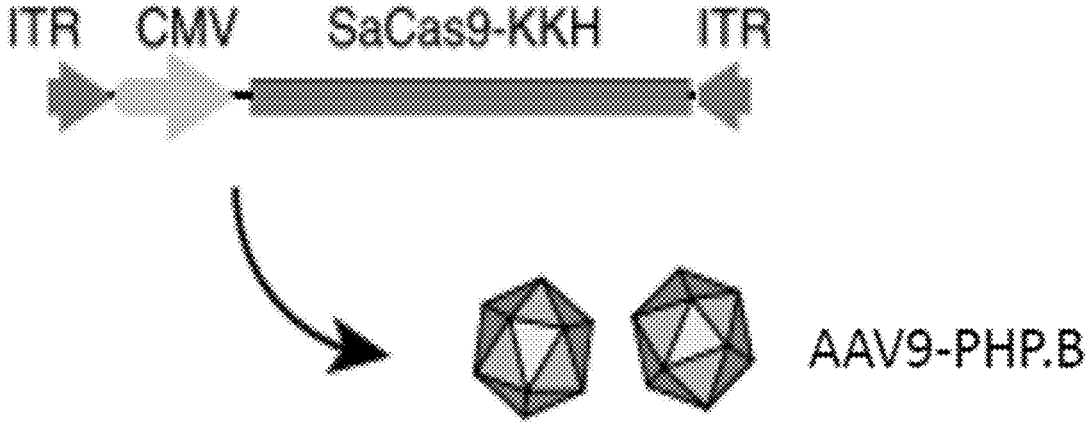
FIG. 2 provides an exemplary schematic of the dual vector gene editing and replacement system. Vector 1 carries a CMV promoter and the coding sequence for SaCas9-KKH. Vector 2 carries a CMV promoter driving the WT TMC1 sequence with a mutation that does not affect the amino acid sequence and is not recognized by the SaCas9-KKH coding sequence. Vector 2 also contains the U6 promoter and guide RNA sequence that recognizes WT and mutant TMC1 alleles. Both vectors are packaged into AAV9-PHP.B.
Figure 2:
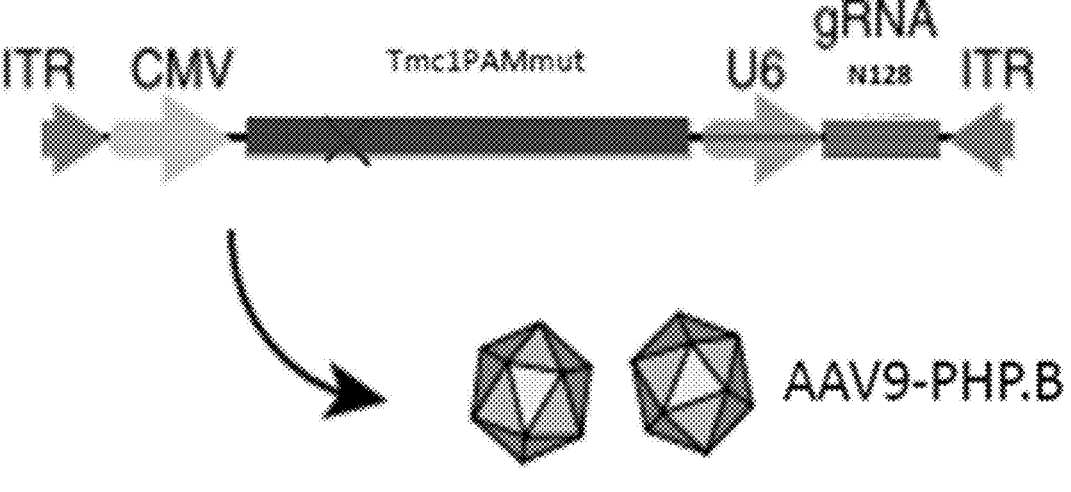

The invention provides a dual vector system for gene editing comprising a first vector encoding a Cas9 polypeptide, such as an SaCas9-KKH or SpCas9-KKH polypeptide, or a fragment thereof, that disrupts a target gene; and a second vector that encodes a guide RNA (gRNA) and a wild-type version of the target gene that replaces the disrupted target gene (FIGS. 1-2). Advantageously, the presence of both vectors in a single cell is required for activity.

Cas9

Cas9 proteins are known in the art, such as *Streptococcus pyogenes* Cas9 (SpCas9), *Staphylococcus aureus* Cas9 (SaCas9), and *Francisella novicida* Cas9 (FnCas9). Cas9 is a nuclease, an enzyme specialized for cutting DNA, with two active cutting sites, one for each strand of the double helix. In general, Cas9 proteins preferentially interrogate and act upon DNA sequences containing a protospacer adjacent motif (PAM) sequence, and different Cas9 proteins have affinities for different PAMs. The canonical PAM sequence is 5'-NGG-3', which is recognized by multiple Cas9 proteins, where N can be any nucleotide. For example, SpCas9 and FnCas9 recognize the canonical NGG PAM sequence. *Streptococcus thermophilus* Cas9 recognizes a 5'-NGA-3' PAM sequence, and SaCas9 recognizes a 5'-NNGRR(N)-3' PAM sequence. Additionally, Cas9 proteins can be modified to recognize PAM sequences that are distinct from the PAM sequences recognized by the unmodified Cas9 protein. For example, SaCas9-KKH recognizes a 5'-RRT-3', where R denotes an adenosine or guanine nucleotide.

To effectively direct a Cas9 polypeptide to a target nucleic acid that contains a PAM sequence, a guide RNA can be designed that has a sequence complementary to a nucleic acid sequence in the target nucleic acid molecule. It has been proposed that such synthetic guide RNAs might be able to be used for gene editing (Jinek et al., Science. 2012 Aug. 17; 337(6096):816-21).

Guide RNA (gRNA)

A Cas9 protein, having an affinity for a particular PAM sequence can be directed to a particular locus in a genome by a guide RNA (gRNA). In some embodiments, the guide RNA is a "single guide RNA" (sgRNA) which comprises a trans-activating CRISPR RNA (crRNA) (tracrRNA) and a spacer RNA, where the guide RNA can bind to both the Cas9 protein and the target DNA sequence. The tracrRNA provides a scaffold that can interact with a Cas9 protein. The short spacer RNA, comprising a nucleic acid sequence that specifically binds to the target genomic locus, directs the Cas9 protein to the target, which is then cleaved by the Cas9 protein's nuclease activity. In some embodiments, synthetic gRNAs are about 18 basepairs (bp) or greater (e.g., 19, 20, 21, 22, 23, 24, 25, 30, 40, 50, 60, 70, 80, 90, 100, over 100 bp) and comprise a nucleic acid sequence complementary to protospacer nucleotides near the PAM sequence A spacer RNA, tracrRNA, or sgRNA can comprise a nucleotide analog or other modification.

In some embodiments, the modification can be a nucleotide analog that is lacking the 3' OH group on the ribose sugar. Nucleotide analogs are known in the art. Additionally, the RNA molecule may comprise a modified backbone. For example, rather than having the canonical sugar-phosphate backbone of a naturally occurring RNA molecule, the molecule may have a sugar thiophosphate backbone. In some embodiments, incorporating a modified nucleotide, nucleotide analog, or modified backbone (and like modifications) can decrease a guide RNA's susceptibility to degradation.

In some embodiments, the guide RNA will bind a nucleic acid sequence comprising a PAM sequence that is present in one or more alleles. In some embodiments, the guide RNA binds a nucleic acid sequence that is in close proximity to a PAM sequence. For example, the PAM sequence may be 1 or greater (e.g., 2, 3, 4, 5, 6, 7, 8, 9, 10) nucleotides upstream or downstream of the sequence to which the guide RNA binds. In some embodiments, the PAM sequence may be 1-10 nucleotides upstream or downstream of the sequence to which the guide RNA binds. For example, Cas9 recognizes the 5'-NGG-3' PAM (SpCas9). Liu et al. Comput Struct Biotechnol J. 18:35-44, 2020, which is incorporated here by reference in its entirety, is a review providing guide RNA design considerations, parameters, and tools.

The following U.S. patents and patent publications are incorporated herein by reference in their entireties for their disclosure regarding gene editing, including but not limited to disrupting vectors, replacement vectors, and methods thereof: U.S. Pat. No. 8,697,359, 20140170753, 20140179006, 20140179770, 20140186843, 20140186958, 20140189896, 20140227787, 20140242664, 20140248702, 20140256046, 20140273230, 20140273233, 20140273234, 20140295556, 20140295557, 20140310830, 20140356956, 20140356959, 20140357530, 20150020223, 20150031132, 20150031133, 20150031134, 20150044191, 20150044192, 20150045546, 20150050699, 20150056705, 20150071898, 20150071899, 20150071903, 20150079681, 20150159172, 20150165054, 20150166980, and 20150184139.

Polynucleotide Delivery

The dual vector system provides for the safe and efficient delivery of exogenous gene constructs to relevant cell targets. In one embodiment, cells in the organ of Corti in the cochlea are targeted. The organ of Corti includes two classes of sensory hair cells: inner hair cells, which convert mechanical information carried by sound into electrical signals transmitted to neuronal structures, and outer hair cells which serve to amplify and tune the cochlear response, a process required for complex hearing function.

In some embodiments, the dual vector system comprises viral vectors. The viral vectors generally contain the minimum required viral sequences for packaging and subsequent integration into a subject. Adeno-associated virus (AAV) vectors used in gene therapy may only contain inverted terminal repeat (ITR) sequences from the AAV genome. These are necessary for packaging and integration into a host genome. Suitable methods for the delivering or administering nucleic acids to cells are available and well known to those skilled in the art, and although more than one route can be used for administering a particular composition, one route may provide a more effective or immediate result than another route.

Methods of delivering viruses (which also can be referred to as viral particles) containing a transgene to inner ear cells are known in the art. As described herein, about 108 to about 1,012 viral particles can be administered to a subject, and the virus can be suspended within a suitable volume (e.g., 10 μL, 50 μL, 100 μL, 500 μL, or 1000 μL) of, for example, artificial perilymph solution.

In some embodiments, a vector described herein (e.g., disrupting vector, replacing vector) comprises a promoter (e.g., an Espin promoter, a protocadherin 15 (PCDH15) promoter, a protein tyrosine phosphatase receptor type Q (PTPRQ) promoter, a myosin VI (Myo6) promoter, a Potassium Voltage-Gated Channel Subfamily Q Member 4 (KCNQ4) promoter, a myosin VIIA (Myo7a) promoter, a synapsin promoter, a glial fibrillary acidic protein (GFAP) promoter, a cytomegalovirus (CMV) promoter, a CMV enhancer, chicken beta-Actin promoter and rabbit beta-Globin splice acceptor site (CAG) promoter, a chicken β-actin (CBA) promoter, a CBH promoter, a U6, type III RNA polymerase promoter, and a tetraspan membrane protein of hair cell stereocilia (TMHS) or lipoma HMGIC fusion partner-like 5 (LHFPL5) promoter) that drives expression of a downstream polynucleotide. One or both vectors may comprise at least one promoter selected from but not limited to CMV and U6.

In some embodiments, a therapeutically effective amount of the dual vector system of the invention is injected through the round window or the oval window, or the utricle, typically in a relatively simple (e.g., outpatient) procedure. In some embodiments, viruses are delivered to the appropriate position within the ear during surgery (e.g., a cochleostomy or a canalostomy).

In some embodiments, delivery vehicles (e.g., polymers) are used to facilitate the transfer of agents across the tympanic membrane and/or through the round window or utricle, and any such delivery vehicles can be used to deliver the viruses described herein. See, for example, Arnold et al., 2005, Audiol. Neurootol., 10:53-63. Other viral vectors that can be used include, for example, a vaccinia virus, a bovine papilloma virus, or a herpes virus, such as Epstein-Barr Virus. Retroviral vectors are particularly well developed and have been used in clinical settings.

In some embodiments, the compositions and methods described herein facilitate the delivery to, and expression of, exogenous polynucleotides in at least 65% (e.g., at least 65, 70, 75, 80, 85, 90, 91, 92, 93, 94, 95, 96, 97, 98, or 99%) of inner and/or outer hair cells or delivery to, and expression in, at least 80% (e.g., at least 85, 90, 91, 92, 93, 94, 95, 96, 97, 98, or 99) of outer hair cells.

In one embodiment, a vector of the invention is an adeno-associated virus (AAV). In another embodiment, a vector of the invention is an Anc80 vector, which is used to transduce greater than about 60% (e.g., 70%, 80%, 90%, 95%, or even 100%) of inner or outer hair cells. In one embodiment, the Anc80 is Anc80-0065 (SEQ ID NO:2), which is described in International Application No. PCT/US2018/017104, which is incorporated herein by reference in its entirety. However, WO 2015/054653, which is also incorporated herein by reference in its entirety, describes a number of additional ancestral capsid proteins that fall within the class of Anc80 ancestral capsid proteins.

In particular embodiments, the adeno-associated virus (AAV) contains an ancestral AAV capsid protein that has a natural or engineered tropism for hair cells. In some embodiments, the virus is an Inner Ear Hair Cell Targeting AAV, which delivers a transgene to the inner ear in a subject. In some embodiments, the virus is an AAV that comprises purified capsid polypeptides. In some embodiments, the virus is artificial.

In some embodiments, one or both vectors of the dual vector system may comprise a heterologous promoter (e.g., CMV promoter, Espin promoter, a PCDH15 promoter, a PTPRQ promoter and a TMHS (LHFPL5) promoter) that drives expression of a downstream polynucleotide. As used herein, a "heterologous promoter" refers to a promoter that does not naturally direct expression of that sequence (i.e., is not found with that sequence in nature).

Methods for packaging a transgene into a virus are known in the art and utilize conventional molecular biology and recombinant nucleic acid techniques. For example, Aponte-Ubillus, et al. (Appl Microbiol Biotechnol. 102:1045-1054, 2018) provides a review of molecular design of AAV vectors for gene therapy, the contents of which are incorporated by reference in its entirety.

In some embodiments, an AAV9-PHP.B vector is used to efficiently target inner ear cells. AAV9-PHP.B is described in International Application No. PCT/US2019/020794, the contents of which are incorporated herein by reference in their entirety. AAV-PHP.B encodes the 7-mer sequence TLAVPFK (SEQ ID NO: 13) and efficiently delivers transgenes to the cochlea, where it showed remarkably specific and robust expression in the inner and outer hair cells. An AAV-PHP.B vector can comprise, but is not limited to, any of the promoters described herein.

Gene transfer can also be achieved using non-viral means involving transfection in vitro. Such methods include the use of calcium phosphate, DEAE dextran, electroporation, and protoplast fusion.

Liposomes can also be potentially beneficial for delivery of DNA into a cell. cDNA expression for use in polynucle-otide therapy methods can be directed from any suitable promoter (e.g., the human cytomegalovirus (CMV), simian virus 40 (SV40), or metallothionein promoters), and regu-lated by any appropriate mammalian regulatory element. For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

Compositions and Methods of Treatment

The present invention provides methods of treating dis-ease and/or disorders or symptoms thereof which comprise administering a therapeutically effective amount of a phar-maceutical composition comprising a dual vector system of the invention, wherein one vector disrupts a target gene comprising a mutation and the other replaces the target gene comprising the mutation with a wild-type version of the gene. Thus, one embodiment is a method of treating a subject suffering from or susceptible to a disease or disorder or symptom thereof associated with a mutation. The method includes administering to the mammal a therapeutic amount of the dual vector system described herein in an amount sufficient to treat a disease or disorder or symptom. The method of treating a subject in need thereof with the dual vector system described here may result in the amelioration, reduction, or repair of the genetic disease, or symptoms thereof, suffered by the subject in need.

The therapeutic methods of the invention (which include prophylactic treatment), in general, comprise administration of a therapeutically effective amount of a dual vector system described herein to a subject in need thereof, including a mammal, particularly a human. Such treatment will be suitably administered to subjects, particularly humans, suf-fering from, having, susceptible to, or at risk for a disease, disorder, or symptom thereof. Determination of those sub-jects "at risk" can be made by any objective or subjective determination by a diagnostic test or opinion of a subject or health care provider (e.g., genetic test, enzyme or protein marker, Marker (as defined herein), family history, and the like).

Compositions are contemplated herein for the treatment of diseases or conditions associated with a mutation asso-ciated with a disorder. For therapeutic purposes, the dual vector systems described herein are used to treat a disease or condition (e.g., dominant progressive hearing loss) as described herein. The dual vector system may be adminis-tered directly to a region of the body (e.g., cochlea). In some embodiments, the region of the body to which the vectors are administered is affected by a disease or condition asso-ciated with a genetic mutation (e.g., dominant, recessive). In some embodiments, the compositions are formulated in a pharmaceutically-acceptable buffer such as physiological saline. Non-limiting methods of administration include injecting into the cochlear duct or the perilymph-filled spaces surrounding the cochlear duct (e.g., scala tympani and scala vestibuli). Injecting into the cochlear duct, which is filled with high potassium endolymph fluid, could provide direct access to hair cells. However, alterations to this delicate fluid environment may disrupt the endocochlear potential, heightening the risk for injection-related toxicity. The perilymph-filled spaces surrounding the cochlear duct, scala tympani and scala vestibuli, can be accessed from the middle ear, either through the oval or round window mem-brane. The round window membrane, which is the only non-bony opening into the inner ear, is relatively easily accessible in many animal models and administration of viral vector using this route is well tolerated. In humans, cochlear implant placement routinely relies on surgical electrode insertion through the round window membrane.

Treatment of human patients or non-human animals are carried out using a therapeutically effective amount of a dual vector system in a physiologically-acceptable carrier. The phrase "pharmaceutically acceptable" refers to those com-pounds of the invention, compositions containing such com-pounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The amount of the dual vector system or composition comprising the dual vector system described here may be in an amount effective for treating a subject suffering from a genetic disease (including disorder or condition), such that the symptoms or genetic disease itself is reduced, amelio-rated, or eliminated with treatment.

The phrase "pharmaceutically-acceptable excipient" includes pharmaceutically-acceptable material, composition or vehicle, such as a liquid or solid filler, diluent, carrier, solvent or encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered traga-canth; (5) malt; (6) gelatin; (7) tale; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and poly-ethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solu-tion; (19) ethyl alcohol; (20) phosphate buffer solutions; and (21) other non-toxic compatible substances employed in pharmaceutical formulations.

The compositions may conveniently be presented in unit dosage form and may be prepared by any methods well known in the art. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, about 5 percent to about 70 percent, or about 10 percent to about 30 percent.

Additional suitable carriers and their formulations are described, for example, in the most recent edition of Remington's Pharmaceutical Sciences by E. W. Martin. The amount of the therapeutic agent to be administered varies depending upon the manner and mode of administration, the age and disease status (e.g., the extent of hearing loss present prior to treatment).

Compositions are administered at a dosage that controls the clinical or physiological symptoms of the disease or condition, as may in some cases be determined by a diagnostic method known to one skilled in the art.

Therapeutic compounds and therapeutic combinations are administered in an effective amount. For example, about 108 to about 1012 viral particles can be administered to a subject, and the virus can be suspended within a suitable volume (e.g., 10 µL, 50 µL, 100 µL, 500 µL, or 1000 µL) of, for example, artificial perilymph solution.

Methods of Treating Diseases Associated with Mutations

The invention provides dual vector systems and methods for using such systems to treat a disease or disorder associated with a mutation. In one embodiment, the dual vector system is used to treat dominant progressive hearing loss (e.g., Deafness, Autosomal Dominant 36, or dominant progressive deafness 36, (DFNA36)). DFNA36 presents as sensorineural hearing loss, i.e., high frequency loss followed by low frequency loss leading to profound loss of all frequencies, as well as tinnitus. Typically, onset occurs between 5 to 28 years of age. DFNA36 is associated with dominant mutations (acquired or inherited) in the TMC1 gene of affected individuals. Autosomal recessive deafness, e.g., DFNB7 or DFNB11, is also caused by mutation in the same TMC1 gene. To disrupt TMC1 in a subject having a dominant mutation in TMC1, a first nucleic acid vector ("the disrupting vector") encoding a Cas9 polypeptide, e.g., an SaCas9-KKH or SpCas9-KKH protein, is used. A second vector ("the replacing vector") encoding a wild-type TMC1 protein and a guide RNA (gRNA) that targets TMC1 is used (FIGS. 1-2). The Cas9-KKH protein disrupts the TMC1 target gene inducing frame shifts and premature stop codons. Expression of wild-type TMC1 from the second vector replaces the disrupted gene, thereby restoring hearing loss associated with a dominant mutation in TMC1.

Figure 3:
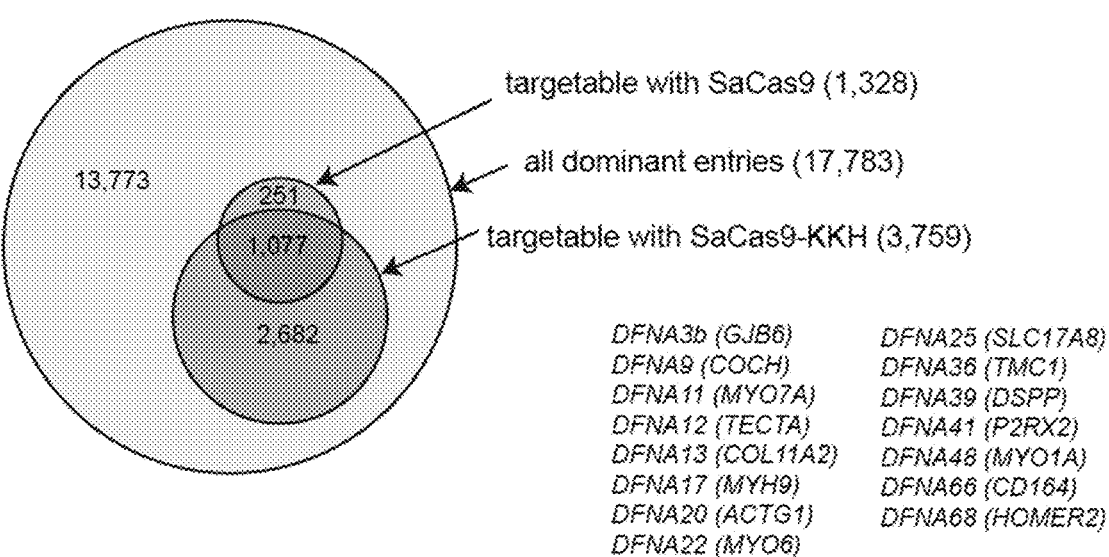
FIG. 3 is an illustration of human dominant mutations in the ClinVar database (accessed 2019 Mar. 25) and mutations targetable with SaCas9 and SaCas9-KKH.

In addition to the TMC1 p.M418K mutation (DFNA36), 15 dominant mutations in genes that are targetable with SaCas9-KKH were identified (FIG. 3 and Table 1). All known dominant human mutations for specific PAM targeting using SaCas9 and SaCas9-KKH were analyzed. SaCas9 has a unique PAM requirement of 'GRRT', while SaCas9-KKH has a PAM requirement only of 'RRT'. Of 17,783 dominant entries in the ClinVar database, the SaCas9 GRRT PAM site was evident in 1,328 variants (7.5%), while the SaCas9-KKH PAM site is able to distinguish mutant from wild-type for 3,759 dominant alleles (21.1%) (FIG. 3).

TABLE 1

| | | Dominant deafness variants potentially targetable with Cas9-KKH | | | | | | |
|---|---|---|---|---|---|---|---|---|
| Deafness locus | OMIM Disease | SNP ID | WT | Variant | Protein | Gene | Link | |
| DFNA11 | .0015 Deafness, Autosomal Dominant 11 | RS= 121965084 | CAATG | CATTG | ASN458ILE | MYO7A | www.omim.org/ entry/276903# 0015 | |
| DFNA12 | .0001 Deafness, Autosomal Dominant 12 | RS= 281865415 | AGCTC | AGTTC | GLY1824ASP | TECTA | www.omim.org/ entry/602574# 0001 | |
| DFNA13 | .0006 Deafness, Autosomal Dominant 13 | RS= 121912947 | GCGCC | GCACC | ARG549CYS | COL11A2 | www.omim.org/ entry/120290# 0005 | |
| DFNA17 | .0008 Deafness, Autosomal Dominant 17 | RS= 80338828 | GGCGG | GGTGG | ARG705HIS | MYH9 | www.omim.org/ entry/160775# 0008 | |
| DFNA20 | .0002 Deafness, Autosomal Dominant 20 | RS= 104894544 | TCTTC | TCATC | LYS118MET | ACTG1 | www.omim.org/ entry/102560# 0002 | |
| DFNA22 | .0001 Deafness, Autosomal Dominant 22 | RS= 121912557 | GTGTT | GTATT | CYS442TYR | MYO6 | www.omim.org/ entry/600970# 0001 | |
| DFNA22 | .0006 Deafness, Autosomal Dominant 22 | RS= 121912561 | AACGA | AATGA | ARG849TER | MYO6 | www.omim.org/ entry/600970# 0006 | |

TABLE 1-continued

Dominant deafness variants potentially targetable with Cas9-KKH

| Deafness locus | OMIM Disease | SNP ID | WT | Variant | Protein | Gene | Link |
|---|---|---|---|---|---|---|---|
| DFNA25 | .0001 Deafness, Autosomal Dominant 25 | RS= 121918339 | GGCAC | GGTAC | ALA211VAL | SLC17A8 | www.omim.org/ entry/607557# 0001 |
| DFNA36 | .0007 Deafness, Autosomal Dominant 36 | RS= 786201027 | GATGT | GAAGT | MET418LYS | TMC1 | www.omim.org/ entry/606706# 0007 |
| DFNA39 | .0004 Deafness, Autosomal Dominant Non syndromic Sensorin- eural 39, With Dentino genesis Imperfecta 1 | RS= 121912987 | AGGTT | AGTTT | VAL18PHE | DSPP | www.omim.org/ entry/125485# 0004 |
| DFNA3b | .0001 Deafness, Autosomal Dominant 3b | RS= 104894414 | GACGC | GATGC | THR5MET | GJB6 | www.omim.org/ entry/604418# 0001 |
| DFNA41 | .0001 Deafness, Autosomal Dominant 41 | RS= 587777692 | ACGTA | ACTTA | VAL60LEU | P2RX2 | www.omim.org/ entry/600844# 0001 |
| DFNA48 | .0004 Re- classified- Variant Of Unknown Significance | RS= 61753849 | GACAT | GAAAT | GLU385ASP | MYO1A | www.omim.org/ entry/601478# 0004 |
| DFNA66 | .0001 Deafness, Autosomal Dominant 66 | RS= 876661402 | TCGTT | TCATT | ARG192TER | CD164 | www.omim.org/ entry/603356# 0001 |
| DFNA68 | .0001 Deafness, Autosomal Dominant 68 | RS= 864309524 | GCCGT | GCGGT | ARG185PRO | HOMER2 | www.omim.org/ entry/604799# 0001 |
| DFNA9 | .0001 Deafness, Autosomal Dominant 9 | RS= 121908927 | AGTAT | AGGAT | VAL66GLY | COCH | www.omim.org/ entry/603196# 0001 |
| DFNA9 | .0005 Deafness, Autosomal Dominant 9 | RS= 121908930 | CATCC | CAACC | ILE109ASN | COCH | www.omim.org/ entry/603196# 0005 |
| DFNA9 | .0006 Deafness, Autosomal Dominant 9 | RS= 121908931 | CTGCT | CTACT | ALA119THR | COCH | www.omim.org/ entry/603196# 0006 |

EXAMPLES

Example 1: Dual Vector System

The invention provides a dual vector gene therapy system, which includes a first vector that disrupts a target gene, and a second vector that provides for the replacement of the disrupted target gene. The first step of the gene editing strategy utilized a vector encoding a highly efficient and selective Cas9 enzyme (e.g., SaCas9-KKH, SpCas9-KKH) having a PAM site that recognized a sequence in a carefully chosen site at the 5' end of the coding region of the target gene. A guide RNA (gRNA) selective for a site adjacent to the PAM was designed to recognize both mutant and wild-type alleles. The guide RNA and PAM are specific for the target gene. When the Cas9-KKH (e.g., SaCas9-KKH, SpCas9-KKH) and the guide RNA were introduced together into the same cell, the Cas9-KKH generated insertions/ deletions (indels) that resulted in frame shifts and premature stop codons, thereby disrupting the target gene, resulting in a functional null allele. In the case of dominant mutations, both mutant and WT alleles were disrupted. In the case of recessive mutations, both recessive alleles were targeted for disruption.

The second step involved the "replacement" of the target gene. In this case, a conventional gene replacement approach was used, where a vector that delivered the wild-type coding sequence for the target gene was utilized. In one embodiment, the vector included a cell-type specific pro-moter driving expression of the wild-type coding sequence. The coding sequence used an alternate codon sequence that was degenerate, i.e. the wild-type amino acid sequence was preserved, but the DNA sequence used alternate codons in the region of the PAM and a guide RNA that "replaced" sequence that was not targeted for disruption by Cas9.

Dual vector transduction was required for the "disrupt and replace" strategy to be effective. One vector carried the Cas9 coding sequence for the disrupt portion of the gene editing strategy and the second vector carried the wild-type (WT) coding sequence for the replace portion of the gene editing. For highly efficient vectors, dual transduction is possible in most cells.

Nevertheless, it is possible that some cells will receive only a single viral transduction event. For those cells trans-duced by just the "replacement" vector, the wild-type sequence will provide recovery of function, at least for recessive mutations. If cells are transduced by just the "disrupt" vector, there is a possibility that the WT allele may be disrupted (for heterozygous dominant genotypes) in cells that do not also receive the "replacement" vector, which could lead to an immediate loss-of-function of both domi-nant and WT alleles. To ensure that the WT gene target was not disrupted without being replaced, i.e., in the subset of cells transduced with just the "disrupt" vector, the guide RNA was provided in the "replace" vector. In this way, only cells that received both the "disrupt" and "replace" vectors will undergo the full "disrupt and replace" events.

Example 2: Analysis of Dual-Vector System in Tmc Knockout Mice In Vivo

Animals

All animals were bred and housed in facilities. All studies involving animals were approved by the HMS Standing Committee on Animals (Protocol No. 03524) and the Boston Children's Hospital Institutional Animal Care and Use Com-mittee (Protocol Nos. 2878 and 3396). All experiments were conducted in accordance with the animal protocols.

Null allele ("knockout") mice that were TMC1 deficient (TMC1−/−) were generated and served as a mouse model for human hearing loss (e.g., Deafness, Autosomal Dominant 36, or dominant progressive deafness 36, (DFNA36) phe-notype caused by dominant (acquired or inherited) TMC1 gene mutations, Met to Lys at position 412 (M412K) and Thymine to Adenine at position 1253 (T1253A) of the Tmc1 gene. The 'Beethoven' (Bth) deaf mutant mouse is a model for autosomal dominant DFNA36. The Bth mouse model was found to accurately recapitulate human hearing loss of the DFNA36 phenotype caused by TMC1 mutations that result in the hair cell degeneration and progressive hearing loss in mice.

Inner Ear Injections

Inner ears of TMC1−/− or TMC1$^{WT/WT}$ mouse pups were injected at postnatal day 1 (P1) with 1 µl of AAV9-PHP.B virus at a rate of 60 nl/min. Vector 1 carried a CMV promoter and the coding sequence for SaCas9-KKH. Vector 2 carried a CMV promoter driving the WT TMC1 sequence with a mutation that did not affect the amino acid sequence and was not recognized by the SaCas9-KKH coding sequence. Vec-tor 2 also contained the U6 promoter and guide RNA sequence that recognized WT and mutant TMC1 alleles. Both vectors were packaged into AAV9-PHP.B. Use of a single vector to replace mutant TMC1 in mouse inner ears occurred in other embodiments. WT TMC1 encoded in either Anc80 or AAV9-PHP.B replaced mutant TMC1 in mouse inner ears in order to recover auditory function. Pups were anesthetized using hypothermia exposure in ice water for 2-3 minutes. Upon anesthesia, a post-auricular incision was made to expose the otic bulla and visualize the cochlea. Injections were made manually with a glass micropipette. After injection, a suture was used to close the skin cut. Then, the injected mice were placed on a 42° C. heating pad for recovery. Pups were returned to the mother after they recovered fully within ~10 minutes. Standard post-operative care was applied after surgery. Sample sizes for in vivo studies were determined on a continuing basis to optimize the sample size and decrease the variance. At P5 to P7, organs of Corti were excised from injected ears. Organ of Corti tissues were incubated at 37° C., 5% $CO_2$ for 8-10 days, and the tectorial membrane was removed immediately before electrophysiology recording.

Hearing Tests

Figure 4:
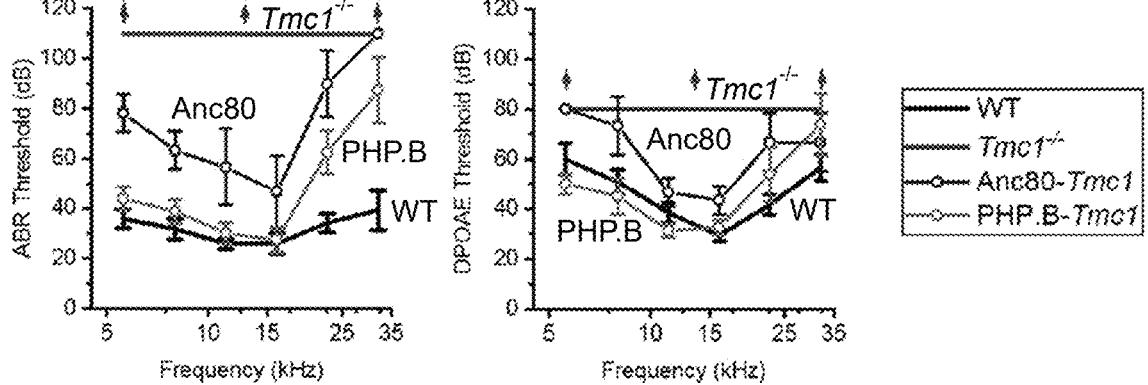
FIG. 4 shows a single vector to replace with wild type (WT) Tmc1. Using a single vector, with WT TMC1 encoded in either Anc80 or AAV9-PHP.B to replace mutant Tmc1 in mouse inner ears, auditory function was recovered. Auditory brainstem responses (ABR) were recorded from WT, Tmc1−/−, or Tmc1−/− mice injected with Anc80-Tmc1 or AAV9-PHP.B-Tmc1. Distortion Product Otoaccoustic Emissions (DPOAE) were recorded and indicate function of outer hair cells.

To determine whether the dual-vector system of the disclosure using AAV vectors (see e.g., FIGS. 1, 2, 5A) were capable of and the extent of recovering hearing loss, Audi-tory Brainstem Responses (ABRs) and Distortion Product Otoacoustic Emissions (DPOAEs) were measured in the TMC1 knockout (TMC1−/−) mice. FIG. 4 demonstrates that the single vector with WT TMC1 encoded in either Anc80 or AAV9-PHP.B that was used to replace mutant Tmc1 in the inner ears of mice resulted in recovery of auditory function. ABR and DPOAE measurements were recorded using the EPL Acoustic system (Massachusetts Eye and Ear, Boston). Acoustic stimuli were generated with 24-bit digital Input/ Output cards (National Instruments PXI-4461) in a PXI-1042Q chassis, amplified by a SA-1 speaker driver (Tucker-Davis Technologies, Inc.), and delivered from two electrostatic drivers (CUI CDMG15008-03A) in a custom acoustic system. An electret microphone (Knowles FG-23329-P07) at the end of a small probe tube was used to monitor ear-canal sound pressure. ABRs and DPOAEs were recorded from mice during the same session. ABR signals were collected using subcutaneous needle electrodes inserted at the pinna (active electrode), vertex (reference electrode), and rump (ground electrode). ABR potentials were amplified (10,000×), pass-filtered (0.3-10 kHz), and digitized using custom data acquisition software (LabVIEW) from the Eaton-Peabody Laboratories Cochlear Function Test Suite. Sound stimuli and electrode voltage were sampled at 40-µs intervals using a digital I-O board (National Instruments) and stored for offline analysis. Threshold was defined visually as the lowest decibel level at which peak 1 could be detected and reproduced with increasing sound intensities. ABR thresholds were averaged within each experimental group and used for statistical analysis. ABR and DPOAE measurements were performed by investigators blinded to the genotype.

Mice were anesthetized with intraperitoneal (i.p.) injection of xylazine (5-10 mg/kg) and ketamine (60-100 mg/kg), and the base of the pinna was trimmed away to expose the ear canal. Three subcutaneous needle electrodes were inserted into the skin, including a) dorsally between the two ears (reference electrode); b) behind the left pinna (recording electrode); and c) dorsally at the rump of the animal (ground electrode). Additional aliquots of ketamine (60-100 mg/kg i.p.) were given throughout the session to maintain anesthesia if needed. Prior to ABR testing, the sound pressure at the entrance of the ear canal was calibrated for each individual test subject at all stimulus frequencies. ABR and DPOAE data were collected under the same conditions and during the same recording sessions.

DPOAEs were recorded first. Primary tones were produced at a frequency ratio of 1.2 (the frequency ratio of f1 and f2 primary tones (f2/f1=1.2)) for generating DPOAEs at 2f1-f2, where the f2 level was 10 dB sound pressure level below f1 level for each f2/f1 pair. The tones were presented with f2 varied between 5.6 and 32.0 kHz in half-octave steps and L1-L2=10 decibel sound pressure level (dB SPL). At each f2, L2 was varied between 10 and 80 dB in 10 dB increments. DPOAE threshold was defined from the average spectra as the L2-level eliciting a DPOAE of magnitude 5 dB above the noise floor. The mean noise floor level was under 0 dB across all frequencies. At each level, waveform and spectral averaging were used in order to increase the signal-to-noise (s/n) ratio of the recorded ear-canal sound pressure. DPOAE at 2f1-2 had an amplitude that was extracted from the averaged spectra, as well as the noise floor at neighboring points in the spectrum. Interpolation from plots of DPOAE amplitude versus sound level resulted in iso-response curves. Threshold was defined as the f2 level required to produce DPOAEs above 0 dB.

ABR experiments were then performed at 32° C. in a sound-proof chamber. To test hearing function, mice were presented with stimuli of broadband "click" tones as well as the pure tones between 5.6 and 32.0 kHz in half-octave steps, all presented as 5-ms tone pips. The responses were amplified (10,000 times), filtered (0.1-3 kHz), and averaged with an analog-to-digital board in a PC-based data-acquisition system (EPL, Cochlear function test suite, MEE, Boston). Across various trials, the sound level was raised in 5 to 10 dB steps from 0 to 110 dB SPL. At each level, 512 responses were collected and averaged for each sound pressure level (with stimulus polarity alternated) after "artifact rejection." Threshold was determined by visual inspection of the appearance of Peak 1 relative to background noise. Data were analyzed and plotted using Origin-2015 (OriginLab Corporation, MA). Thresholds averages±standard deviations are presented unless otherwise stated. The majority of these experiments were not performed under blind conditions.

Figure 5A:
FIG. 5A shows dual AAV vector constructs for expression of the gRNA and SpCas9 nuclease.

Example 3: Screening of gRNAs for Selective Disruption of the Bth Allele Mediated by SpCas9 Nuclease FIG. 5A illustrates the constructs of a dual AAV vector system that express SpCas9 nuclease and guide RNA (gRNA). FIG. 5B presents various guide RNA (gRNA) sequences that were designed to target the Beethoven (Bth) mutation found in the mouse and human TMC1 genes as compared to the wild type (WT) sequence (in grey boxes). The designed gRNA sequences included PAM sequences that are underlined, the nucleotide corresponding to the Bth mutation depicted by an asterisk (*) over the aligned nucleotides, and for the human sequences, nucleotides corresponding to the wild type sequence shown by # over the particular nucleotide of gRNA 16 and gRNA 22.

Figure 5C:
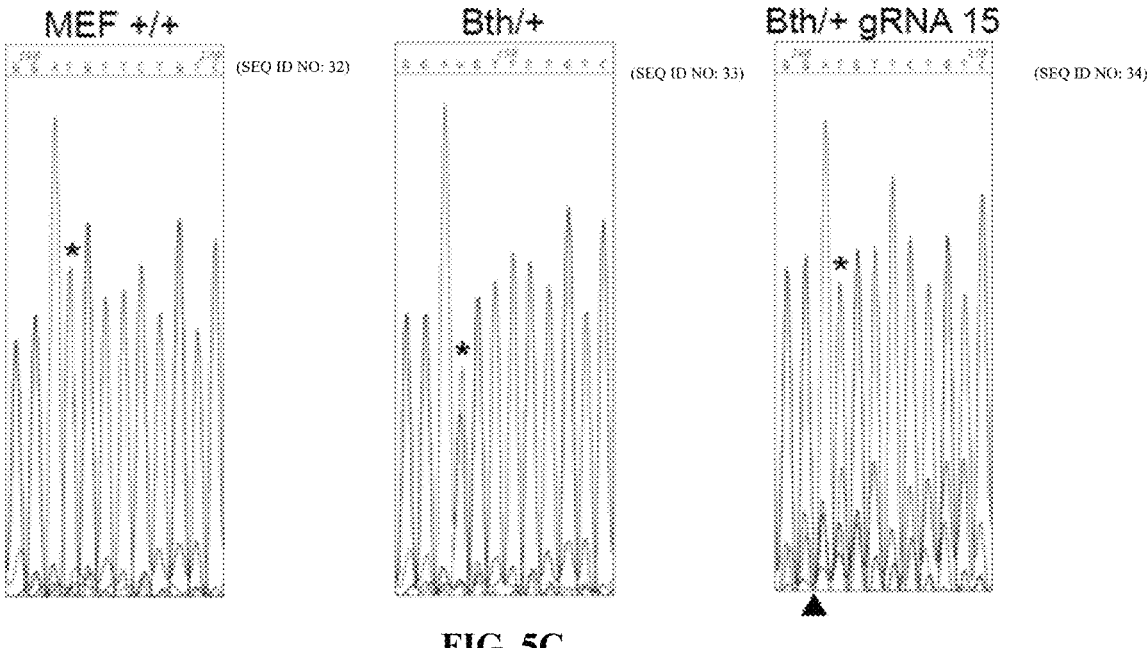
FIG. 5C provides representative sequencing chromatograms of the TMC1 gene in mouse embryonic fibroblast (MEF) cells. * indicates the position corresponding to the T-to-A Bth point mutation. The predominant T in this position in Bth/+ cells transfected with gRNA 15 indicates selective SpCas9-mediated cleavage of the Bth allele. The arrowhead shows the SpCas9 cleavage site.

Sequencing chromatograms of the TMC1 gene in mouse embryonic fibroblast (MEF) cells (FIG. 5C) and near-haploid human (HAP) cells (FIG. 5E) were also performed. The position corresponding to the T-to-A Bth point mutation was identified (*). Note the predominant T in this position in Bth/+ cells transfected with gRNA 15, which indicates selective SpCas9-mediated cleavage of the Bth allele. The arrowhead shows the SpCas9 cleavage site in FIG. 5C. Indels (arrowhead) were shown to be present only in the SpCas9-expressing HAP TMC1$^{Bth}$ cells transfected with gRNA 16 of FIG. 5E.

Figure 5D:
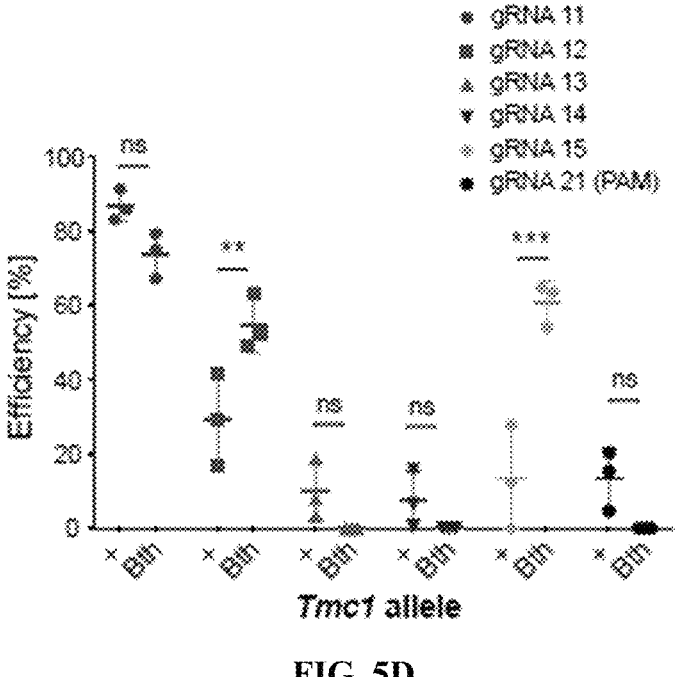
FIG. 5D presents TIDE quantification of gRNA-induced cleavage efficiency based on the relative presence of the + or Bth sequence in Bth/+ mouse embryonic fibroblast (MEF) cells transfected with each of the gRNA-expressing constructs. For each grouping left to right, gRNA 11 (blue circle), gRNA 12 (red square), gRNA 13 (green triangle), gRNA 14 (burgundy inverted triangle), gRNA 15 (orange diamond), gRNA 21 (PAM) (black circle). Note the significant selectivity for the Bth allele of gRNA 12 and 15 (≤0.01, *≤0.001; multiple t-tests with Holm-Sidak method). ns, not significant.
Figure 5E:
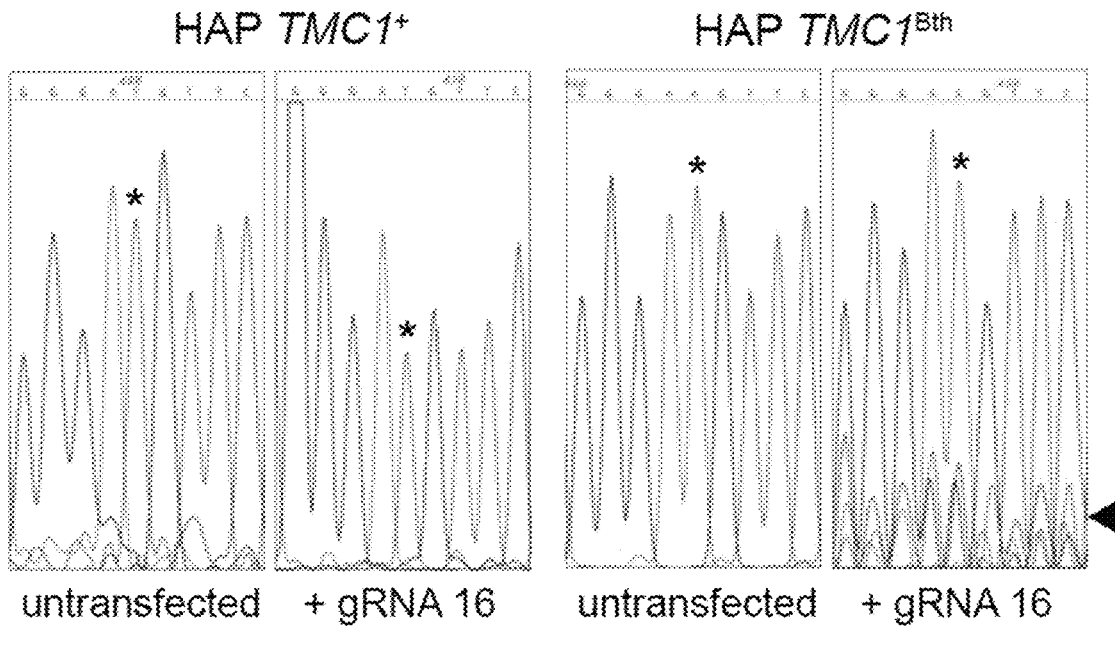
FIG. 5E shows representative sequencing chromatograms of the TMC1 gene in near-haploid human cell line (HAP) TMC1+ and TMC1Bth cells. Note that indels (arrowhead) are present only in the SpCas9-expressing HAP TMC1Bth cells transfected with gRNA 16. * indicates the position corresponding to the T-to-A Bth point mutation.
Figure 5F:
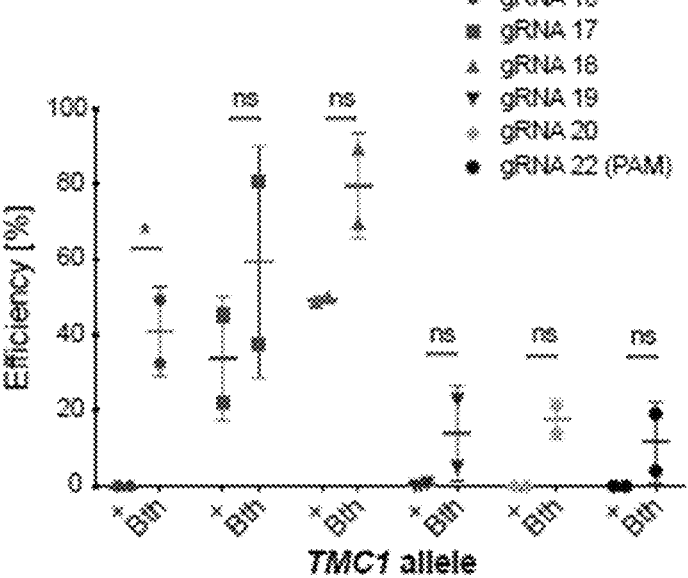
FIG. 5F illustrates tracking of indels by decomposition (TIDE) analysis of gRNA-induced cleavage efficiency based on indel frequency in human haploid (HAP) cells transfected with each of the gRNA-expressing constructs. For each grouping, gRNA 16 (blue circle), gRNA 17 (red square), gRNA 18 (green triangle), gRNA 19 (burgundy inverted triangle), gRNA 20 (orange diamond), gRNA 22 (PAM) (black circle). Note the significant selectivity of gRNA 16 for the Bth allele (*≤0.05; Multiple t tests with Holm-Sidak method). ns, not significant.

Sequence traces were analyzed by deconvolution (TIDE, Tracking Indels by Decomposition, Desktop genetics, UK). Aberrant sequences were quantified downstream of the CRISPR cut site. Analysis was performed on forward vs. reverse traces and efficiency was averaged. FIGS. 5D and 5F show TIDE quantification of gRNA-induced cleavage efficiency based on the relative presence of the wild type (+) or Bth sequence in Bth/WT (+) cells transfected with the indicated gRNA-expressing constructs. Significant selectivity for the Bth allele of gRNA 12, 15, and 16.

Example 4: In Vivo Dual Vector System for SpCas9/gRNA Targeting of the Bth Allele To confirm that the dual vector system works, AAV9-PHP.B-GFP and AAV9-PHPB-RFP were injected and images of the apical-mid-cochlear sections were shown in green (GFP), red (RFP), and Myo7a (blue) (FIG. 6). Auditory function was then shown to recover when Tmc1$^{Bth/+}$ mice were transduced with AAV9-PHP.B-spCas9 and AA9-PHP.B-gRNA15. FIG. 7A presents ABR waveform families recorded from mice (24 weeks) using 11.3 kHz tone bursts at increasing sound pressure levels (dB; y-axis). Thresholds were determined for wild type Tmc1$^{-/-}$ and Tmc1$^{Bth/+}$ mice with AAV9-PHP.B-spCas9 and AAV9-PHP.B-gRNA15.

FIG. 7B shows the ABR and DPOAE thresholds as a function of stimulus frequency for TMC1$^{Bth/+}$ un-injected controls (bold line beneath "Red") to TMC1$^{Bth/+}$ mice dual injected with AAV9-PHP.B-spCas9 and AAV9-PHP.B-gRNA15 (bold line above "Blue") at varying ages. These data were plotted as a function of mice age (4, 6, 12, and 24 weeks) for WT TMC1$^{+/+}$, TMC1$^{Bth/+}$, and TMC1$^{Bth/+}$ with the dual infection of spCas9 and gRNA15. The dual vector injected mice at all age groups had a lower DPOAE threshold (dB) as compared to TMC1$^{Bth/+}$ and was similar to TMC1+/+ threshold levels or above, yet below that of TMC1$^{Bth/+}$ demonstrating recovery of auditory function.

Example 5: AAV9-PHP.B-SpCas9/gRNA Dual Vector Transduction Preserves Hair Cell Survival FIG. 8A compares individual hairs in sections from the apex, middle, and basal cochlear turns of TMC1$^{+/+}$ wild-type and uninjected TMC1$^{Bth/+}$ mice. Clearly the hair cells in the TMC1$^{Bth/+}$ mice are in a disarray as opposed to the uniform hair cells of the wild-type, TMC1$^{+/+}$, and the uniformity is restored in the TMC1$^{Bth/+}$ mice dual injected with AAV9-PHP.B-spCas9 and AAV9-PHP.B-gRNA15. The number of inner (left panel) and outer (right panel) hair cells per 100 μm is lost in TMC1$^{Bth/+}$ mice, while TMC1$^{Bth/+}$ mice dual injected with AAV9-PHP.B-spCas9 and AAV9-PHP.B-gRNA15 increased the number of both inner and outer hair cells at the apex, middle, and base (FIG. 8B). In FIG. 8C, the ABR thresholds were found to be linear as a function of percentage hair cell survival (left panel) and of percentage of green fluorescent protein (GFP) (right panel) in dual infected mice.

Example 6: Sequencing Analysis of In Vivo SpCas9/gRNA Dual Injection

The genomic DNA sequences of AAV9-SpCas9 and gRNA 15 of the TMC1$^{Bth}$ from the Apex and Base halves are presented with the number of reads for each (see, e.g., FIG. 9A). The indel profile s for AAV9-PHP.B-SpCas9 with AAV9-PHP.B-gRNA 15 for TMC1$^{Bth}$ (left panel) or TMC1$^{WT}$ (right panel) were presented (FIG. 9B) where the indel size (nucleotides, nt) (x-axis) are compared to the percent of modified reads (y-axis) based on the information presented in FIG. 9A.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

---

What is claimed is:

1. A dual vector system comprising:

a first vector comprising:

a polynucleotide encoding a Cas9-KKH polypeptide, wherein the first vector does not comprise a polynucleotide encoding a guide RNA (gRNA); and a second vector comprising:

a polynucleotide encoding a guide RNA (gRNA) that binds a target gene comprising a mutation, and a polynucleotide encoding a wild-type version of the target gene, wherein the gRNA is selected from the group consisting of: gRNA 12 (SEQ ID NO: 15), gRNA 15 (SEQ ID NO: 18), and gRNA 16 (SEQ ID NO: 23).

2. The dual vector system of claim 1, wherein one or both vectors comprises at least one promoter.

3. The dual vector system of claim 2, wherein the at least one promoter is selected from: Espin promoter, a protocadherin 15 (PCDH15) promoter, a protein tyrosine phosphatase receptor type Q (PTPRQ) promoter, a myosin VI (Myo6) promoter, a Potassium Voltage-Gated Channel Subfamily Q Member 4 (KCNQ4) promoter, a myosin VIIA (Myo7a) promoter, a synapsin promoter, a glial fibrillary acidic protein (GFAP) promoter, a cytomegalovirus (CMV) promoter, a CMV enhancer, chicken beta-Actin promoter and rabbit beta-Globin splice acceptor site (CAG) promoter, a chicken β-actin (CBA) promoter, a CBH promoter, a U6, type III RNA polymerase promoter, and a tetraspan membrane protein of hair cell stereocilia (TMHS) or lipoma HMGIC fusion partner-like 5 (LHFPL5) promoter.

4. The dual vector system of claim 1, wherein the target gene comprises a mutation associated with a disease or condition.

5. The dual vector system of claim 1, wherein the target gene is TMC1.

6. The dual vector system of claim 1, wherein the mutation is associated with hearing loss.

7. The dual vector system of claim 1, wherein the mutation is DFNA36.

8. The dual vector system of claim 1, wherein the Cas9-KKH is SaCas9-KKH or SpCas9-KKH.

9. A dual vector system comprising:

a) a first AAV9-PHP.B vector comprising a nucleotide sequence encoding Cas9-KKH, wherein the first AAV9-PHP.B vector does not comprise a polynucleotide encoding a guide RNA (gRNA); and b) a second AAV9-PHP.B vector comprising a nucleotide sequence encoding a guide RNA that binds a TMC1 gene comprising a DFNA36 mutation and a polynucleotide encoding a wild-type TMC1 gene, wherein the gRNA is selected from the group consisting gRNA 12 (SEQ ID NO: 15), gRNA 15 (SEQ ID NO: 18), and gRNA 16 (SEQ ID NO: 23).

10. A composition comprising the dual vector system of claim 1.

11. A method of modifying the genome of a cell, the method comprising contacting the cell with the dual vector system of claim 1.

12. A method of genome editing, the method comprising contacting a cell with the dual vector system of claim 1.

13. A method of treating a subject suffering from a genetic disease, the method comprising administering to the subject in need thereof, the dual vector system of claim 1.

14. The method of claim 13, wherein the genetic disease is an autosomal dominant disease.

15. The method of claim 13, wherein the genetic disease is DFNA36 hearing loss.

16. The method of claim 13, wherein the target gene is TMC1.

17. The method of claim 13, wherein the administering step comprises contacting inner ear cells with the dual vector system.

18. The method of claim 1, wherein administering occurs by injecting.

\* \* \* \* \*

SEQUENCE LISTING

```
<160> NUMBER OF SEQ ID NOS: 43

<210> SEQ ID NO 1
<211> LENGTH: 8543
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
ccaatgatac gcgtcggtgc gggcctcttc gctattacgc cagctggcga aagggggatg      60
tgctgcaagg cgattaagtt gggtaacgcc agggttttcc cagtcacgac gttgtaaaac     120
gacggccagt gagcgcgcgt aatacgactc actatagggc gaattgggta catcgacggt     180
atcgggggag ctcgcagggt ctccattttg aagcgggagg tttgaacgcg cagccgccat     240
gccggggttt tacgagattg tgattaaggt ccccagcgac cttgacgagc atctgcccgg     300
catttctgac agctttgtga actgggtggc cgagaaggaa tgggagttgc cgccagattc     360
tgacatggat ctgaatctga ttgagcaggc acccctgacc gtggccgaga agctgcagcg     420
cgactttctg acggaatggc gccgtgtgag taaggccccg gaggctcttt tctttgtgca     480
atttgagaag ggagagagct acttccacat gcacgtgctc gtggaaacca ccggggtgaa     540
atccatggtt ttgggacgtt tcctgagtca gattcgcgaa aaactgattc agagaattta     600
ccgcgggatc gagccgactt tgccaaactg gttcgcggtc acaaagacca gaaatggcgc     660
cggaggcggg aacaaggtgg tggatgagtg ctacatcccc aattacttgc tccccaaaac     720
ccagcctgag ctccagtggg cgtggactaa tatggaacag tatttaagcg cctgtttgaa     780
tctcacggag cgtaaacggt tggtggcgca gcatctgacg cacgtgtcgc agacgcagga     840
gcagaacaaa gagaatcaga atcccaattc tgatgcgccg gtgatcagat caaaaacttc     900
agccaggtac atggagctgg tcgggtggct cgtggacaag gggattacct cggagaagca     960
gtggatccag gaggaccagg cctcatacat ctccttcaat gcggcctcca actcgcggtc    1020
ccaaatcaag gctgccttgg acaatgcggg aaagattatg agcctgacta aaaccgcccc    1080
cgactacctg gtgggccagc agcccgtgga ggacatttcc agcaatcgga tttataaaat    1140
tttggaacta aacgggtacg atccccaata tgcggcttcc gtctttctgg gatgggccac    1200
gaaaaagttc ggcaagagga acaccatctg gctgtttggg cctgcaacta ccgggaagac    1260
caacatcgcg gaggccatag cccacactgt gcccttctac gggtgcgtaa actggaccaa    1320
```

-continued

```
tgagaacttt cccttcaacg actgtgtgga caagatggtg atctggtggg aggaggggaa    1380
gatgaccgcc aaggtcgtgg agtcggccaa agccattctc ggaggaagca aggtgcgcgt    1440
ggaccagaaa tgcaagtcct cggcccagat agacccgact cccgtgatcg tcacctccaa    1500
caccaatatg tgcgccgtga ttgacgggaa ctcaacgacc ttcgaacacc agcagccgtt    1560
gcaagaccgg atgttcaaat ttgaactcac ccgccgtctg gatcatgact ttgggaaggt    1620
caccaagcag gaagtcaaag acttttttccg gtgggcaaag gatcacgtgg ttgaggtgga    1680
gcatgaattc tacgtcaaaa agggtggagc caagaaaaga cccgcccca gtgacgcaga    1740 tataagtgag cccaaacggg tgcgcgagtc agttgcgcag ccatcgacgt cagacgcgga    1800
agcttcgatc aactacgcgg acaggtacca aaacaaatgt tctcgtcacg tgggcatgaa    1860
tctgatgctg tttccctgca gacaatgcga gagactgaat cagaattcaa atatctgctt    1920
cactcacggt gtcaaagact gtttagagtg ctttcccgtg tcagaatctc aacccgtttc    1980
tgtcgtcaaa aaggcgtatc agaaactgtg ctacattcat cacatcatgg aaaaggtgcc    2040
agacgcttgc actgcttgcg acctggtcaa tgtggacttg gatgactgtg tttctgaaca    2100
ataaatgact taaaccaggt atgagtcggc tggataaatc taaagtcata aacggcgctc    2160
tggaattact caatgaagtc ggtatcgaag gcctgacgac aaggaaactc gctcaaaagc    2220
tgggagttga gcagcctacc ctgtactggc acgtgaagaa caagcgggcc ctgctcgatg    2280
ccctggccat cgagatgctg gacaggcatc atacccactt ctgccccctg gaaggcgagt    2340
catggcaaga cttctgcgg aacaacgcca agtcattccg ctgtgctctc ctctcacatc    2400
gcgacggggc taaagtgcat ctcggcaccc gcccaacaga gaaacagtac gaaaccctgg    2460
aaaatcagct cgcgttcctg tgtcagcaag gcttctccct ggagaacgca ctgtacgctc    2520
tgtccgccgt gggccacttt acactgggct gcgtattgga ggaacaggag catcaagtag    2580
caaaagagga aagagagaca cctaccaccg attctatgcc cccacttctg agacaagcaa    2640
ttgagctgtt cgaccggcag ggagccgaac ctgccttcct tttcggcctg gaactaatca    2700
tatgtggcct ggagaaacag ctaaagtgcg aaagcggcgg gccggccgac gcccttgacg    2760
attttgactt agacatgctc ccagccgatg cccttgacga ctttgacctt gatatgctgc    2820
ctgctgacgc tcttgacgat tttgaccttg acatgctccc cgggtaaatg catgaattcg    2880
atctagaggg ccctattcta tagtgtcacc taaatgctag agctcgctga tcagcctcga    2940
ctgtgccttc tagttgccag ccatctgttg tttgcccctc ccccgtgcct tccttgaccc    3000
tggaaggtgc cactcccact gtcctttcct aataaaatga ggaaattgca tcgcattgtc    3060
tgagtaggtg tcattctatt ctgggggggtg gggtggggca ggacagcaag ggggaggatt    3120
gggaagacaa tagcaggcat gctgggatg cggtgggctc tatggcttct gaggcggaaa    3180
gaaccagctg gggctcgaat caagctatca agtgccacct gacgtctccc tatcagtgat    3240
agagaagtcg acacgtctcg agctccctat cagtgataga gaaggtacgt ctagaacgtc    3300
tccctatcag tgatagagaa gtcgacacgt ctcgagctcc ctatcagtga tagagaaggt    3360
acgtctagaa cgtctcccta tcagtgatag agaagtcgac acgtctcgag ctccctatca    3420
gtgatagaga aggtacgtct agaacgtctc cctatcagtg atagagaagt cgacacgtct    3480
cgagctccct atcagtgata gagaaggtac ccctatata agcagagaga tctgttcaaa    3540
tttgaactga ctaagcggct cccgccagat tttggcaaga ttactaagca ggaagtcaag    3600
gacttttttg cttgggcaaa ggtcaatcag gtgccggtc tcacgagtt taaagttccc    3660 agggaattgg cgggaactaa aggggcggag aaatctctaa aacgcccact gggtgacgtc    3720
```

```
accaatacta gctataaaag tctggagaag cgggccaggc tctcatttgt tcccgagacg   3780
cctcgcagtt cagacgtgac tgttgatccc gctcctctgc gaccgctagc ttcgatcaac   3840
tacgcagaca ggtaccaaaa caagtgttct cgtcacgtgg gcattaatct gattctgttt   3900
ccctgcagac aatgcgagag aatgaatcag aactcaaata tctgcttcac tcacggacag   3960
aaagactgtt tagagtgctt tcccgtgtca gaatctcaac ccgtttctgt cgtcaaaaag   4020
gcgtatcaga aactgtgcta cattcatcat atcatgggaa aggtgccaga cgcttgcact   4080
gcctgcgatc tggtcaatgt ggatttggat gactgcatct ttgaacaata aatgacttaa   4140
gccaggtatg gctgccgatg gttatcttcc agattggctc gaggacaacc ttagtgaagg   4200
aattcgcgag tggtgggctt tgaaacctgg agcccctcaa cccaaggcaa atcaacaaca   4260
tcaagacaac gctagaggtc ttgtgcttcc gggttacaaa taccttggac ccggcaacgg   4320
actcgacaag ggggagccgg tcaacgcagc agacgcggcg gccctcgagc acgacaaagc   4380
ctacgaccag cagctcaagg ccggagacaa cccgtacctc aagtacaacc acgccgacgc   4440
cgagttccag gagcggctca agaagatac gtcttttggg ggcaacctcg ggcgagcagt   4500
cttccaggcc aaaaagaggc ttcttgaacc tcttggtctg gttgaggaag cggctaagac   4560
ggctcctgga aagaagaggc ctgtagagca gtctcctcag gaaccggact cctccgcggg   4620
tattggcaaa tcgggtgcac agcccgctaa aaagagactc aatttcggtc agactggcga   4680
cacagagtca gtcccagacc ctcaaccaat cggagaacct cccgcagccc cctcaggtgt   4740
gggatctctt acaatggctt caggtggtgg cgcaccagtg gcagacaata acgaaggtgc   4800
cgatggagtg ggtagttcct cgggaaattg gcattgcgat tcccaatggc tgggggacag   4860
agtcatcacc accagcaccc gaacctgggc cctgcccacc tacaacaatc acctctacaa   4920
gcaaatctcc aacagcacat ctggaggatc ttcaaatgac aacgcctact tcggctacag   4980
caccccctgg gggtattttg acttcaacag attccactgc cacttctcac cacgtgactg   5040
gcagcgactc atcaacaaca actggggatt ccggcctaag cgactcaact tcaagctctt   5100
taacattcag gtcaaagagg ttacggacaa caatggagtc aagaccatcg ccaataacct   5160
taccagcacg gtccaggtct tcacggactc agactatcag ctcccgtacg tgctcgggtc   5220
ggctcacgag ggctgcctcc cgccgttccc agcggacgtt ttcatgattc ctcagtacgg   5280
gtatctgacg cttaatgatg gaagccaggc cgtgggtcgt tcgtcctttt actgcctgga   5340
atatttcccg tcgcaaatgc taagaacggg taacaacttc cagttcagct acgagtttga   5400
gaacgtacct ttccatagca gctacgctca gagccaaagc ctggaccgac taatgaatcc   5460
actcatcgac caatacttgt actatctctc tagaactatt aacggttctg gacagaatca   5520
acaaacgcta aaattcagtg tggccggacc cagcaacatg gctgtccagg aagaaacta    5580 catacctgga cccagctacc gacaacaacg tgtctcaacc actgtgactc aaaacaacaa   5640
cagcgaattt gcttggcctg gagcttcttc ttgggctctc aatggacgta atagcttgat   5700
gaatcctgga cctgctatgg cctctcacaa agaaggagag gaccgtttct ttcctttgtc   5760
tggatcttta attttttggca aacaaggtac tggcagagac aacgtggatg cggacaaagt   5820
catgataacc aacgaagaag aaattaaaac tactaacccg gtagcaacgg agtcctatgg   5880
acaagtggcc acaaaccacc agagtgccca aactttggcg gtgcctttta aggcacaggc   5940
gcagaccggt tgggttcaaa accaaggaat acttccgggt atggtttggc aggacagaga   6000
tgtgtacctg caaggaccca tttgggccaa aattcctcac acggacggca actttcaccc   6060
```

```
ttctccgctg atgggagggt ttggaatgaa gcacccgcct cctcagatcc tcatcaaaaa    6120
cacacctgta cctgcggatc ctccaacggc cttcaacaag gacaagctga actctttcat    6180
cacccagtat tctactggtc aagtcagcgt ggagatcgag tgggagctgc agaaggaaaa    6240
cagcaagcgc tggaacccgg agatccagta cacttccaac tattacaagt ctaataatgt    6300
tgaatttgct gttaatactg aaggtgtata tagtgaaccc cgccccattg gcaccagata    6360
cctgactcgt aatctgtaag tcgacttgct tgttaatcaa taaaccgttt aattcgtttc    6420
agttgaactt tggtctctgc gaagggcaat tcgtttaaac ctgcaggact agaggtcctg    6480
tattagaggt cacgtgagtg ttttgcgaca ttttgcgaca ccatgtggtc acgctgggta    6540
tttaagcccg agtgagcacg cagggtctcc attttgaagc gggaggtttg aacgcgcagc    6600
cgccaagccg aattctgcag atatcacatg tcctaggaac tatcgatcca tcacactggc    6660
ggccgctcga ctagagcggc cgccaccgcg gtggagctcc agcttttgcg gaccgaatcg    6720
gaaagaacat gtgagcaaaa ggccagcaaa aggccaggaa ccgtaaaaag gccgcgttgc    6780
tggcgttttt ccataggctc cgcccccctg acgagcatca caaaaatcga cgctcaagtc    6840
agaggtggcg aaacccgaca ggactataaa gataccaggc gtttccccct ggaagctccc    6900
tcgtgcgctc tcctgttccg accctgccgc ttaccggata cctgtccgcc tttctccctt    6960
cgggaagcgt ggcgctttct catagctcac gctgtaggta tctcagttcg gtgtaggtcg    7020
ttcgctccaa gctgggctgt gtgcacgaac ccccgttca gcccgaccgc tgcgccttat    7080
ccggtaacta tcgtcttgag tccaacccgg taagacacga cttatcgcca ctggcagcag    7140
ccactggtaa caggattagc agagcgaggt atgtaggcgg tgctacagag ttcttgaagt    7200
ggtggcctaa ctacggctac actagaagaa cagtatttgg tatctgcgct ctgctgaagc    7260
cagttacctt cggaaaaaga gttggtagct cttgatccgg caaacaaacc accgctggta    7320
gcggtggttt ttttgtttgc aagcagcaga ttacgcgcag aaaaaaagga tctcaagaag    7380
atcctttgat cttttctacg gggtctgacg ctcagtggaa cgaaaactca cgttaaggga    7440
ttttggtcat gagattatca aaaaggatct tcacctagat ccttttaaat taaaaatgaa    7500
gttttaaatc aatctaaagt atatatgagt aaacttggtc tgacagttac caatgcttaa    7560
tcagtgaggc acctatctca gcgatctgtc tatttcgttc atccatagtt gcctgactcc    7620
ccgtcgtgta gataactacg atacgggagg gcttaccatc tggccccagt gctgcaatga    7680
taccgcgaga cccacgctca ccggctccag atttatcagc aataaaccag ccagccggaa    7740
gggccgagcg cagaagtggt cctgcaactt tatccgcctc catccagtct attaattgtt    7800
gccgggaagc tagagtaagt agttcgccag ttaatagttt gcgcaacgtt gttgccattg    7860
ctacaggcat cgtggtgtca cgctcgtcgt ttggtatggc ttcattcagc tccggttccc    7920
aacgatcaag gcgagttaca tgatccccca tgttgtgcaa aaaagcggtt agctccttcg    7980
gtcctccgat cgttgtcaga agtaagttgg ccgcagtgtt atcactcatg gttatggcag    8040
cactgcataa ttctcttact gtcatgccat ccgtaagatg cttttctgtg actggtgagt    8100
actcaaccaa gtcattctga gaatagtgta tgcggcgacc gagttgctct tgcccggcgt    8160
caatacggga taataccgcg ccacatagca gaactttaaa agtgctcatc attggaaaac    8220
gttcttcggg gcgaaaactc tcaaggatct taccgctgtt gagatccagt tcgatgtaac    8280
ccactcgtgc acccaactga tcttcagcat cttttacttt caccagcgtt tctgggtgag    8340
caaaaacagg aaggcaaaat gccgcaaaaa agggaataag ggcgacacgg aaatgttgaa    8400
tactcatact cttccttttt caatattatt gaagcattta tcagggttat tgtctcatga    8460
```

-continued gcggatacat atttgaatgt atttagaaaa ataaacaaat aggggttccg cgcacatttc      8520
cccgaaaagt gccacctgac gtc                                              8543

<210> SEQ ID NO 2
<211> LENGTH: 734
<212> TYPE: PRT
<213> ORGANISM: Unknown
<220> FEATURE:
<223> OTHER INFORMATION: Description of Unknown:
      Anc80 sequence

<400> SEQUENCE: 2

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
        130                 135                 140

Pro Val Glu Gln Ser Pro Gln Glu Pro Asp Ser Ser Ser Gly Ile Gly
145                 150                 155                 160

Lys Lys Gly Gln Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Ser Asn Thr Met Ala Ala Gly Gly Gly
            195                 200                 205

Ala Pro Met Ala Asp Asn Asn Glu Gly Ala Asp Gly Val Gly Asn Ala
        210                 215                 220

Ser Gly Asn Trp His Cys Asp Ser Thr Trp Leu Gly Asp Arg Val Ile
225                 230                 235                 240

Thr Thr Ser Thr Arg Thr Ala Leu Pro Thr Tyr Asn Asn His Leu Tyr
                245                 250                 255

Lys Gln Ile Ser Ser Gln Ser Gly Gly Ser Thr Asn Asp Asn Thr Tyr
                260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
    290                 295                 300

Gly Phe Arg Pro Lys Lys Leu Asn Phe Lys Leu Phe Asn Ile Gln Val
305                 310                 315                 320

Lys Glu Val Thr Thr Asn Asp Gly Thr Thr Thr Ile Ala Asn Asn Leu
                325                 330                 335

```
Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Ile Pro Gln Tyr Gly Tyr Leu Thr Leu Asn Asn Gly Ser
            370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
            435                 440                 445

Gln Thr Thr Ser Gly Thr Ala Gly Asn Arg Thr Leu Gln Phe Ser Gln
            450                 455                 460

Ala Gly Pro Ser Ser Met Ala Asn Gln Ala Lys Asn Trp Leu Pro Gly
465                 470                 475                 480

Pro Cys Tyr Arg Gln Gln Arg Val Ser Lys Thr Thr Asn Gln Asn Asn
                485                 490                 495

Asn Ser Asn Phe Ala Trp Thr Gly Ala Thr Lys Tyr His Leu Asn Gly
                500                 505                 510

Arg Asp Ser Leu Val Asn Pro Gly Pro Ala Met Ala Thr His Lys Asp
                515                 520                 525

Asp Glu Asp Lys Phe Phe Pro Met Ser Gly Val Leu Ile Phe Gly Lys
            530                 535                 540

Gln Gly Ala Gly Asn Ser Asn Val Asp Leu Asp Asn Val Met Ile Thr
545                 550                 555                 560

Asn Glu Glu Glu Ile Lys Thr Thr Asn Pro Val Ala Thr Glu Glu Tyr
                565                 570                 575

Gly Thr Val Ala Thr Asn Leu Gln Ser Ala Asn Thr Ala Pro Ala Thr
                580                 585                 590

Gly Thr Val Asn Ser Gln Gly Ala Leu Pro Gly Met Val Trp Gln Asp
            595                 600                 605

Arg Asp Val Tyr Leu Gln Gly Pro Ile Trp Ala Lys Ile Pro His Thr
            610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Pro Thr Thr Phe Ser Pro Ala Lys Phe Ala Ser Phe Ile Thr Gln
                660                 665                 670

Tyr Ser Thr Gly Gln Val Ser Val Glu Ile Glu Glu Leu Gln Lys Glu
            675                 680                 685

Asn Ser Lys Arg Trp Asn Pro Glu Ile Gln Tyr Thr Ser Asn Tyr Asn
            690                 695                 700

Lys Ser Thr Asn Val Asp Phe Ala Val Asp Thr Asn Gly Val Tyr Ser
705                 710                 715                 720

Glu Pro Arg Pro Ile Gly Thr Arg Tyr Leu Thr Arg Asn Leu
                725                 730
```

<210> SEQ ID NO 3
<211> LENGTH: 1368
<212> TYPE: PRT

```
<213> ORGANISM: Unknown
<220> FEATURE:
<223> OTHER INFORMATION: Description of Unknown:
      Cas9 sequence

<400> SEQUENCE: 3

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380
```

-continued

```
Gly Thr Glu Glu Leu Leu Val Lys Leu Asn Arg Glu Asp Leu Leu Arg
385             390             395             400

Lys Gln Arg Thr Phe Asp Asn Gly Ser Ile Pro His Gln Ile His Leu
            405             410             415

Gly Glu Leu His Ala Ile Leu Arg Arg Gln Glu Asp Phe Tyr Pro Phe
            420             425             430

Leu Lys Asp Asn Arg Glu Lys Ile Glu Lys Ile Leu Thr Phe Arg Ile
            435             440             445

Pro Tyr Tyr Val Gly Pro Leu Ala Arg Gly Asn Ser Arg Phe Ala Trp
    450             455             460

Met Thr Arg Lys Ser Glu Glu Thr Ile Thr Pro Trp Asn Phe Glu Glu
465             470             475             480

Val Val Asp Lys Gly Ala Ser Ala Gln Ser Phe Ile Glu Arg Met Thr
            485             490             495

Asn Phe Asp Lys Asn Leu Pro Asn Glu Lys Val Leu Pro Lys His Ser
            500             505             510

Leu Leu Tyr Glu Tyr Phe Thr Val Tyr Asn Glu Leu Thr Lys Val Lys
            515             520             525

Tyr Val Thr Glu Gly Met Arg Lys Pro Ala Phe Leu Ser Gly Glu Gln
    530             535             540

Lys Lys Ala Ile Val Asp Leu Leu Phe Lys Thr Asn Arg Lys Val Thr
545             550             555             560

Val Lys Gln Leu Lys Glu Asp Tyr Phe Lys Lys Ile Glu Cys Phe Asp
            565             570             575

Ser Val Glu Ile Ser Gly Val Glu Asp Arg Phe Asn Ala Ser Leu Gly
            580             585             590

Thr Tyr His Asp Leu Leu Lys Ile Ile Lys Asp Lys Asp Phe Leu Asp
            595             600             605

Asn Glu Glu Asn Glu Asp Ile Leu Glu Asp Ile Val Leu Thr Leu Thr
    610             615             620

Leu Phe Glu Asp Arg Glu Met Ile Glu Glu Arg Leu Lys Thr Tyr Ala
625             630             635             640

His Leu Phe Asp Asp Lys Val Met Lys Gln Leu Lys Arg Arg Arg Tyr
            645             650             655

Thr Gly Trp Gly Arg Leu Ser Arg Lys Leu Ile Asn Gly Ile Arg Asp
            660             665             670

Lys Gln Ser Gly Lys Thr Ile Leu Asp Phe Leu Lys Ser Asp Gly Phe
            675             680             685

Ala Asn Arg Asn Phe Met Gln Leu Ile His Asp Asp Ser Leu Thr Phe
    690             695             700

Lys Glu Asp Ile Gln Lys Ala Gln Val Ser Gly Gln Gly Asp Ser Leu
705             710             715             720

His Glu His Ile Ala Asn Leu Ala Gly Ser Pro Ala Ile Lys Lys Gly
            725             730             735

Ile Leu Gln Thr Val Lys Val Val Asp Glu Leu Val Lys Val Met Gly
            740             745             750

Arg His Lys Pro Glu Asn Ile Val Ile Glu Met Ala Arg Glu Asn Gln
            755             760             765

Thr Thr Gln Lys Gly Gln Lys Asn Ser Arg Glu Arg Met Lys Arg Ile
    770             775             780

Glu Glu Gly Ile Lys Glu Leu Gly Ser Gln Ile Leu Lys Glu His Pro
785             790             795             800

Val Glu Asn Thr Gln Leu Gln Asn Glu Lys Leu Tyr Leu Tyr Tyr Leu
```

```
                    805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
        850                 855                 860

Gly Lys Ser Asp Asn Val Pro Ser Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys  Tyr Pro Lys Leu Glu  Ser Glu Phe
            995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200

Phe Glu  Leu Glu Asn Gly Arg  Lys Arg Met Leu Ala  Ser Ala Gly
    1205                1210                1215
```

-continued

```
Glu Leu  Gln Lys Gly Asn Glu  Leu Ala Leu Pro Ser  Lys Tyr Val
    1220                1225                1230

Asn Phe  Leu Tyr Leu Ala Ser  His Tyr Glu Lys Leu  Lys Gly Ser
    1235                1240                1245

Pro Glu  Asp Asn Glu Gln Lys  Gln Leu Phe Val Glu  Gln His Lys
    1250                1255                1260

His Tyr  Leu Asp Glu Ile Ile  Glu Gln Ile Ser Glu  Phe Ser Lys
    1265                1270                1275

Arg Val  Ile Leu Ala Asp Ala  Asn Leu Asp Lys Val  Leu Ser Ala
    1280                1285                1290

Tyr Asn  Lys His Arg Asp Lys  Pro Ile Arg Glu Gln  Ala Glu Asn
    1295                1300                1305

Ile Ile  His Leu Phe Thr Leu  Thr Asn Leu Gly Ala  Pro Ala Ala
    1310                1315                1320

Phe Lys  Tyr Phe Asp Thr Thr  Ile Asp Arg Lys Arg  Tyr Thr Ser
    1325                1330                1335

Thr Lys  Glu Val Leu Asp Ala  Thr Leu Ile His Gln  Ser Ile Thr
    1340                1345                1350

Gly Leu  Tyr Glu Thr Arg Ile  Asp Leu Ser Gln Leu  Gly Gly Asp
    1355                1360                1365
```

```
<210> SEQ ID NO 4
<211> LENGTH: 4107
<212> TYPE: DNA
<213> ORGANISM: Streptococcus pyogenes

<400> SEQUENCE: 4
atggataaga aatactcaat aggcttagat atcggcacaa atagcgtcgg atgggcggtg      60
atcactgatg aatataaggt tccgtctaaa aagttcaagg ttctgggaaa tacagaccgc     120
cacagtatca aaaaaaatct tatagggggct ctttttatttg acagtggaga gacagcggaa    180
gcgactcgtc tcaaacggac agctcgtaga aggtatacac gtcggaagaa tcgtatttgt     240
tatctacagg agattttttc aaatgagatg gcgaaagtag atgatagttt ctttcatcga     300
cttgaagagt cttttttggt ggaagaagac aagaagcatg aacgtcatcc tatttttgga     360
aatatagtag atgaagttgc ttatcatgag aaatatccaa ctatctatca tctgcgaaaa     420
aaattggtag attctactga taaagcggat ttgcgcttaa tctatttggc cttagcgcat     480
atgattaagt tccgtggtca ttttttgatt gagggagatt taaatcctga taatagtgat     540
gtggacaaac tatttatcca gttggtacaa acctacaatc aattatttga agaaaaccct     600
attaacgcaa gtggagtaga tgctaaagcg attctttctg cacgattgag taaatcaaga     660
cgattagaaa atctcattgc tcagctcccc ggtgagaaga aaaatggctt atttgggaat     720
ctcattgctt tgtcattggg tttgaccccct aattttaaat caaattttga tttggcagaa     780
gatgctaaat tacagctttc aaaagatact tacgatgatg atttagataa atttattggcg     840 caaattggag atcaatatgc tgatttgttt ttggcagcta agaatttatc agatgctatt     900
ttactttcag atatcctaag agtaaatact gaaataacta aggctcccct atcagcttca     960
atgattaaac gctacgatga acatcatcaa gacttgactc ttttaaaagc tttagttcga    1020
caacaacttc cagaaaagta taaagaaatc ttttttgatc aatcaaaaaa cggatatgca    1080
ggttatattg atgggggagc tagccaagaa gaatttttata aatttatcaa accaattttta    1140 gaaaaaatgg atggtactga ggaattattg gtgaaactaa atcgtgaaga tttgctgcgc    1200
```

-continued

```
aagcaacgga cctttgacaa cggctctatt ccccatcaaa ttcacttggg tgagctgcat   1260
gctattttga gaagacaaga agactttat ccattttaa aagacaatcg tgagaagatt    1320
gaaaaaatct tgacttttcg aattccttat tatgttggtc cattggcgcg tggcaatagt   1380
cgttttgcat ggatgactcg gaagtctgaa gaaacaatta ccccatggaa ttttgaagaa    1440
gttgtcgata aaggtgcttc agctcaatca tttattgaac gcatgacaaa ctttgataaa   1500
aatcttccaa atgaaaaagt actaccaaaa catagtttgc tttatgagta ttttacggtt   1560
tataacgaat tgacaaaggt caaatatgtt actgaaggaa tgcgaaaacc agcatttctt   1620
tcaggtgaac agaagaaagc cattgttgat ttactcttca aaacaaatcg aaaagtaacc    1680
gttaagcaat taaaagaaga ttatttcaaa aaaatagaat gttttgatag tgttgaaatt    1740
tcaggagttg aagatagatt taatgcttca ttaggtacct accatgattt gctaaaaatt   1800
attaaagata aagattttt ggataatgaa gaaaatgaag atatcttaga ggatattgtt    1860
ttaacattga ccttatttga agatagggag atgattgagg aaagacttaa aacatatgct   1920
cacctctttg atgataaggt gatgaaacag cttaaacgtc gccgttatac tggttgggga   1980
cgtttgtctc gaaaattgat taatggtatt agggataagc aatctggcaa aacaatatta   2040
gattttttga aatcagatgg ttttgccaat cgcaatttta tgcagctgat ccatgatgat    2100
agtttgacat ttaaagaaga cattcaaaaa gcacaagtgt ctggacaagg cgatagttta   2160
catgaacata ttgcaaattt agctggtagc cctgctatta aaaaaggtat tttacagact   2220
gtaaaagttg ttgatgaatt ggtcaaagta atggggcggc ataagccaga aaatatcgtt   2280
attgaaatgg cacgtgaaaa tcagacaact caaaagggcc agaaaaattc gcgagagcgt   2340
atgaaacgaa tcgaagaagg tatcaaagaa ttaggaagtc agattcttaa agagcatcct   2400
gttgaaaata ctcaattgca aaatgaaaag ctctatctct attatctcca aaatggaaga   2460
gacatgtatg tggaccaaga attagatatt aatcgtttaa gtgattatga tgtcgatcac   2520
attgttccac aaagtttcct taaagacgat tcaatagaca ataaggtctt aacgcgttct   2580
gataaaaatc gtggtaaatc ggataacgtt ccaagtgaag aagtagtcaa aaagatgaaa   2640
aactattgga gacaacttct aaacgccaag ttaatcactc aacgtaagtt tgataattta   2700
acgaaagctg aacgtggagg tttgagtgaa cttgataaag ctggttttat caaacgccaa   2760
ttggttgaaa ctcgccaaat cactaagcat gtggcacaaa ttttggatag tcgcatgaat   2820
actaaatacg atgaaaatga taaacttatt cgagaggtta aagtgattac cttaaaatct   2880
aaattagttt ctgacttccg aaaagatttc caattctata agtacgtga gattaacaat    2940 taccatcatg cccatgatgc gtatctaaat gccgtcgttg gaactgcttt gattaagaaa   3000
tatccaaaac ttgaatcgga gtttgtctat ggtgattata agtttatga tgttcgtaaa    3060 atgattgcta agtctgagca agaaataggc aaagcaaccg caaatatttt cttttactct   3120
aatatcatga acttcttcaa aacagaaatt acacttgcaa atggagagat tcgcaaacgc   3180
cctctaatcg aaactaatgg ggaaactgga gaaattgtct gggataaagg gcgagatttt   3240
gccacagtgc gcaaagtatt gtccatgccc caagtcaata ttgtcaagaa aacagaagta   3300
cagacaggcg gattctccaa ggagtcaatt ttaccaaaaa gaaattcgga caagcttatt   3360
gctcgtaaaa aagactggga tccaaaaaaa tatggtggtt ttgatagtcc aacggtagct   3420
tattcagtcc tagtggttgc taaggtggaa aaagggaaat cgaagaagtt aaaatccgtt   3480
aaagagttac tagggatcac aattatggaa agaagttcct ttgaaaaaaa tccgattgac   3540 ttttttagaag ctaaaggata taaggaagtt aaaaaagact taatcattaa actacctaaa    3600
```

-continued

```
tatagtcttt ttgagttaga aaacggtcgt aaacggatgc tggctagtgc cggagaatta    3660
caaaaaggaa atgagctggc tctgccaagc aaatatgtga attttttata tttagctagt    3720
cattatgaaa agttgaaggg tagtccagaa gataacgaac aaaaacaatt gtttgtggag    3780
cagcataagc attatttaga tgagattatt gagcaaatca gtgaatttc taagcgtgtt    3840 attttagcag atgccaattt agataaagtt cttagtgcat ataacaaaca tagagacaaa    3900
ccaatacgtg aacaagcaga aaatattatt catttattta cgttgacgaa tcttggagct    3960
cccgctgctt ttaaatattt tgatacaaca attgatcgta aacgatatac gtctacaaaa    4020
gaagttttag atgccactct tatccatcaa tccatcactg gtctttatga aacacgcatt    4080
gatttgagtc agctaggagg tgactga                                         4107
```

<210> SEQ ID NO 5
<211> LENGTH: 1087
<212> TYPE: PRT
<213> ORGANISM: Staphylococcus aureus

<400> SEQUENCE: 5

```
Met Ala Pro Lys Lys Lys Arg Lys Val Gly Ile His Gly Val Pro Ala
1               5                   10                  15

Ala Lys Arg Asn Tyr Ile Leu Gly Leu Asp Ile Gly Ile Thr Ser Val
            20                  25                  30

Gly Tyr Gly Ile Ile Asp Tyr Glu Thr Arg Asp Val Ile Asp Ala Gly
        35                  40                  45

Val Arg Leu Phe Lys Glu Ala Asn Val Glu Asn Asn Glu Gly Arg Arg
    50                  55                  60

Ser Lys Arg Gly Ala Arg Arg Leu Lys Arg Arg Arg His Arg Ile
65                  70                  75                  80

Gln Arg Val Lys Lys Leu Leu Phe Asp Tyr Asn Leu Leu Thr Asp His
                85                  90                  95

Ser Glu Leu Ser Gly Ile Asn Pro Tyr Glu Ala Arg Val Lys Gly Leu
            100                 105                 110

Ser Gln Lys Leu Ser Glu Glu Glu Phe Ser Ala Ala Leu Leu His Leu
        115                 120                 125

Ala Lys Arg Arg Gly Val His Asn Val Asn Glu Val Glu Glu Asp Thr
    130                 135                 140

Gly Asn Glu Leu Ser Thr Lys Glu Gln Ile Ser Arg Asn Ser Lys Ala
145                 150                 155                 160

Leu Glu Glu Lys Tyr Val Ala Glu Leu Gln Leu Glu Arg Leu Lys Lys
                165                 170                 175

Asp Gly Glu Val Arg Gly Ser Ile Asn Arg Phe Lys Thr Ser Asp Tyr
            180                 185                 190

Val Lys Glu Ala Lys Gln Leu Leu Lys Val Gln Lys Ala Tyr His Gln
        195                 200                 205

Leu Asp Gln Ser Phe Ile Asp Thr Tyr Ile Asp Leu Leu Glu Thr Arg
    210                 215                 220

Arg Thr Tyr Tyr Glu Gly Pro Gly Glu Gly Ser Pro Phe Gly Trp Lys
225                 230                 235                 240

Asp Ile Lys Glu Trp Tyr Glu Met Leu Met Gly His Cys Thr Tyr Phe
                245                 250                 255

Pro Glu Glu Leu Arg Ser Val Lys Tyr Ala Tyr Asn Ala Asp Leu Tyr
            260                 265                 270

Asn Ala Leu Asn Asp Leu Asn Asn Leu Val Ile Thr Arg Asp Glu Asn
```

-continued

```
          275              280              285
Glu Lys Leu Glu Tyr Tyr Glu Lys Phe Gln Ile Ile Glu Asn Val Phe
    290              295              300

Lys Gln Lys Lys Lys Pro Thr Leu Lys Gln Ile Ala Lys Glu Ile Leu
305              310              315              320

Val Asn Glu Glu Asp Ile Lys Gly Tyr Arg Val Thr Ser Thr Gly Lys
            325              330              335

Pro Glu Phe Thr Asn Leu Lys Val Tyr His Asp Ile Lys Asp Ile Thr
            340              345              350

Ala Arg Lys Glu Ile Ile Glu Asn Ala Glu Leu Leu Asp Gln Ile Ala
            355              360              365

Lys Ile Leu Thr Ile Tyr Gln Ser Ser Glu Asp Ile Gln Glu Glu Leu
    370              375              380

Thr Asn Leu Asn Ser Glu Leu Thr Gln Glu Glu Ile Glu Gln Ile Ser
385              390              395              400

Asn Leu Lys Gly Tyr Thr Gly Thr His Asn Leu Ser Leu Lys Ala Ile
            405              410              415

Asn Leu Ile Leu Asp Glu Leu Trp His Thr Asn Asp Asn Gln Ile Ala
            420              425              430

Ile Phe Asn Arg Leu Lys Leu Val Pro Lys Lys Val Asp Leu Ser Gln
            435              440              445

Gln Lys Glu Ile Pro Thr Thr Leu Val Asp Asp Phe Ile Leu Ser Pro
    450              455              460

Val Val Lys Arg Ser Phe Ile Gln Ser Ile Lys Val Ile Asn Ala Ile
465              470              475              480

Ile Lys Lys Tyr Gly Leu Pro Asn Asp Ile Ile Ile Glu Leu Ala Arg
            485              490              495

Glu Lys Asn Ser Lys Asp Ala Gln Lys Met Ile Asn Glu Met Gln Lys
            500              505              510

Arg Asn Arg Gln Thr Asn Glu Arg Ile Glu Glu Ile Ile Arg Thr Thr
            515              520              525

Gly Lys Glu Asn Ala Lys Tyr Leu Ile Glu Lys Ile Lys Leu His Asp
    530              535              540

Met Gln Glu Gly Lys Cys Leu Tyr Ser Leu Glu Ala Ile Pro Leu Glu
545              550              555              560

Asp Leu Leu Asn Asn Pro Phe Asn Tyr Glu Val Asp His Ile Ile Pro
            565              570              575

Arg Ser Val Ser Phe Asp Asn Ser Phe Asn Asn Lys Val Leu Val Lys
            580              585              590

Gln Glu Glu Asn Ser Lys Lys Gly Asn Arg Thr Pro Phe Gln Tyr Leu
            595              600              605

Ser Ser Ser Asp Ser Lys Ile Ser Tyr Glu Thr Phe Lys Lys His Ile
    610              615              620

Leu Asn Leu Ala Lys Gly Lys Gly Arg Ile Ser Lys Thr Lys Lys Glu
625              630              635              640

Tyr Leu Leu Glu Glu Arg Asp Ile Asn Arg Phe Ser Val Gln Lys Asp
            645              650              655

Phe Ile Asn Arg Asn Leu Val Asp Thr Arg Tyr Ala Thr Arg Gly Leu
            660              665              670

Met Asn Leu Leu Arg Ser Tyr Phe Arg Val Asn Asn Leu Asp Val Lys
            675              680              685

Val Lys Ser Ile Asn Gly Gly Phe Thr Ser Phe Leu Arg Arg Lys Trp
    690              695              700
```

-continued

```
Lys Phe Lys Lys Glu Arg Asn Lys Gly Tyr Lys His His Ala Glu Asp
705                 710                 715             720

Ala Leu Ile Ile Ala Asn Ala Asp Phe Ile Phe Lys Glu Trp Lys Lys
                725                 730                 735

Leu Asp Lys Ala Lys Lys Val Met Glu Asn Gln Met Phe Glu Glu Lys
            740                 745                 750

Gln Ala Glu Ser Met Pro Glu Ile Glu Thr Glu Gln Glu Tyr Lys Glu
            755                 760                 765

Ile Phe Ile Thr Pro His Gln Ile Lys His Ile Lys Asp Phe Lys Asp
            770                 775                 780

Tyr Lys Tyr Ser His Arg Val Asp Lys Lys Pro Asn Arg Glu Leu Ile
785                 790                 795             800

Asn Asp Thr Leu Tyr Ser Thr Arg Lys Asp Asp Lys Gly Asn Thr Leu
                805                 810                 815

Ile Val Asn Asn Leu Asn Gly Leu Tyr Asp Lys Asp Asn Asp Lys Leu
                820                 825                 830

Lys Lys Leu Ile Asn Lys Ser Pro Glu Lys Leu Leu Met Tyr His His
            835                 840                 845

Asp Pro Gln Thr Tyr Gln Lys Leu Lys Leu Ile Met Glu Gln Tyr Gly
    850                 855                 860

Asp Glu Lys Asn Pro Leu Tyr Lys Tyr Tyr Glu Glu Thr Gly Asn Tyr
865                 870                 875             880

Leu Thr Lys Tyr Ser Lys Lys Asp Asn Gly Pro Val Ile Lys Lys Ile
                885                 890                 895

Lys Tyr Tyr Gly Asn Lys Leu Asn Ala His Leu Asp Ile Thr Asp Asp
            900                 905                 910

Tyr Pro Asn Ser Arg Asn Lys Val Val Lys Leu Ser Leu Lys Pro Tyr
            915                 920                 925

Arg Phe Asp Val Tyr Leu Asp Asn Gly Val Tyr Lys Phe Val Thr Val
    930                 935                 940

Lys Asn Leu Asp Val Ile Lys Lys Glu Asn Tyr Tyr Glu Val Asn Ser
945                 950                 955             960

Lys Cys Tyr Glu Glu Ala Lys Lys Leu Lys Lys Ile Ser Asn Gln Ala
                965                 970                 975

Glu Phe Ile Ala Ser Phe Tyr Asn Asn Asp Leu Ile Lys Ile Asn Gly
            980                 985                 990

Glu Leu Tyr Arg Val Ile Gly Val  Asn Asn Asp Leu Leu  Asn Arg Ile
            995                 1000                1005

Glu Val  Asn Met Ile Asp Ile  Thr Tyr Arg Glu Tyr  Leu Glu Asn
1010                 1015                1020

Met Asn Asp Lys Arg Pro Pro  Arg Ile Ile Lys Thr  Ile Ala Ser
1025                 1030                1035

Lys Thr  Gln Ser Ile Lys Lys  Tyr Ser Thr Asp Ile  Leu Gly Asn
1040                 1045                1050

Leu Tyr  Glu Val Lys Ser Lys  Lys His Pro Gln Ile  Ile Lys Lys
1055                 1060                1065

Gly Lys  Arg Pro Ala Ala Thr  Lys Lys Ala Gly Gln  Ala Lys Lys
1070                 1075                1080

Lys Lys  Gly Ser
1085
```

<210> SEQ ID NO 6
<211> LENGTH: 1087

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ala Pro Lys Lys Lys Arg Lys Val Gly Ile His Gly Val Pro Ala
1               5                   10                  15

Ala Lys Arg Asn Tyr Ile Leu Gly Leu Asp Ile Gly Ile Thr Ser Val
            20                  25                  30

Gly Tyr Gly Ile Ile Asp Tyr Glu Thr Arg Asp Val Ile Asp Ala Gly
        35                  40                  45

Val Arg Leu Phe Lys Glu Ala Asn Val Glu Asn Asn Glu Gly Arg Arg
    50                  55                  60

Ser Lys Arg Gly Ala Arg Arg Leu Lys Arg Arg Arg His Arg Ile
65                  70                  75                  80

Gln Arg Val Lys Lys Leu Leu Phe Asp Tyr Asn Leu Leu Thr Asp His
                85                  90                  95

Ser Glu Leu Ser Gly Ile Asn Pro Tyr Glu Ala Arg Val Lys Gly Leu
            100                 105                 110

Ser Gln Lys Leu Ser Glu Glu Glu Phe Ser Ala Ala Leu Leu His Leu
            115                 120                 125

Ala Lys Arg Arg Gly Val His Asn Val Asn Glu Val Glu Glu Asp Thr
    130                 135                 140

Gly Asn Glu Leu Ser Thr Lys Glu Gln Ile Ser Arg Asn Ser Lys Ala
145                 150                 155                 160

Leu Glu Glu Lys Tyr Val Ala Glu Leu Gln Leu Glu Arg Leu Lys Lys
                165                 170                 175

Asp Gly Glu Val Arg Gly Ser Ile Asn Arg Phe Lys Thr Ser Asp Tyr
            180                 185                 190

Val Lys Glu Ala Lys Gln Leu Leu Lys Val Gln Lys Ala Tyr His Gln
            195                 200                 205

Leu Asp Gln Ser Phe Ile Asp Thr Tyr Ile Asp Leu Leu Glu Thr Arg
    210                 215                 220

Arg Thr Tyr Tyr Glu Gly Pro Gly Glu Gly Ser Pro Phe Gly Trp Lys
225                 230                 235                 240

Asp Ile Lys Glu Trp Tyr Glu Met Leu Met Gly His Cys Thr Tyr Phe
                245                 250                 255

Pro Glu Glu Leu Arg Ser Val Lys Tyr Ala Tyr Asn Ala Asp Leu Tyr
            260                 265                 270

Asn Ala Leu Asn Asp Leu Asn Asn Leu Val Ile Thr Arg Asp Glu Asn
    275                 280                 285

Glu Lys Leu Glu Tyr Tyr Glu Lys Phe Gln Ile Ile Glu Asn Val Phe
    290                 295                 300

Lys Gln Lys Lys Lys Pro Thr Leu Lys Gln Ile Ala Lys Glu Ile Leu
305                 310                 315                 320

Val Asn Glu Glu Asp Ile Lys Gly Tyr Arg Val Thr Ser Thr Gly Lys
            325                 330                 335

Pro Glu Phe Thr Asn Leu Lys Val Tyr His Asp Ile Lys Asp Ile Thr
            340                 345                 350

Ala Arg Lys Glu Ile Ile Glu Asn Ala Glu Leu Leu Asp Gln Ile Ala
        355                 360                 365

Lys Ile Leu Thr Ile Tyr Gln Ser Ser Glu Asp Ile Gln Glu Glu Leu
    370                 375                 380
```

-continued

```
Thr Asn Leu Asn Ser Glu Leu Thr Gln Glu Glu Ile Glu Gln Ile Ser
385                 390                 395                 400

Asn Leu Lys Gly Tyr Thr Gly Thr His Asn Leu Ser Leu Lys Ala Ile
                405                 410                 415

Asn Leu Ile Leu Asp Glu Leu Trp His Thr Asn Asp Asn Gln Ile Ala
            420                 425                 430

Ile Phe Asn Arg Leu Lys Leu Val Pro Lys Lys Val Asp Leu Ser Gln
            435                 440                 445

Gln Lys Glu Ile Pro Thr Thr Leu Val Asp Asp Phe Ile Leu Ser Pro
        450                 455                 460

Val Val Lys Arg Ser Phe Ile Gln Ser Ile Lys Val Ile Asn Ala Ile
465                 470                 475                 480

Ile Lys Lys Tyr Gly Leu Pro Asn Asp Ile Ile Ile Glu Leu Ala Arg
                485                 490                 495

Glu Lys Asn Ser Lys Asp Ala Gln Lys Met Ile Asn Glu Met Gln Lys
            500                 505                 510

Arg Asn Arg Gln Thr Asn Glu Arg Ile Glu Glu Ile Ile Arg Thr Thr
            515                 520                 525

Gly Lys Glu Asn Ala Lys Tyr Leu Ile Glu Lys Ile Lys Leu His Asp
        530                 535                 540

Met Gln Glu Gly Lys Cys Leu Tyr Ser Leu Glu Ala Ile Pro Leu Glu
545                 550                 555                 560

Asp Leu Leu Asn Asn Pro Phe Asn Tyr Glu Val Asp His Ile Ile Pro
                565                 570                 575

Arg Ser Val Ser Phe Asp Asn Ser Phe Asn Asn Lys Val Leu Val Lys
            580                 585                 590

Gln Glu Glu Asn Ser Lys Lys Gly Asn Arg Thr Pro Phe Gln Tyr Leu
            595                 600                 605

Ser Ser Ser Asp Ser Lys Ile Ser Tyr Glu Thr Phe Lys Lys His Ile
        610                 615                 620

Leu Asn Leu Ala Lys Gly Lys Gly Arg Ile Ser Lys Thr Lys Lys Glu
625                 630                 635                 640

Tyr Leu Leu Glu Glu Arg Asp Ile Asn Arg Phe Ser Val Gln Lys Asp
                645                 650                 655

Phe Ile Asn Arg Asn Leu Val Asp Thr Arg Tyr Ala Thr Arg Gly Leu
            660                 665                 670

Met Asn Leu Leu Arg Ser Tyr Phe Arg Val Asn Asn Leu Asp Val Lys
            675                 680                 685

Val Lys Ser Ile Asn Gly Gly Phe Thr Ser Phe Leu Arg Arg Lys Trp
        690                 695                 700

Lys Phe Lys Lys Glu Arg Asn Lys Gly Tyr Lys His His Ala Glu Asp
705                 710                 715                 720

Ala Leu Ile Ile Ala Asn Ala Asp Phe Ile Phe Lys Glu Trp Lys Lys
                725                 730                 735

Leu Asp Lys Ala Lys Lys Val Met Glu Asn Gln Met Phe Glu Glu Lys
            740                 745                 750

Gln Ala Glu Ser Met Pro Glu Ile Glu Thr Glu Gln Glu Tyr Lys Glu
            755                 760                 765

Ile Phe Ile Thr Pro His Gln Ile Lys His Ile Lys Asp Phe Lys Asp
        770                 775                 780

Tyr Lys Tyr Ser His Arg Val Asp Lys Lys Pro Asn Arg Lys Leu Ile
785                 790                 795                 800
```

```
Asn Asp Thr Leu Tyr Ser Thr Arg Lys Asp Asp Lys Gly Asn Thr Leu
                805                 810                 815

Ile Val Asn Asn Leu Asn Gly Leu Tyr Asp Lys Asp Asn Asp Lys Leu
            820                 825                 830

Lys Lys Leu Ile Asn Lys Ser Pro Glu Lys Leu Leu Met Tyr His His
        835                 840                 845

Asp Pro Gln Thr Tyr Gln Lys Leu Lys Leu Ile Met Glu Gln Tyr Gly
    850                 855                 860

Asp Glu Lys Asn Pro Leu Tyr Lys Tyr Tyr Glu Glu Thr Gly Asn Tyr
865                 870                 875                 880

Leu Thr Lys Tyr Ser Lys Lys Asp Asn Gly Pro Val Ile Lys Lys Ile
            885                 890                 895

Lys Tyr Tyr Gly Asn Lys Leu Asn Ala His Leu Asp Ile Thr Asp Asp
            900                 905                 910

Tyr Pro Asn Ser Arg Asn Lys Val Val Lys Leu Ser Leu Lys Pro Tyr
            915                 920                 925

Arg Phe Asp Val Tyr Leu Asp Asn Gly Val Tyr Lys Phe Val Thr Val
    930                 935                 940

Lys Asn Leu Asp Val Ile Lys Lys Glu Asn Tyr Tyr Glu Val Asn Ser
945                 950                 955                 960

Lys Cys Tyr Glu Glu Ala Lys Lys Leu Lys Lys Ile Ser Asn Gln Ala
            965                 970                 975

Glu Phe Ile Ala Ser Phe Tyr Lys Asn Asp Leu Ile Lys Ile Asn Gly
            980                 985                 990

Glu Leu Tyr Arg Val Ile Gly Val  Asn Asn Asp Leu Leu  Asn Arg Ile
            995                 1000                1005

Glu Val  Asn Met Ile Asp Ile  Thr Tyr Arg Glu Tyr  Leu Glu Asn
    1010                1015                1020

Met Asn  Asp Lys Arg Pro Pro  His Ile Ile Lys Thr  Ile Ala Ser
    1025                1030                1035

Lys Thr  Gln Ser Ile Lys Lys  Tyr Ser Thr Asp Ile  Leu Gly Asn
    1040                1045                1050

Leu Tyr  Glu Val Lys Ser Lys  Lys His Pro Gln Ile  Ile Lys Lys
    1055                1060                1065

Gly Lys  Arg Pro Ala Ala Thr  Lys Lys Ala Gly Gln  Ala Lys Lys
    1070                1075                1080

Lys Lys  Gly Ser
    1085
```

```
<210> SEQ ID NO 7
<211> LENGTH: 964
<212> TYPE: DNA
<213> ORGANISM: Homo sapiens

<400> SEQUENCE: 7
tcttcacctg tcattttcaa ccagcctcag cctatctgct ctgtcacaat cactactaaa        60
atatgttcct aaattgcttg tttctagatc cttccttctc atatgctcag gtgaacacat       120
gggtgaaatt taatatggaa ttgaaatatg tactatgcaa gatagattcc ttaagaaatg       180
tttctctgat ttatatgaca taattgtatt ttactagttt acctgtccat ctgtaaaact       240 ttgtttttgga gatttcatat attacaatgt ttaagaaata tgctataatg ttttgtatag       300
tatatttctt cgtgataacc ttatatacta ccagtcacac gtgtttgtaa aaatctaaag       360
agtacttttg gctcctacag aatgtgtgaa gttgtgaaat tgttttttttg ttttgttttg       420
```

```
ttttgttttt atgccccaaa gatgtggagg gcttcatata agagggtaga tttaatgaga      480
gagagaggga gagacagaga gaatgataaa agaagcttaa gagattattt tatcttgtca      540
acgacattgt tattgaatgt aagctgctaa acttcttaga taaagtaaaa cagtaaaaac      600
aaacacacaa aacagaacag agaatcatca gacaggctga cgaacacagt acaataaagc      660
agccagtacc gatgatcagt ggacatcaat ttgtcttttg ggctgtagca cctgctacta      720
attggtgcaa agcgctcacc agtcagtgcg tggtttagcg cactcagctg tctcctgtat      780
gtgctgcgag aagcaagata gctaattgct gttgcttcag tgccagtgaa atcaacgtgc      840
tgagctaata gcgacagata gagggcagac agattcctgc tagcagctta gtgttagttg      900
cttgtggtaa ctaaggcagg tggcatacat ctcagaacgt ggagaatgat ggtatgcttt      960
ctga                                                                   964

<210> SEQ ID NO 8
<211> LENGTH: 1040
<212> TYPE: DNA
<213> ORGANISM: Homo sapiens

<400> SEQUENCE: 8
tggtagcctc cctagagaca cagagctggg ccggatgagt ccaggcactg acgtgatcca       60
ttatctttca ccttaaagag taaaagggaa actaaagtta attacctcca cgaaacaaaa      120
aggtgccttc ttgtgcttca attacatgga tatattctac tagtctaaaa gtatcttctc      180
acttctttct gtcactgtga ggacttgagt cagaagaaag tttaaataca gtcattgagc      240
tggaaagagt ggaaagagaa gcaaagaggg ggaagctgta ggaaggacga agtcaccccc      300
aagatacatg gttactgctt acaccaagca agctgccttg ggaacgcttc ccccgagcag      360
ccagaatgct cagcagtgga agacacctct attcctgtag gcgagtcctg ggaagctggt      420
caatctgcaa atgccaattc ccagcagtga gctcggtcca cgtgtaaatc aagatttggg      480
gaaagagtag ggtgggtggc atggttgaca atgtcatcag ctccctcctc tgactcctgt      540
ggtcgtgccc ccatctactc tcactcagct acaccccacc ttcggatttg tgatggacgc      600
tgggtcccta gtaaccacag caagtgtctc ccccgcactt ccccttccc cacccccacc      660 cccacccca accaccaccc cagcgatgga gcctactctg ctccaagccg ccgctaagac      720
ccggagaagc ggaatttcac tttgaaattc ccttgcctcg tgagggccgg cgctgggcat      780
gctcagtagc cgcggcgctg ctgctgggct gctgggctgg cgcggagtcc accctgccgt      840
ctccgccttg gcttctgggc gtccagaagg ccaggcattt gccgcctctg agcgcttctg      900 ttcccttac ccgcaacctc ctactgctct tcctctctcc ctctcttagg gaggttgaag       960
ctggtgctgg tttctgtcgg cgccacagac tgactgctct gcaaacccca gccgaggacc      1020
tgaatcccgg agactagaag                                                  1040

<210> SEQ ID NO 9
<211> LENGTH: 964
<212> TYPE: DNA
<213> ORGANISM: Homo sapiens

<400> SEQUENCE: 9
gcccagtgga attttcctag ttctttacac tagccatgta tttacctata aaatcaggag       60
aaatatgtat atatataata tattaaaaca tatatatatt taaatgggga aatatgtaac      120
aaacaaatag aaacaagggg agaaaggcat tgtatttgac aaaacacata tgttcaggtc      180
tgagaaggct cataaagaat gttgtctgct atactttgta gttgcttctg ttatcacaca      240
```

-continued

```
atcagtctgc atatacaggc gttttatata tatatttata tagactacat atatacgtat      300
attatatatg taaatatttc actgtctttg aggacggggg ccctgtcttt tttatctgtg      360
gttttgctta gatgtcctcc aacataatct taacacatag tatgctttta gaaatcgttg      420
actgaatgct aaggacgaaa aaccggtgac cagaaggcaa ccaggaaagg ctttgctgac      480
ctccggagtg gtggagttgg aggttctggg aaggcgacta gggagccagg caggggcggg      540
gtgggatggg atgtggacag cgcttttgcg gggggaaagc gtttttgctg ctggaattga      600
gcagtaggaa tgtgtcagtc acatccccac cttcccaatt cttgtcatct cggttcagga      660
aggtgaacgg tgttccgatt ccccgcggcg ggggcctgta gtgggagctc tgccccttcc      720
ccgcctctgc tgcaggcccc gcccctcgcc cggaacccccg gggcgctggc cgcggtgctg      780
aaacggcgcc ctccgcggac ggaggagggg gcggggctct cgggagccgt gagccgggaa      840
gagggagacg ggcagggcgg cgccagcagg ccctggtggg cttgggagga ggcaggagac      900
tggagacagc ctcggctaga gcggacacag gcacctggca agctttcctt gaccaaatca      960
aggt                                                                   964
```

```
<210> SEQ ID NO 10
<211> LENGTH: 477
<212> TYPE: DNA
<213> ORGANISM: Unknown
<220> FEATURE:
<223> OTHER INFORMATION: Description of Unknown:
      Synapsin promoter sequence

<400> SEQUENCE: 10
```

```
tctagactgc agagggccct gcgtatgagt gcaagtgggt tttaggacca ggatgaggcg       60
gggtgggggt gcctacctga cgaccgaccc cgacccactg gacaagcacc caaccccat       120 tccccaaatt gcgcatcccc tatcagagag ggggaggggga aacaggatgc ggcgaggcgc      180
gtgcgcactg ccagcttcag caccgcggac agtgccttcg cccccgcctg gcggcgcgcg      240
ccaccgccgc ctcagcactg aaggcgcgct gacgtcactc gccggtcccc cgcaaactcc      300
ccttcccggc caccttggtc gcgtccgcgc cgccgccggc ccagccggac cgcaccacgc      360
gaggcgcgag atagggggggc acgggcgcga ccatctgcgc tgcggcgccg gcgactcagc      420
gctgcctcag tctgcggtgg gcagcggagg agtcgtgtcg tgcctgagag cgcagtc        477
```

```
<210> SEQ ID NO 11
<211> LENGTH: 760
<212> TYPE: PRT
<213> ORGANISM: Homo sapiens

<400> SEQUENCE: 11
```

```
Met Ser Pro Lys Lys Val Gln Ile Lys Val Glu Glu Lys Glu Asp Glu
1               5                   10                  15

Thr Glu Glu Ser Ser Ser Glu Glu Glu Glu Val Glu Asp Lys Leu
            20                  25                  30

Pro Arg Arg Glu Ser Leu Arg Pro Lys Arg Lys Arg Thr Arg Asp Val
            35                  40                  45

Ile Asn Glu Asp Asp Pro Glu Pro Glu Asp Glu Glu Thr Arg
        50                  55                  60

Lys Ala Arg Glu Lys Glu Arg Arg Arg Arg Leu Lys Arg Gly Ala Glu
65                  70                  75                  80

Glu Glu Glu Ile Asp Glu Glu Glu Leu Glu Arg Leu Lys Ala Glu Leu
                85                  90                  95
```

-continued

```
Asp Glu Lys Arg Gln Ile Ile Ala Thr Val Lys Cys Lys Pro Trp Lys
            100             105             110

Met Glu Lys Lys Ile Glu Val Leu Lys Glu Ala Lys Lys Phe Val Ser
            115             120             125

Glu Asn Glu Gly Ala Leu Gly Lys Gly Lys Gly Lys Arg Trp Phe Ala
            130             135             140

Phe Lys Met Met Met Ala Lys Lys Trp Ala Lys Phe Leu Arg Asp Phe
145             150             155             160

Glu Asn Phe Lys Ala Ala Cys Val Pro Trp Glu Asn Lys Ile Lys Ala
                165             170             175

Ile Glu Ser Gln Phe Gly Ser Ser Val Ala Ser Tyr Phe Leu Phe Leu
            180             185             190

Arg Trp Met Tyr Gly Val Asn Met Val Leu Phe Ile Leu Thr Phe Ser
            195             200             205

Leu Ile Met Leu Pro Glu Tyr Leu Trp Gly Leu Pro Tyr Gly Ser Leu
            210             215             220

Pro Arg Lys Thr Val Pro Arg Ala Glu Glu Ala Ser Ala Ala Asn Phe
225             230             235             240

Gly Val Leu Tyr Asp Phe Asn Gly Leu Ala Gln Tyr Ser Val Leu Phe
                245             250             255

Tyr Gly Tyr Tyr Asp Asn Lys Arg Thr Ile Gly Trp Met Asn Phe Arg
                260             265             270

Leu Pro Leu Ser Tyr Phe Leu Val Gly Ile Met Cys Ile Gly Tyr Ser
            275             280             285

Phe Leu Val Val Leu Lys Ala Met Thr Lys Asn Ile Gly Asp Asp Gly
            290             295             300

Gly Gly Asp Asp Asn Thr Phe Asn Phe Ser Trp Lys Val Phe Thr Ser
305             310             315             320

Trp Asp Tyr Leu Ile Gly Asn Pro Glu Thr Ala Asp Asn Lys Phe Asn
            325             330             335

Ser Ile Thr Met Asn Phe Lys Glu Ala Ile Thr Glu Glu Lys Ala Ala
            340             345             350

Gln Val Glu Glu Asn Val His Leu Ile Arg Phe Leu Arg Phe Leu Ala
            355             360             365

Asn Phe Phe Val Phe Leu Thr Leu Gly Gly Ser Gly Tyr Leu Ile Phe
            370             375             380

Trp Ala Val Lys Arg Ser Gln Glu Phe Ala Gln Gln Asp Pro Asp Thr
385             390             395             400

Leu Gly Trp Trp Glu Lys Asn Glu Met Asn Met Val Met Ser Leu Leu
                405             410             415

Gly Met Phe Cys Pro Thr Leu Phe Asp Leu Phe Ala Glu Leu Glu Asp
                420             425             430

Tyr His Pro Leu Ile Ala Leu Lys Trp Leu Leu Gly Arg Ile Phe Ala
            435             440             445

Leu Leu Leu Gly Asn Leu Tyr Val Phe Ile Leu Ala Leu Met Asp Glu
            450             455             460

Ile Asn Asn Lys Ile Glu Glu Glu Lys Leu Val Lys Ala Asn Ile Thr
465             470             475             480

Leu Trp Glu Ala Asn Met Ile Lys Ala Tyr Asn Ala Ser Phe Ser Glu
                485             490             495

Asn Ser Thr Gly Pro Pro Phe Phe Val His Pro Ala Asp Val Pro Arg
            500             505             510
```

-continued

```
Gly Pro Cys Trp Glu Thr Met Val Gly Gln Glu Phe Val Arg Leu Thr
        515                 520                 525

Val Ser Asp Val Leu Thr Thr Tyr Val Thr Ile Leu Ile Gly Asp Phe
        530                 535                 540

Leu Arg Ala Cys Phe Val Arg Phe Cys Asn Tyr Cys Trp Cys Trp Asp
545                 550                 555                 560

Leu Glu Tyr Gly Tyr Pro Ser Tyr Thr Glu Phe Asp Ile Ser Gly Asn
                565                 570                 575

Val Leu Ala Leu Ile Phe Asn Gln Gly Met Ile Trp Met Gly Ser Phe
                580                 585                 590

Phe Ala Pro Ser Leu Pro Gly Ile Asn Ile Leu Arg Leu His Thr Ser
        595                 600                 605

Met Tyr Phe Gln Cys Trp Ala Val Met Cys Cys Asn Val Pro Glu Ala
        610                 615                 620

Arg Val Phe Lys Ala Ser Arg Ser Asn Asn Phe Tyr Leu Gly Met Leu
625                 630                 635                 640

Leu Leu Ile Leu Phe Leu Ser Thr Met Pro Val Leu Tyr Met Ile Val
                645                 650                 655

Ser Leu Pro Pro Ser Phe Asp Cys Gly Pro Phe Ser Gly Lys Asn Arg
                660                 665                 670

Met Phe Glu Val Ile Gly Glu Thr Leu Glu His Asp Phe Pro Ser Trp
        675                 680                 685

Met Ala Lys Ile Leu Arg Gln Leu Ser Asn Pro Gly Leu Val Ile Ala
        690                 695                 700

Val Ile Leu Val Met Val Leu Ala Ile Tyr Tyr Leu Asn Ala Thr Ala
705                 710                 715                 720

Lys Gly Gln Lys Ala Ala Asn Leu Asp Leu Lys Lys Lys Met Lys Met
                725                 730                 735

Gln Ala Leu Glu Asn Lys Met Arg Asn Lys Lys Met Ala Ala Ala Arg
                740                 745                 750

Ala Ala Ala Ala Ala Gly Arg Gln
        755                 760
```

```
<210> SEQ ID NO 12
<211> LENGTH: 3201
<212> TYPE: DNA
<213> ORGANISM: Homo sapiens

<400> SEQUENCE: 12
cagaaactat gagggcagaa cccagcaatc tgtgctttct ttcacaagcc ctccaggagt        60
tgctgaaatt taggaatcat tgccccaaaa agtggccctc ataatgatgc cagatgggat       120
cttactctgt tgcccaggct ggagtgcagt ggtgcgatct cggctctctg caacctccgc       180
ctcccaggtt caagtgattc tcctgcctcg gcctcctgag tagctgggat ttcaggccat       240
gaaagatcac tgttttagtc tgcgtggtgc agtggaacag atagacctcg gtttgaatct       300
cagctctact gtttactaga catgaaatgg ggaaatctaa aatgagatgc cagaagcctc       360
aaaaatggaa aaccccctgt gcttcacatc tgaaaatctc tgctgggggc agcaactttg       420
agcctgtggg gaaggaactg tccacgtgga gtggtctggt gaatgcttaa ggagctgcag       480
aagggaagtc cctctccaaa ctagccagcc actgagacct tctgacagga caccccagg       540 atgtcaccca aaaagtacaa atcaaagtg gaggaaaaag aagacgagac tgaggaaagc       600
tcaagtgaag aggaagagga ggtggaagat aagctaccc gaagagagag cttgagacca       660
aagaggaaac ggaccagaga tgttatcaat gaggatgacc cagaacctga accagaggat       720
```

-continued

```
gaagaaacaa ggaaggcaag agaaaaagag aggaggagga ggctaaagag aggagcagaa      780
gaagaagaaa ttgatgaaga ggaattggaa agattgaagg cagagttaga tgagaaaaga      840
caaataattg ctactgtcaa atgcaaacca tggaagatgg agaagaaaat tgaagttctc      900
aaggaggcaa aaaaatttgt gagtgaaaat aaggggctc ttgggaaagg aaaaggaaaa        960
cggtggtttg catttaagat gatgatggcc aagaaatggg caaaattcct ccgtgatttt     1020
gagaacttca aagctgcgtg tgtcccatgg gaaaataaaa tcaaggctat tgaaagtcag     1080
tttggctcct cagtggcctc atacttcctc ttcttgagat ggatgtatgg agtcaatatg     1140
gttctcttta tcctgacatt tagcctcatc atgttgccag agtacctctg gggtttgcca     1200
tatggcagtt tacctaggaa aaccgttccc agagccgaag aggcatcggc agcaaacttt     1260
ggtgtgttgt acgacttcaa tggtttggca caatattccg ttctctttta tggctattat     1320
gacaataaac gaacaattgg atggatgaat ttcaggttgc cgctctccta ttttctagtg     1380
gggattatgt gcattggata cagctttctg gttgtcctca aagcaatgac caaaaacatt     1440
ggtgatgatg gaggtggaga tgacaacact ttcaatttca gctggaaggt ctttaccagc     1500
tgggactacc tgatcggcaa tcctgaaaca gcagacaaca aatttaattc tatcacaatg     1560
aactttaagg aagctatcac agaagaaaaa gcagcccaag tagaagaaaa cgtccacttg     1620
atcagattcc tgaggtttct ggctaacttc ttcgtgtttc taacacttgg agggagtgga     1680
tacctcatct tttgggctgt gaagcgatcc caggaatttg cacagcaaga tcctgacacc     1740
cttgggtggt gggaaaaaaa tgaaatgaac atggttatgt ccctcctagg gatgttctgt     1800
ccaacattgt ttgacttatt tgctgaatta gaagactacc atcctctcat cgctttgaaa     1860
tggctactgg gacgcatttt tgctcttctt ttaggcaatt tatacgtatt tattcttgca     1920
ttaatggatg agattaacaa caagattgaa gaggagaagc tagtaaaggc caatattacc     1980
ctttgggaag ccaatatgat caaggcctac aatgcatcat ctctgaaaa tagcactgga     2040 ccaccctttt ttgttcaccc tgcagatgta cctcgaggac cttgctggga aacaatggtg     2100
ggacaggagt ttgtgaggct gacagtctct gatgttctga ccacctacgt cacaatcctc     2160 attgggggact ttctaagggc atgttttgtg aggttttgca attattgctg gtgctgggac    2220
ttggagtatg gatatccttc atacaccgaa ttcgacatca gtggcaacgt cctcgctctg     2280
atcttcaacc aaggcatgat ctggatgggc tccttctttg ctcccagcct cccaggcatc     2340
aatatccttc gactccatac atccatgtac ttccagtgct gggccgttat gtgctgcaat     2400
gttcctgagg ccagggtctt caaagcttcc agatcaaata acttctacct gggcatgcta     2460
ctgctcatcc tcttcctgtc cacaatgcct gtcttgtaca tgatcgtgtc cctcccacca     2520
tcttttgatt gtggtccatt cagtggcaaa aatagaatgt ttgaagtcat tggagagacc     2580
ctggagcacg atttcccaag ctggatggcg aagatcttga acagctttc aaaccctggg      2640 ctggtcattg ctgtcatttt ggtgatggtt ttggccatct attatctcaa tgctactgcc     2700
aagggccaga aggcagcgaa tctggatctc aaaaagaaga tgaaaatgca agctttggag     2760
aacaaaatgc gaaacaagaa aatggcagct gcacgagcag ctgcagctgc tggtcgccag     2820
taataagtat cctgagagcc cagaaaaggt acactttgcc ttgctgttta aaagtaatgc     2880
aatatgtgaa cgcccagaga acaagcactg tggaactgct attttcctgt tctacccttg     2940
atggattttc aaggtcatgc tggccaatta aggcatcatc agtcctacct gagcaacaag     3000 aatctaaaact ttattccaag tcagaaactg tttctgcaga gccactctct cccctgctcc    3060
```

```
atttcgtgac tttttttttt tttttaacaa attgagttta gaagtgagtg taatccagca    3120
atacagttta ctggtttagt tggtgggtta attaaaaaaa atttgctcat atgaactttc    3180
attttatatg tttcttttgc c                                              3201
```

<210> SEQ ID NO 13
<211> LENGTH: 7
<212> TYPE: PRT
<213> ORGANISM: Unknown
<220> FEATURE:
<223> OTHER INFORMATION: Description of Unknown:
      AAV-PHP.B sequence

<400> SEQUENCE: 13

```
Thr Leu Ala Val Pro Phe Lys
1               5
```

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14

```
gggacagaac ttccccagga ggg                                              23
```

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15

```
tgggacagaa cttccccagg agg                                              23
```

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16

```
gggtgggaca gaacttcccc agg                                              23
```

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17

```
gtgggacaga acttccccag gag                                              23
```

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic -continued

```
            oligonucleotide

<400> SEQUENCE: 18
agggtgggac agaacttccc cag                                          23

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tggtaatgtc cctcctgggg aag                                          23

<210> SEQ ID NO 20
<211> LENGTH: 39
<212> TYPE: DNA
<213> ORGANISM: Mus sp.
<220> FEATURE:
<221> NAME/KEY: CDS
<222> LOCATION: (1)..(39)

<400> SEQUENCE: 20 atg gta atg tcc ctc ctg ggg aag ttc tgt ccc acc ctg               39
Met Val Met Ser Leu Leu Gly Lys Phe Cys Pro Thr Leu
1               5                   10

<210> SEQ ID NO 21
<211> LENGTH: 13
<212> TYPE: PRT
<213> ORGANISM: Mus sp.

<400> SEQUENCE: 21

Met Val Met Ser Leu Leu Gly Lys Phe Cys Pro Thr Leu
1               5                   10

<210> SEQ ID NO 22
<211> LENGTH: 39
<212> TYPE: DNA
<213> ORGANISM: Mus sp.

<400> SEQUENCE: 22
atggtaatgt ccctcctggg gatgttctgt cccaccctg                         39

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gtggacagaa cttccctagg aggg                                         24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
```

-continued gttggacaga acttccctag gagg                                                24

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
atgttggaca gaacttccct agg                                                 23

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gttggacaga acttccctag gag                                                 23

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
aatgttggac agaacttccc tag                                                 23

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gtggttatgt ccctcctagg gaag                                                24

<210> SEQ ID NO 29
<211> LENGTH: 39
<212> TYPE: DNA
<213> ORGANISM: Homo sapiens
<220> FEATURE:
<221> NAME/KEY: CDS
<222> LOCATION: (1)..(39)

<400> SEQUENCE: 29 atg gtt atg tcc ctc cta ggg aag ttc tgt cca aca ttg                      39
Met Val Met Ser Leu Leu Gly Lys Phe Cys Pro Thr Leu
1               5                   10

<210> SEQ ID NO 30
<211> LENGTH: 13
<212> TYPE: PRT
<213> ORGANISM: Homo sapiens

<400> SEQUENCE: 30

Met Val Met Ser Leu Leu Gly Lys Phe Cys Pro Thr Leu
1               5                   10

-continued

```
<210> SEQ ID NO 31
<211> LENGTH: 39
<212> TYPE: DNA
<213> ORGANISM: Homo sapiens

<400> SEQUENCE: 31
atggttatgt ccctcctagg gatgttctgt ccaacattg                              39

<210> SEQ ID NO 32
<211> LENGTH: 12
<212> TYPE: DNA
<213> ORGANISM: Mus sp.

<400> SEQUENCE: 32
ggatgttctg tc                                                          12

<210> SEQ ID NO 33
<211> LENGTH: 12
<212> TYPE: DNA
<213> ORGANISM: Mus sp.

<400> SEQUENCE: 33
ggawgttctg tc                                                          12

<210> SEQ ID NO 34
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ggatgttctg tc                                                          12

<210> SEQ ID NO 35
<211> LENGTH: 40
<212> TYPE: DNA
<213> ORGANISM: Mus sp.

<400> SEQUENCE: 35
gaacatggta atgtccctcc tggggaagtt ctgtcccacc                             40

<210> SEQ ID NO 36
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gaacatggta atgtccctcc tggggagttc tgtcccacc                              39

<210> SEQ ID NO 37
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gaacatggta atgtccctcc tgggagttct gtcccacc                               38
```

-continued

```
<210> SEQ ID NO 38
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gaacatggta atgtccctcc tgggaagttc tgtcccacc                              39

<210> SEQ ID NO 39
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gaacatggta atgtccctcc tggggaaagt tctgtcccac                             40

<210> SEQ ID NO 40
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gaacatggta atgtccctcc taagttctgt cccacc                                 36

<210> SEQ ID NO 41
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gaacatggta atgtccctcc tgggagaagt tctgtcccac                             40

<210> SEQ ID NO 42
<211> LENGTH: 40
<212> TYPE: DNA
<213> ORGANISM: Mus sp.

<400> SEQUENCE: 42
gaacatggta atgtccctcc tggggatgtt ctgtcccacc                             40

<210> SEQ ID NO 43
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gaacatggta atgtccctcc tgggatgttc tgtcccacc                              39
```